US010047021B2

(12) United States Patent
Smith et al.

(10) Patent No.: US 10,047,021 B2
(45) Date of Patent: Aug. 14, 2018

(54) METHOD FOR TUNING PRODUCT COMPOSITION BASED ON VARYING TYPES AND RATIOS OF FEED

(71) Applicant: UOP LLC, Des Plaines, IL (US)

(72) Inventors: Stuart Smith, Lake Zurich, IL (US); Alakananda Bhattacharyya, Glen Ellyn, IL (US); Peter K. Coughlin, Mundelein, IL (US)

(73) Assignee: UOP LLC, Des Plaines, IL (US)

( * ) Notice: Subject to any disclaimer, the term of this patent is extended or adjusted under 35 U.S.C. 154(b) by 583 days.

(21) Appl. No.: 14/303,584

(22) Filed: Jun. 12, 2014

(65) Prior Publication Data

US 2015/0005560 A1    Jan. 1, 2015

Related U.S. Application Data

(60) Provisional application No. 61/841,266, filed on Jun. 28, 2013.

(51) Int. Cl.
*C07C 6/08* (2006.01)
*C07C 6/10* (2006.01)
(Continued)

(52) U.S. Cl.
CPC .......... *C07C 6/10* (2013.01); *C07C 2/58* (2013.01); *C07C 4/06* (2013.01); *C07C 5/2702* (2013.01); *C07C 5/277* (2013.01); *C07C 5/2751* (2013.01); *C07C 2527/054* (2013.01); *C07C 2527/08* (2013.01); *C07C 2527/11* (2013.01); *C07C 2527/12* (2013.01); *C07C 2527/122* (2013.01); *C07C 2527/125* (2013.01); *C07C 2527/128* (2013.01); *C07C 2527/138* (2013.01); *C07C 2527/14* (2013.01); *C07C 2527/24* (2013.01)

(58) Field of Classification Search
CPC ........................................... C07C 6/10
USPC .................. 585/708, 721, 752, 740, 734
See application file for complete search history.

(56) References Cited

U.S. PATENT DOCUMENTS

| 5,082,987 A * | 1/1992 | Olbrich ............. C07C 7/13 502/31 |
| 5,233,121 A | 8/1993 | Modica |

(Continued)

FOREIGN PATENT DOCUMENTS

| EP | 1 346 768 B1 | 9/2003 |
| EP | 2 520 558 A1 | 11/2012 |

(Continued)

OTHER PUBLICATIONS

Pellegrini, L.A.; Gamba,S.; Bonomi, S.; Calemma, V. "Equilibrium Constants for Isomerization of n-Paraffins", Ind. Eng. Chem. Res. (2007), 46, pp. 5446-5452.*

(Continued)

*Primary Examiner* — Philip Y Louie
*Assistant Examiner* — Aaron W Pierpont

(57) ABSTRACT

A process of tuning a hydrocarbon product composition is described. The process involves selecting paraffins for reaction. The equilibrium constants for reactions of the selected paraffins can be used to select appropriate feed ratios, or an equilibrium composition as function of C/H molar ratio. A selected feed is reacted to obtain the product. Equilibrium product compositions and non-equilibrium product compositions can be obtained using the process.

15 Claims, 6 Drawing Sheets

(51) Int. Cl.
*C07C 5/27* (2006.01)
*C07C 2/58* (2006.01)
*C07C 4/06* (2006.01)

(56) References Cited

U.S. PATENT DOCUMENTS

| | | | |
|---|---|---|---|
| 5,750,455 | A | 5/1998 | Chauvin et al. |
| 6,235,959 | B1 | 5/2001 | Hirschauer et al. |
| 6,288,281 | B1 | 9/2001 | Nemeth et al. |
| 6,623,659 | B2 | 9/2003 | Munson et al. |
| 6,797,853 | B2 | 9/2004 | Houzvicka et al. |
| 7,053,261 | B2 | 5/2006 | Herbst et al. |
| 7,285,698 | B2 | 10/2007 | Liu et al. |
| 7,432,408 | B2 | 10/2008 | Timken et al. |
| 7,432,409 | B2 | 10/2008 | Elomari et al. |
| 7,495,144 | B2 | 2/2009 | Elomari |
| 7,531,707 | B2 | 5/2009 | Harris et al. |
| 7,782,501 | B2 | 8/2010 | Serizawa |
| 7,902,417 | B2 | 3/2011 | Goldman et al. |
| 8,183,425 | B2 | 5/2012 | Luo et al. |
| 8,187,994 | B2 | 5/2012 | Harris |
| 8,198,494 | B2 | 6/2012 | Elomari et al. |
| 8,198,499 | B2 | 6/2012 | Luo et al. |
| 8,222,471 | B2 | 7/2012 | Elomari et al. |
| 8,247,628 | B2 | 8/2012 | Hommeltoft et al. |
| 8,288,601 | B2 | 10/2012 | Hommeltoft et al. |
| 8,319,001 | B2 | 11/2012 | Hommeltoft |
| 2003/0109767 | A1 | 6/2003 | Vasina et al. |
| 2003/0181780 | A1 | 9/2003 | Herbst et al. |
| 2003/0196931 | A1* | 10/2003 | Houzvicka .............. C10G 59/02 208/65 |
| 2004/0059173 | A1 | 3/2004 | Houzvicka et al. |
| 2004/0077914 | A1* | 4/2004 | Zavilla ................. B01J 31/0227 585/737 |
| 2005/0033102 | A1* | 2/2005 | Randolph ............ B01J 31/0294 585/708 |
| 2007/0142218 | A1* | 6/2007 | Harris .................... B01J 27/125 502/53 |
| 2008/0021254 | A1* | 1/2008 | Schmidt ................. H02S 40/44 585/702 |
| 2009/0171133 | A1 | 7/2009 | Luo et al. |
| 2011/0105811 | A1 | 5/2011 | O'Rear et al. |
| 2011/0105820 | A1 | 5/2011 | Harris |
| 2011/0137098 | A1 | 6/2011 | Tschirschwitz et al. |
| 2011/0184219 | A1 | 7/2011 | Timken et al. |
| 2011/0319693 | A1 | 12/2011 | Hommeltoft et al. |
| 2011/0319694 | A1 | 12/2011 | Timken et al. |
| 2012/0165590 | A1 | 6/2012 | Liu et al. |
| 2012/0165593 | A1 | 6/2012 | Liu et al. |
| 2012/0172647 | A1 | 7/2012 | Liu et al. |
| 2012/0178982 | A1 | 7/2012 | Liu et al. |
| 2012/0264605 | A1 | 10/2012 | Rogers et al. |
| 2012/0282150 | A1 | 11/2012 | Timken et al. |
| 2013/0062253 | A1 | 3/2013 | Timken |
| 2013/0066121 | A1 | 3/2013 | Zhan et al. |
| 2013/0066130 | A1 | 3/2013 | Luo et al. |

FOREIGN PATENT DOCUMENTS

| | | |
|---|---|---|
| EP | 2 597 078 A1 | 5/2013 |
| JP | 2011098924 A2 | 5/2011 |
| WO | WO 00/40673 | 7/2000 |

OTHER PUBLICATIONS

Huibin et al., "Reaction performance and . . . ," Catalysis Communications, v 12, n 3, p. 180-183, Nov. 30, 2010.
Zinurov et al., "Skeletal Isomerization of . . . ," Petroleum Chemistry, v 50, n 5, p. 376-380, Sep. 2010.
Petre et al., "Dodecylbenzene transformations: Dealkylation and . . . ," Applied Catalysis A: General, v 363, n 1-2, p. 100-108, Jul. 1, 2009.
Schmidt et al., "Disproportionation of Light Paraffins," Energy and Fuels, v 22, n 3. p. 1812-1823, May/Jun. 2008.
Shi et al., "Influence of initiators on . . . ," Journal of Fuel Chemistry and Technology, v 36, n 3, p 306-310, Jun. 2008.
Shi et al, "Isomerization of normal hexane . . . ," Ranliao Huaxue Xuebao/Journal of Fuel Chemistry and Technology: v 36, n 5, p. 594-600, Oct. 2008.
Ibragimov et al., "Isomerization of Light Alkanes . . . ," Theoretical Foundations of Chemical Engineering (2013), 47(1), 66-70.
Berenblyum et al., "The nature of catalytic activity . . . ," Applied Catalysis, A: General (2006), 315, 128-134.
Dötterl et al., "Catalytic coupling and cracking . . . ," Catalysis Communications (2012), 19, 28-30.
Vasina et al., "Effect of Adamantane-Containing Additives . . . ," Russian Journal of Physical Chemistry A (2013), 87(1), 20-22.
Liu et al., "Alkylation of isobutane/butene with . . . ," Huaxue Fenying Gongcheng Yu Gongyi (2004), 20(3), pp. 229-234.
Huang et al., "Alkylation of isobutane with butene in . . . ," Shiyou Daxue Xuebao, Ziran Kexueban (2003), 27(4), pp. 120-122.
Huang et al., "Alkylation of isobutane with butene . . . ," Shiyou Lianzhi Yu Huagong (2002), 33(11), pp. 11-13.
Liu et al., "Isobutane alkylation catalyzed by composite . . . ," Ranliao Huaxue Xuebao (2006), 34(3), pp. 328-331.
Liu et al., "Isobutane-alkylation over ionic . . . ," Huaxue Fanying Gongcheng Yu Gongyi (2009), 25(4), pp. 311-317.
Liu et al., "Research progress of ionic liquids . . . ," Huaxue Shiji (2010) 32(12), pp. 1085-1088.
Liu et al., "Study on the Alkylation of . . . ," Fenzi Cuihua (2010), 24(3), pp. 217-221.
Liu et al., "Ionic liquid alkylation process . . . ," Oil & Gas Journal (2006), 104(40), pp. 52-56.
Meyer et al., "Effective n-octane isomerization . . . ," Chemical Communications (Cambridge, United Kingdom) (2010), 46(40), pp. 7625-7627.
Shiriyazdanov et al., "Alkylation of isobutane by the butane-butene . . . ," Theoretical and Experimental Chemistry (2011), 47(1), pp. 45-48.
Shengwei et al., "Improved 1-butene/isobutane alkylation . . . ," Journal of Catalysis (2009), 268(2), pp. 243-250.
Xing et al., "Chlorogallate(III) ionic liquids: Synthesis, acidity . . . " Science China: Chemistry (2012), 55(8), pp. 1542-1547.
Xing et al., "Isobutane alkylation using acidic ionic . . . ," Catalysis Communications (2012), 26, pp. 68-71.
Yoo et al., "Ionic liquid-catalyzed alkylation of . . . ," Journal of Catalysis (2004), 222(2), pp. 511-519.
Yoo et el., "Preparation and Characterization of . . . ," AIChE Annual Meeting, Conference Proceedings, Cincinnati, OH, United States, Oct. 30-Nov. 4, 2005 (2005), 289i/1-289.
Zhang et al., "Isomerization of n-Pentane Catalyzed by . . . ," Industrial & Engineering Chemistry Research (2008), 47(21), pp. 8205-8210.

* cited by examiner

METHOD FOR TUNING PRODUCT COMPOSITION BASED ON VARYING TYPES AND RATIOS OF FEED

This application claims priority to U.S. Provisional Application Ser. No. 61/841,266, entitled "METHOD FOR TUNING PRODUCT COMPOSITION BASED ON VARYING TYPES AND RATIOS OF FEED," filed Jun. 28, 2013.

BACKGROUND OF THE INVENTION

The Reid vapor pressure (RVP) of gasoline has been utilized by the Environmental Protection Agency as a means of regulating volatile organic compounds emissions by transportation fuels and for controlling the formation of ground level ozone. As these regulations become more stringent and as more ethanol (which has a high vapor pressure) is blended into gasoline, $C_5$ paraffins need to be removed from the gasoline pool. Moreover, the need to remove components may also extend to some $C_6$ paraffins. This may result in refiners being oversupplied with $C_5$ paraffins and possibly $C_6$ paraffins.

Disproportionation reactions offer a possible solution to this problem. The disproportionation of paraffins (e.g., iso-pentane ($iC_5$)) involves reacting two moles of hydrocarbon to form one mole each of two different products, one having a carbon count greater than the starting material and the other having a carbon count less than the starting material, as shown in FIG. 1. The total number of moles in the system remains the same throughout the process, but the products have different carbon counts from the reactants. Additional secondary disproportionation-type reactions can occur in which two hydrocarbons having different carbon numbers react to form two different hydrocarbons having different carbon numbers from those of the feed where the total number of carbons in the products does not change from the total number in the feed (e.g., pentane and octane reacting to form hexane and heptane).

There are a number of different catalysts that have been shown to produce the desired paraffin disproportionation reaction, including zeolites, sulfated zirconias, $AlCl_2/SiO_2$, ionic solids, platinum on chlorided $Al_2O_3/Ga_2O_3$ supports, supported ionic liquids. $Pt/W/Al_2O_3$ and $HF/TiF_4$. However, these processes have a number of disadvantages. The processes using zeolites, sulfated zirconias, $AlCl_2/SiO_2$, ionic solids, and platinum on $Al_2O_3/Ga_2O_3$ supports require elevated temperatures (e.g., 120-450° C.) to carry out the transformation. The $HF/TiF_4$ system is capable of disproportionation at 51° C. but it utilizes dangerous HF. The supported ionic liquid is active from about 85-125° C. and is composed of the Brønsted acidic trimethylammonium cation. Since the ionic liquid's organic cation is composed of this Brønsted acid, the acid concentration within this catalyst is stoichiometric with respect to the ionic liquid and quite high. Moreover, the supported ionic liquid is deactivated by leaching of the ionic liquid from the support. Additionally, the use of a support increases the cost of the catalyst and may result in a chemical reaction of the support with the acidic ionic liquid over time, as happens when $AlCl_3$ is immobilized on silica.

Isomerization processes have been used to improve the low octane numbers (RON) of light straight run naphtha. Isomerization processes involve reacting one mole of a hydrocarbon (e.g., normal pentane) to form one mole of an isomer of that specific hydrocarbon (e.g. isopentane), as shown in FIG. 2. The total number of moles remains the same throughout this process, and the product has the same number of carbons as the reactant.

Current isomerization processes use chlorided alumina, sulfated zirconia, or zeolites in conjunction with platinum. Process temperatures range from about 120° C. for chlorided alumina up to about 260° C. for zeolite type catalysts. These reactions are run at temperatures which allow the feed to reach equilibrium. At lower temperatures, the equilibrium favors the branched isomers possessing the higher octane number.

Isomerization processes utilizing ionic liquids have been developed. For example, US 2003/019767 describes an isomerization process for a paraffin hydrocarbon feed using an ionic liquid as a catalyst. The ionic liquid is formed from an N-containing heterocyclic and/or N-containing aliphatic organic cation and an inorganic anion derived from metal halides. The examples show a catalyst:hydrocarbon weight ratio of 1:1 or 1.5:1. The hydrocarbon feeds examined were normal pentane, normal heptane, normal octane, and 3-methylhexane.

US 2004/059173 teaches an isomerization process for linear and/or branched paraffin hydrocarbons. The catalyst comprises an ionic liquid. Over 25 wt. % of a cyclic hydrocarbon additive is included. The ionic liquid is formed from an N-containing heterocyclic and/or N-containing aliphatic organic cation and an inorganic anion derived from metal halides. The ionic liquid:hydrocarbon ratio in the examples is fixed at 1:1 volume ratio. Metal salt additives or Brønsted acids can be included. The feed is a mixture of $C_7$ hydrocarbons.

U.S. Pat. No. 7,053,261 discusses isomerization of linear and/or branched paraffin hydrocarbons using an ionic liquid catalyst in combination with a metal salt additive. The ionic liquid is formed from an N-containing heterocyclic and/or N-containing aliphatic organic cation and an inorganic anion derived from metal halides. The ionic liquid:hydrocarbon ratio in the examples is fixed at 1:1 volume ratio. The results of the gas chromatograph on the paraffin phase were not reported. The feed is a mixture of $C_7$ hydrocarbons.

All of these references describe isomerization of the feed; none describes disproportionation reactions. All of the references describe the use of ionic liquids having an acid concentration of at least about 3.0 M. The Brønsted acidic ionic liquid used in US Publication 2003/0109767 was [trimethylammonium][$Al_2Cl_7$], which has a molar concentration of HCl that ranges from 3.0-4.1 M if the density is in the range of 1.1 to 1.5 g/mL. For US Publications 2004/0059173 and U.S. Pat. No. 7,053,261 the Brønsted acidic ionic liquid used was [trimethylammonium][$Al_{1.8}Cl_{6.4}$], which has a molar concentration of HCl that ranges from 3.3-4.5 M if the density is in the range of 1.1 to 1.5 g/mL. These estimated densities are within the ranges measured for similar ionic liquids.

None of the references indicate the composition of the product mixture: as a result, it is unclear what was actually formed in the reactions. Assuming that all of the other products were disproportionation products (which is unlikely to be correct as Ibragimov et al. teach that cracking occurs in addition to disproportionation (see below), but it sets an upper limit on the greatest possible conversion, yield, etc. for the disproportionation products). The conversion rates corrected for mass or volume were calculated as follows: using the reported iso-selectivity, the selectivity to other compounds was calculated as (100-iso-selectivity). The % conversion was determined from the reported %-iso yield and % iso-selectivity. The % conversion thus determined was used to determine the reaction rate by the following formula: volume rate=(% conversion/time (h))× (mL HC/mL IL) or as mass rate=(% conversion/time (h))×(g HC/g IL). The % conversion was then used with the computed selectivity to other compounds to set an upper limit on the yield of disproportionation products. The yield of the other compounds and yield of isomers was then calculated using the calculated selectivity to other compounds and the total yield. Since the reaction rate is dependent on the ratio of ionic liquid:hydrocarbon, the rates were corrected according to these ratios.

With respect to US 2003/0109767, the corrected conversion rates for mass were very low. For n-$C_5$, the corrected conversion rate for mass ranged was between 3.5 and 18.2. For n-$C_7$, it ranged from 2.6 to 9.3, for n-$C_8$, it was 3.3, and for 3-methylhexane, it was 4.7. For US 2005/059173, the corrected conversion rates for volume ranged from 0.6 to 47.1 for the $C_7$ mixture. For U.S. Pat. No. 7,053,261, the corrected conversion rates for volume ranged from 5.4 to 371.3 in the presence of an additional metal salt.

Isomerization is also described in "Isomerization of Light Alkanes Catalysed by Ionic Liquids: An Analysis of Process Parameters," Ibragimov et al., Theoretical Foundations of Chemical Engineering (2013), 47(1), 66-70. The desired reaction is stated to be isomerization, and the main isomerization products from n-hexane are said to be isobutane, isopentane, and hexane isomers. However, isobutane and isopentane are not the isomerization products of n-hexane as isomerization has been defined above. In addition, the article discusses the fact that a significant amount of an undesirable disproportionation reaction begins to occur after about 2-3 hrs. The article indicates that the disproportionation reaction dominates when the ratio of catalyst to hydrocarbon ratio is 2:1, and that cracking and disproportionation dominate at 333K. Because cracking is occurring, the number of moles formed is increased. The optimum isomerization temperature was 303K. The maximum volume rate they obtained was 26 at their high mixing speeds (900 rpm or more) at 0.5 hr.

Some processes involve isomerization and then a cracking reaction in which one mole of a hydrocarbon forms two moles of product, each with a lower carbon number than the starting material. In FIG. 3, the products are illustrated as an alkene and an alkane. Additionally, the total number of moles increases throughout the process.

Alkylation processes involving ionic liquids are also known. In alkylation reactions, one mole of an alkane and one mole of an alkene react to form one mole of an alkane having a carbon number equal to the sum of the carbon numbers of the starting alkane and alkene, as shown in FIG. 4. In an alkylation process, the total number of moles in the system is reduced.

There is a need for methods of controlling the product feeds to obtain desired product compositions.

SUMMARY OF THE INVENTION

One aspect of the invention is a process of tuning a hydrocarbon product composition. In one embodiment, the process includes selecting a range of paraffins, and determining a series of equilibrium constants for reactions of the selected range of paraffins. A desired product composition is selected based on an equilibrium composition. A hydrocarbon feed is selected based on the desired product composition, the selected hydrocarbon feed comprising at least one $C_n$ alkane where n=1-200. A feed ratio is determined based on the selected hydrocarbon feed and the desired product composition. The selected hydrocarbon feed is reacted by contacting the selected hydrocarbon feed with a liquid catalyst in the determined feed ratio in a reaction zone under tuning conditions to form the desired product composition, the liquid catalyst comprising an ionic liquid and a carbocation promoter, and the desired product composition is recovered.

Another aspect of the invention relates to a process of tuning a hydrocarbon product composition. In one embodiment, the process involves selecting a range of paraffins, and determining a series of equilibrium constants for reactions of the selected range of paraffins. An equilibrium composition of the selected range of paraffins as a function of C/H molar ratio is determined. A hydrocarbon feed to react is selected, the selected hydrocarbon feed comprising at least one $C_n$ alkane where n=1-200. The selected hydrocarbon feed is reacted by contacting the selected hydrocarbon feed with a liquid catalyst in a reaction zone under tuning conditions to form the product composition, the liquid catalyst comprising an ionic liquid and a carbocation promoter.

In one embodiment, an equilibrium composition is obtained. A desired equilibrium product composition is selected from the equilibrium composition corresponding to a selected C/H molar ratio. The hydrocarbon feed is selected based on the desired equilibrium product composition, and the C/H molar ratio of the selected hydrocarbon feed matches the selected C/H molar ratio of the desired equilibrium product composition. The selected hydrocarbon feed is reacted to form the desired substantially equilibrium product composition, and the desired substantially equilibrium product composition is recovered.

In another embodiment, a non-equilibrium composition is obtained. The C/H molar ratio of the selected hydrocarbon feed is determined, and the equilibrium composition at the C/H molar ratio for the selected hydrocarbon feed is determined. The selected hydrocarbon feed is reacted to form a desired non-equilibrium product composition, and the desired non-equilibrium product composition is recovered.

DETAILED DESCRIPTION OF THE INVENTION

Figure 1:
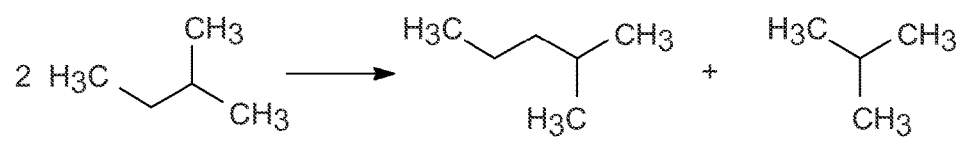
FIG. 1 illustrates the disproportionation reaction of isopentane.

Paraffins have a wide range of properties which makes some paraffin isomers more valuable than others. For example, isobutane has an RON of 100 and an RVP of 71 psi, while normal pentane has an RON of 62, and an RVP of 15.6 psi. This dramatic difference in properties leads to differences in refiners' valuation of various products depending on their location, the source of crude oil, and their desired product specifications. Constantly changing product demands sometimes result in too much of a less desirable product and too little of a more desirable one, resulting in increased prices for the more desired product. Furthermore, an excess of a particular feed can lead to a lower price for that feed.

It would be desirable to have a process that allows a refiner to select a particular desired product preferentially, such as gasoline, diesel, kerosene, or some other paraffin containing product, depending on the market situation at a particular time and to shift easily from one product to another as the demand changes. In addition, it would be desirable to be able to select the feed used in the process to produce a desired product based on the available supply of possible feeds, allowing maximization of the use of lower price feeds. The product composition can be tuned by varying the types and amounts of different feeds. The process utilizes one or more of disproportionation, reverse disproportionation, and isomerization of the selected feed to form the desired product.

It has been demonstrated that an acidic ionic liquid and a carbocation promoter can catalyze the disproportionation of paraffins, as discussed below. In this reaction, two moles of a paraffin are used to create one mole each of two different paraffins one larger in carbon count and one smaller than the starting paraffin. For example, pentane can be converted to a product mixture containing butane and hexane.

Reverse disproportionation involves the microscopic reverse of the disproportionation reaction, for example, in which one mole of hexane and one mole of butane react to form two moles of pentane. Utilizing the equilibrium among the various species, the concentration of the product can be controlled by varying the relative ratios of the species. Consequently, two different paraffinic feed sources of varying carbon count can be reacted to obtain a product of intermediate carbon count.

More generally, this process involves the net transfer of $CH_2$ units between paraffins, where $CH_2$ unit refers to the transfer of 1 C and 2 H, not necessarily a methylene unit. The products result from the donation and acceptance of net $CH_2$ units to and from various paraffins. Thus, two paraffinic feeds having different carbon counts can be reacted to produce a product having an intermediate carbon count. For example, the reaction of butane with a larger paraffin, e.g., $C_6$, produces a product containing paraffins in the $C_5$ to $C_{15}$ range.

In addition to the net $CH_2$ transfer, the process favors the formation of branched paraffins, which are more valuable than normal paraffins because they have more desirable octane numbers and cloud points.

Figure 7:
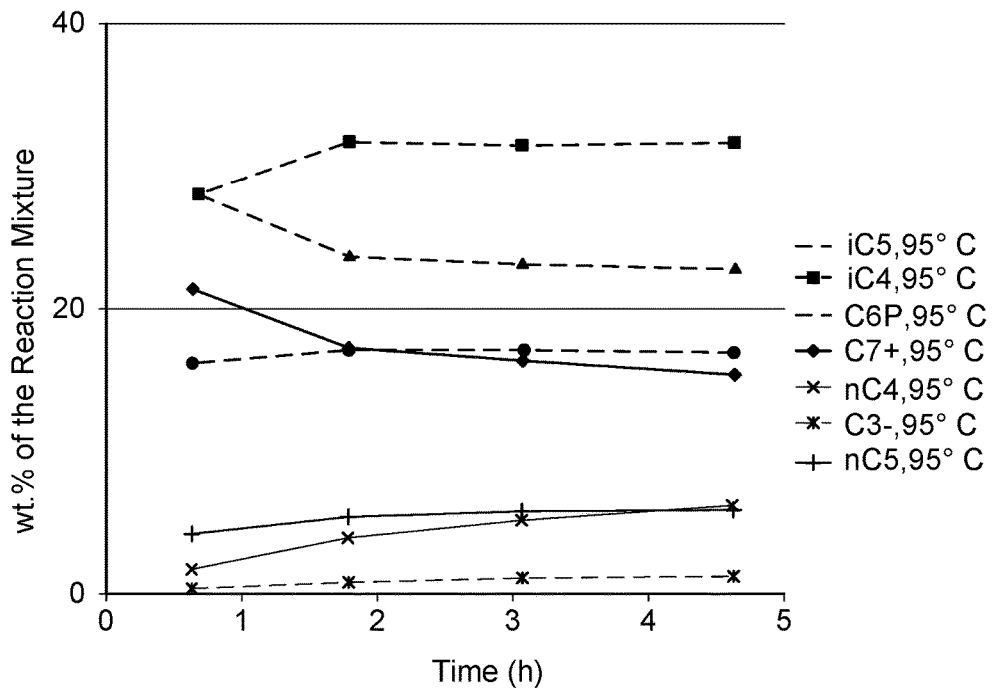
FIG. 7 is graph showing the concentration of components in a disproportionation reaction mixture of isopentane over time.
Figure 8:
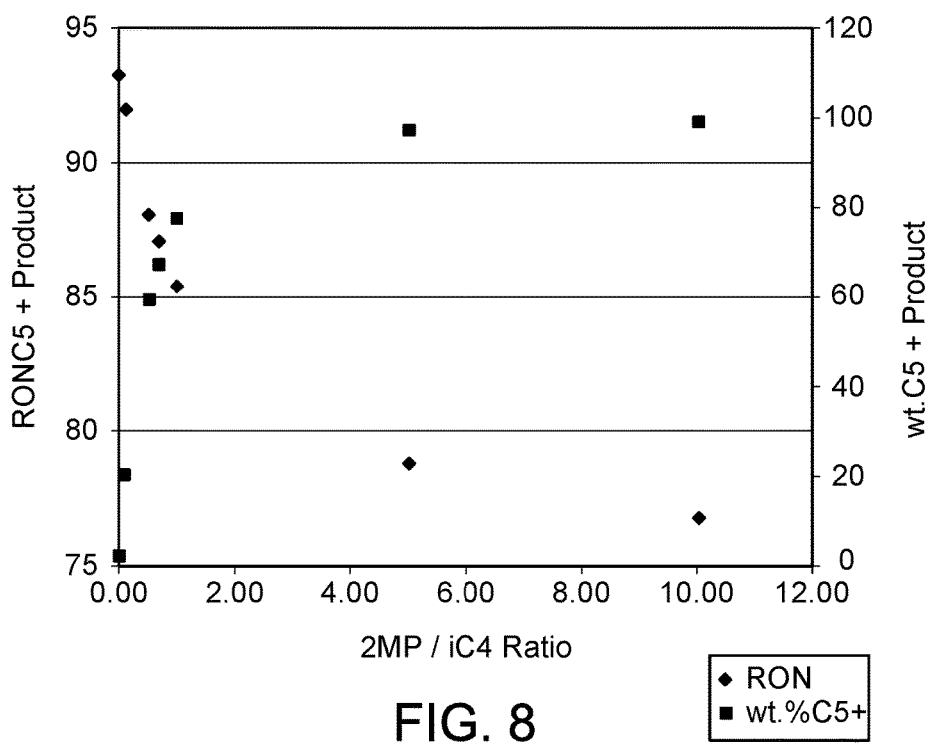
FIG. 8 is a graph showing the weight of $C_{5+}$ products and RON at various feed ratios of 2-methylpentane/isobutane if the reaction were to be run to equilibrium and were to include only isopentane, 2-methylpentane and isobutane as the components present.

The Gibbs free energy for these types of reactions is relatively small. Consequently, the equilibrium constants for these reactions are not substantially large or small for any given reaction. Due to these modest equilibrium constants, at equilibrium measurable amounts of both reactant and product will be formed. As shown in FIG. 7, an equilibrium appears to have been reached among butanes, pentanes, hexanes and $C_{7+}$ paraffins in the disproportionation reaction of isopentane. The estimated equilibrium constant for the specific disproportionation reaction of two moles of isopentane to one mole of isobutane and one mole of 2-methylpentane is Keq=0.3 based on the enthalpy of formation and the molar entropy for the reactants and products. The value observed by gas chromatography was 0.4, which is in good agreement with the calculated value. Furthermore, the ratio of the products did not change as the reaction time was increased.

The general formula for a paraffin is $C_nH_{2n+2}$. For any given paraffin, it can be represented by a C/H molar ratio. For example, C/H molar ratio for both isobutane and normal butane is 0.400, while the ratio for isopentane and normal pentane is about 0.417. Blends of two or more paraffins can produce C/H molar ratios in the range of about 0.25 to about 0.50.

For a given C/H molar ratio, there exists a specific equilibrium mixture. For a given subset of paraffins, there exists a defined equilibrium composition at a given C/H molar ratio. If this subset is chosen such that it encompasses the majority of the measurable products, then this equilibrium composition for this subset of paraffins can be used to approximate the composition of the product at the end of a reaction, provided a catalyst could be identified to carry out this equilibration for these paraffins. At the specified C/H molar ratio, if a compound is present in excess of its equilibrium concentration, then it will be consumed. Conversely, if a compound is present at less than its equilibrium concentration, it will be produced. By appropriate selection of feeds, desired compounds can be produced, and undesired compounds can be consumed.

As illustrated in Table A, Feeds 1 and 2 have the same C/H molar ratio, 0.406, but they have different starting compositions. Both feeds will produce the same product composition. With Feed 1, the amounts of the $C_4$ and $C_7$ paraffins are in excess of the equilibrium amounts, and so both will be consumed to produce the equilibrium mixture. With Feed 2, the amount of $C_5$ paraffin is in excess of the equilibrium amount, so it will be consumed, while the amount of $C_4$ paraffin is less the equilibrium amount, so it will be produced.

TABLE A

| Compound | Feed 1 (mole %) | Feed 2 (mole %) | Product (mole %) |
| --- | --- | --- | --- |
| C4P | 90 | 70 | 76.5 |
| C5P | 0 | 30 | 17.9 |
| C6P | 0 | 0 | 4.7 |
| C7P | 10 | 0 | 0.8 |
| C8P | 0 | 0 | 0.1 |
| C/H | 0.406 | 0.406 | 0.406 |

Figure 9:
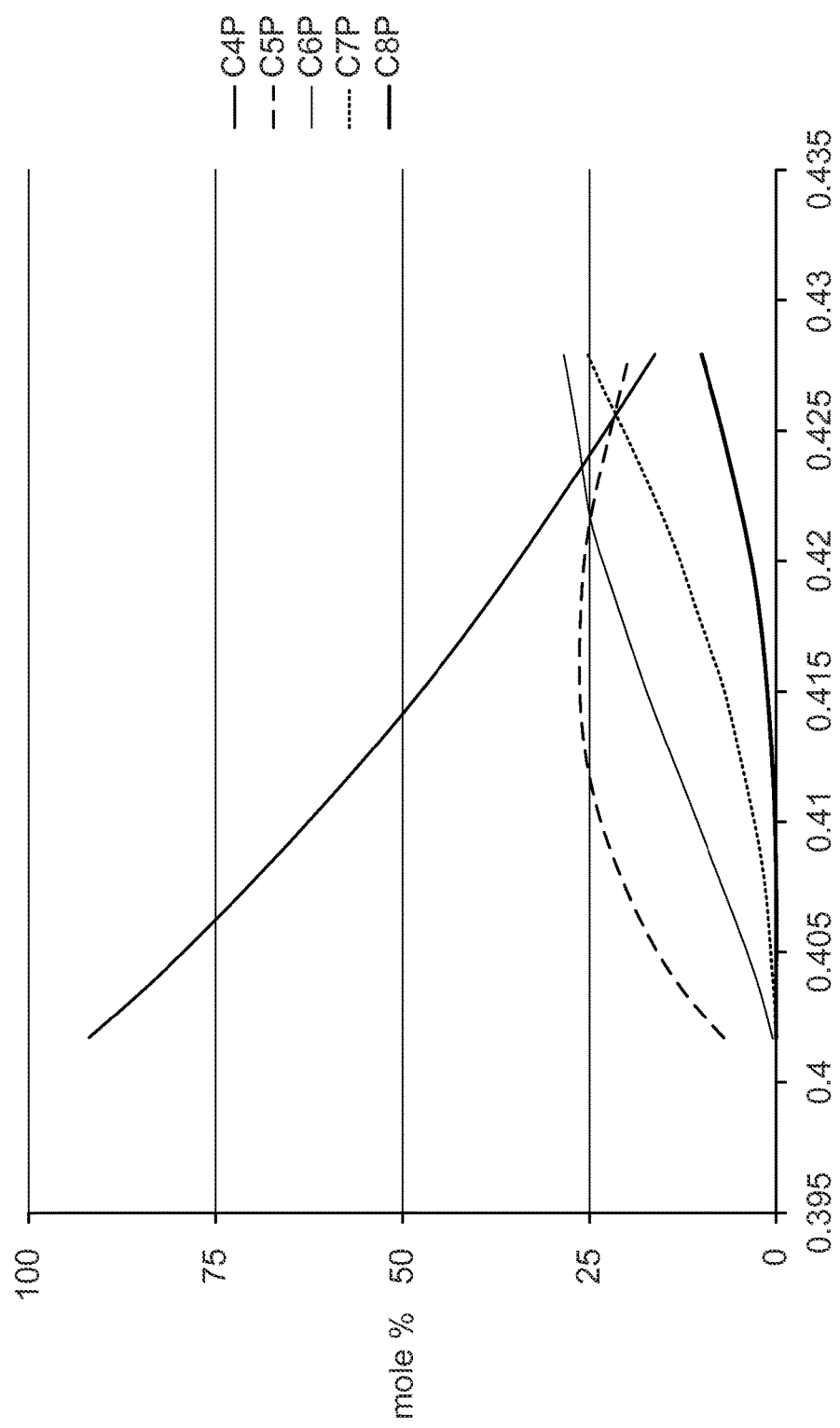
FIG. 9 is a graph of the equilibrium composition (in mole %) of $C_4$ to $C_8$ paraffins as a function of the C/H ratio at 100° C.

FIG. 9 shows a graph of the equilibrium composition (in mole %) of a subset of paraffins ($C_4$ to $C_8$ paraffins) as a function of the C/H molar ratio. The equilibrium constants for all of the reactions (isomerization and disproportionation) were determined using values for an ideal gas at 100° C. from "The Chemical Thermodynamics of Organic Compounds" by Daniel R Stull, Edgar F. Westrum, Jr. and Gerard C. Sinke, copyright 1969. As demonstrated in FIG. 9, the equilibrium product composition is a function of C/H ratio of the feed. The composition listed is for a subset of paraffins; the figure can be extended to include paraffins larger than $C_8$ and smaller than $C_4$, if desired. These product compositions represent the equilibrium composition for specific C/H molar ratios of this subset of paraffins, provided a catalyst can be identified to carry out these reactions. Once a catalyst has been identified that is capable of catalyzing these reactions, the product composition will eventually yield the equilibrium composition as set by the C/H molar ratio. Suitable catalysts include those capable of catalyzing paraffin disproportionation, reverse disproportionation, metathesis, alkylation and isomerization reactions. Suitable reaction times are less than about two days, or less than about one day, or less than about 18 h, or less than about 12 h, or less than about 6 h, or less than about 5 h, or less than about 4 h, or less than about 3 h, or less than about 2 h, or less than about 1 h. The use of the catalyst in conjunction with the known equilibrium composition based on the molar C/H ratio then allows for selective production and consumption of specific paraffins. For instance, if a refiner had an excess of butanes and wished to react these away, the refiner would identify an acceptable equilibrium product composition based on the C/H molar ratio, and then react the butanes with a suitable paraffin such that the predetermined C/H molar ratio would be achieved. In this manner, the undesired butanes would be upgraded and produce the predetermined acceptable product composition.

Figure 10:
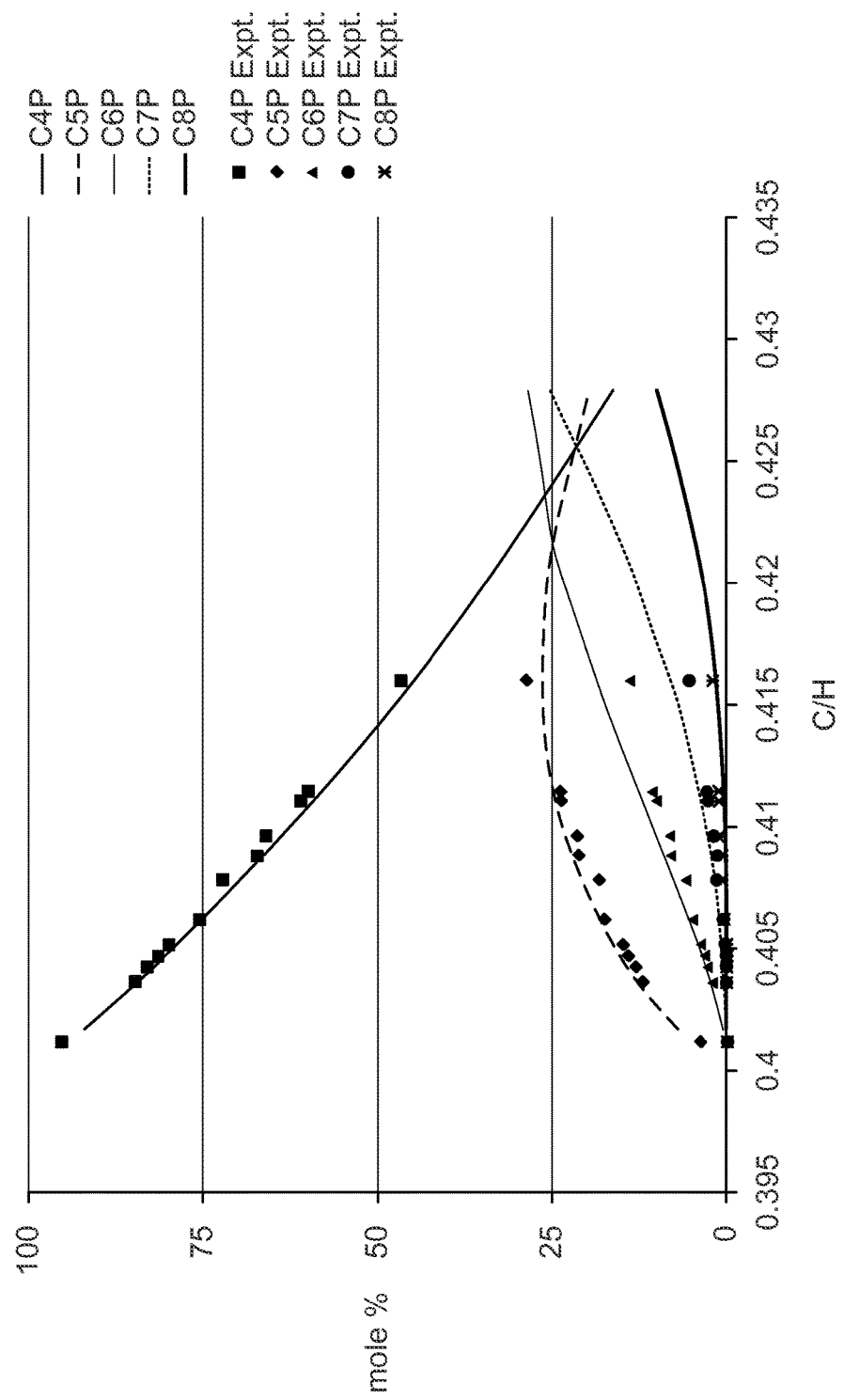
FIG. 10 is a graph comparing the calculated equilibrium composition (in mole %) of $C_4$ to $C_8$ paraffins as a function of the C/H ratio at 100° C. compared to the experimental data on the mole % distribution of the C4+ fraction.

FIG. 10 shows a graph comparing the calculated equilibrium product composition (in mole %) of $C_4$ to $C_8$ paraffins as a function of the C/H molar ratio to the mole % distribution of the C4+ fraction in experimental data. The graph shows very good agreement between the predicted value and the experimental data. The experimental data included in FIG. 10 are from Examples 10, 17, 18, 22, 26, 27, 30, 32, 33, 35-37.

Thus, a refiner can select a desired product composition from the figure (or a corresponding graph including the appropriate paraffins), and determine the C/H molar ratio corresponding to that desired product composition. The refiner may then choose one or more low valued feed streams to achieve the C/H molar ratio necessary to obtain the desired calculated equilibrium product composition. In this approach, the product composition is independent of the composition of the feed since it is reacted to equilibrium and the product composition will be known beforehand. Alternatively, a refiner may use the same figure to obtain a desired product composition that is significantly different from the equilibrium composition by choosing a feed that is not at its equilibrium composition and reacting for a period of time shorter than that required to reach equilibrium. In this approach, the refiner would be targeting the initial products formed from the starting material: in this approach, the product composition may be dependent on the composition of the feed.

Although this is a simplified system, an equilibrium constant exists for any combination of paraffins. Once the constants are known, the feed ratios required for obtaining specific compositions of one or more desired products can be determined. By selecting the appropriate feed compositions and feed ratios, various product compositions can be obtained.

The reaction can be allowed to proceed to form an equilibrium (or substantially equilibrium) product composition, as described above. By "substantially equilibrium product composition," we mean that the product composition contains 95 wt % or more of the equilibrium product composition for at least one component as determined by the C/H ratio, or 95 wt % or more of the equilibrium product composition for at least two components, or 95 wt % or more of the equilibrium product composition for at least three components. When more than one component is considered, the components have consecutive carbon numbers, e.g., $C_4$, $C_5$, and $C_6$. While a component may have reached equilibrium, it is not required that the isomers of the component have reached their equilibrium. For example, the $C_4$ component may have reached the equilibrium concentration, but it may not have reached the equilibrium for normal butane and isobutane.

In other embodiments, there may be a desire for a non-equilibrium product composition. By "non-equilibrium product composition," we mean that the product composition contains less than 95 wt % of the equilibrium product composition for at least one component as determined by the C/H ratio, or less than 95 wt % of the equilibrium product composition for at least two components, or less than 95 wt % of the equilibrium product composition for at least three components. When more than one component is considered, the components have consecutive carbon numbers, e.g., $C_4$, $C_5$, and $C_6$. For example, a product containing an iC4/nC4 ratio greater than the equilibrium amount may be desired. The present process allows the production of such desired non-equilibrium products.

After determining the equilibrium composition of the selected range of paraffins as a function of C/H molar ratio and selecting the hydrocarbon feed, the C/H molar ratio of the selected hydrocarbon feed is determined. The equilibrium composition at the C/H molar ratio for the selected hydrocarbon feed is then determined. The selected hydrocarbon feed is then reacted to form a desired non-equilibrium product composition. The reaction is stopped before the equilibrium product composition is reached. The product composition can be monitored to determine the appropriate stopping point to obtain the desired non-equilibrium composition. Suitable monitoring methods are known to those of skill in the art and include, but are not limited to, gas chromatography (GC), gas chromatography mass spectrometry (GC-MS) and GC×GC. The desired non-equilibrium product composition can then be recovered.

The process can be controlled to obtain a certain desired property for the product composition. For example, desired properties could include one or more of research octane number, boiling point, boiling range, cloud point, pour point, viscosity, density and Reid vapor pressure. The hydrocarbon feed would be selected based on the product composition and the desired property.

In some embodiments, the recovered product is separated into two or more product streams, for example by boiling point. In some embodiments, all or a portion of one or more of the product streams can be recycled back to the reaction zone. The amount of recycle can be adjusted to maintain a desired C/H molar ratio of the hydrocarbon stream entering the reaction zone at a particular value.

The ionic liquid can be separated from the product, and recycled to the reaction zone. The used ionic liquid can be regenerated before being recycled to the reaction zone as needed.

In some embodiments, the C/H molar ratio of the selected hydrocarbon feed is in the range of about 0.25 to about 0.50, or about 0.30 to about 0.50, or about 0.40 to about 0.50, or about 0.40 to about 0.49, or about 0.40 to about 0.48, or about 0.40 to about 0.47, or about 0.40 to about 0.46, or about 0.40 to about 0.45, or about 0.40 to about 0.44, or about 0.40 to about 0.43, or about 0.40 to about 0.42, or about 0.40 to about 0.41.

Typically, hydrocarbons having a carbon number from 1-200 or more can be selected as feeds for the process. Depending on the desired product, one or two (or more) hydrocarbon feeds could be selected.

In some embodiments involving reverse disproportion, one larger and one smaller paraffin feed can be used to produce a product composition having an intermediate carbon count. The smaller feed typically has carbon numbers ranging from 1-198, and the larger feed typically has carbon numbers ranging from 3-200. There is generally a difference of at least 2 or more carbon numbers between the two feeds, or at least 3, or at least 4, or at least 5, or at least 6 or more. In some embodiments involving reverse disproportionation, the reaction mixture has an amount of at least one of the intermediate products equal to or in excess of the amount formed by the disproportionation reaction of either feed alone.

By the appropriate selection and reaction of hydrocarbon feeds, products of a desired composition can be obtained. This could allow the use of readily available but lesser valued feeds to produce more valuable products.

For example, the production of natural gas liquids, which includes butanes, is rapidly increasing. As a result of this increase, the price of butanes could be significantly reduced, creating a burden for producers. Only a small fraction of butanes can be included in the gasoline pool because of its high vapor pressure. Reverse disproportionation offers a possible solution. The reaction of butanes with a larger paraffin, e.g., $C_{12}$, can produce a product mixture containing paraffins in the $C_5$ to $C_{11}$ range gasoline range, as well as some $C_{3-}$ and $C_{13+}$ paraffins.

Other highly desirable products include kerosene, which is widely used for jet fuel, and diesel, the demand for which currently exceeds that of gasoline. They are currently obtained by the distillation of crude oil and hydrocracking of heavier feeds. Therefore, a process which converts low value paraffins into kerosene or diesel would be very beneficial. As an example, the reaction of a gasoline range paraffin, such as $C_9$, with a larger paraffin, such as $C_{16}$, can produce a product mixture in the $C_{10}$ to $C_{15}$ range, as well as some $C_{8-}$ and $C_{17+}$ paraffins. In a like manner, the reaction a gasoline range paraffin, such as $C_9$, with a much larger paraffin, such as $C_{25}$, can produce a product mixture in the $C_{10}$ to $C_{24}$ range, as well as some $C_{8-}$ and $C_{26+}$ paraffins.

Light paraffins and methane are difficult compounds to react; as a result, they can be a source of wasted carbon in a refinery. Because of their low reactivity and high vapor pressure, the utility of the compounds is limited. For example, only small amounts of these compounds can be blended into gasoline. As the production of shale gas and shale crude continues, these light paraffins and methane will be produced on an even larger scale, which will depress their value further.

Methane can be reacted with $C_{3+}$ paraffins to form a mixture of $C_{2+}$ paraffins. For example, methane could be reacted with propane to form $C_2$ paraffin. Methane could be reacted with butane to form a mixture of $C_2$ and $C_3$ paraffins. Methane could be reacted with pentane to form a mixture of $C_2$ to $C_4$ paraffins. Methane could be reacted with a light naphtha stream ($C_5$ to $C_6$ paraffins) to form a mixture of $C_2$ to $C_{4-5}$ paraffins. Methane could be reacted with a heavy naphtha stream ($C_7$ to $C_{12}$ paraffins) to form a mixture of $C_2$ to $C_{11}$ paraffins. Methane could be reacted with a heavy paraffin stream ($C_{12+}$ paraffins) to form a mixture of $C_2$ to $C_{11+}$ paraffins.

Ethane can be reacted with $C_{4+}$ paraffins to form a mixture of $C_{3+}$ paraffins. For example, ethane could be reacted with butane to form $C_3$ paraffins. Ethane could be reacted with pentane to form a mixture of $C_3$ to $C_4$ paraffins. Ethane could be reacted with a light naphtha stream ($C_5$ to $C_6$ paraffins) to form a mixture of $C_3$ to $C_{4-5}$ paraffins. Ethane could be reacted with a heavy naphtha stream ($C_7$ to $C_{12}$ paraffins) to form a mixture of $C_3$ to $C_{10}$ paraffins. Ethane could be reacted with a heavy paraffin stream ($C_{2+}$ paraffins) to form a mixture of $C_3$ to $C_{11}$ paraffins.

Propane can be reacted with $C_{5+}$ paraffins to form a mixture of $C_{4+}$ paraffins. For example, propane could be reacted with pentane to form $C_4$ paraffins. Propane could be reacted with a light naphtha stream ($C_5$ to $C_6$ paraffins) to form a mixture of $C_4$ to $C_5$ paraffins. Propane could be reacted with a heavy naphtha stream ($C_7$ to $C_{12}$ paraffins) to form a mixture of $C_4$ to $C_{11+}$ paraffins. Propane could be reacted with a heavy paraffin stream ($C_{12+}$ paraffins) to form a mixture of $C_4$ to $C_{11+}$ paraffins.

Butane can be reacted with $C_{6+}$ paraffins to form a mixture of $C_{5+}$ paraffins. For example, butane could be reacted with a light naphtha stream ($C_5$ to $C_6$ paraffins) to form a mixture of $C_5$ paraffins. Butane could be reacted with a heavy naphtha stream ($C_7$ to $C_{12}$ paraffins) to form a mixture of $C_5$ to $C_{11}$ paraffins. Butane could be reacted with a heavy paraffin stream ($C_{12+}$ paraffins) to form a mixture of $C_5$ to $C_{11+}$ paraffins.

One of the problems with renewable diesel fuel (about $C_{16}$) is that the feed for the process is limited and cannot meet current demand. Providing a route allowing more fuel to be produced from the diesel feed could be valuable. The present invention provides a method of increasing the fuel volume of the renewable diesel feed to $C_{5+}$ paraffins, which are components in gasoline. This can be accomplished by reacting the renewable diesel feed with one or more of methane, ethane, propane, or butane to form $C_{5+}$ paraffins at low temperatures and pressures. Alternatively, the renewable diesel feed could be reacted with a light paraffin stream, e.g., a $C_3$ to $C_6$ stream, to form a mixture of $C_{5+}$ paraffins. The fuel volume increases because the butanes (or methane, ethane, and/or propane) are incorporated into the $C_{5+}$ paraffins, resulting in an increase in the mass of the $C_{5+}$ fraction and a decrease in product density compared to the renewable diesel feed.

Another area where the present process can be used involves products of the Fischer-Tropsch process, which converts syngas ($H_2/CO$) into a hydrocarbon mixture, ideally in the diesel range. However, the process produces a large range of components, including Fischer-Tropsch wax, which are large paraffins (e.g., in the range of about 18 to 200 or more carbons) that are solid at room temperature and are undesirable. Typically, these compounds are hydrocracked to smaller fragments. These heavy compounds can be reacted with lighter paraffins, such as methane, ethane, propane, butane, or pentane, to produce a mixture of products having intermediate molecular weight, e.g., $C_{5+}$ paraffins. The mass of the $C_{5+}$ paraffins product is greater than the mass of the Fischer-Tropsch wax feed, and it has a density less than the density of the Fischer-Tropsch wax feed.

In some embodiments, the amount of $C_1$, $C_2$ and $C_3$ alkanes produced in the reaction may be very small. As a result, in some embodiments, these products may be ignored. Additionally, the maximal concentration of the $C_{n+1}$ and $C_{m-1}$ type compounds is set by the C/H molar ratio in the feed which may not allow for a high concentration of some species. For example, in some reactions that employ heavy paraffins (e.g. hexadecane) blended with smaller paraffins (e.g. butane), the amount of alkanes produced in the $C_{15}$ ($C_{m-1}$) region may be very small because the thermodynamic concentration of these species at the feed's total C/H molar ratio may be very small. As a result, in some embodiments, these products may be ignored.

Thus, reverse disproportionating two feeds where the first comprises $C_n$ and the second comprises $C_m$ will produce at least one product $C_z$ where n<z<m. There will typically be a range of products within the range: however, the amounts of some may be so small that they are not considered. For example, depending on the C/H ratio, reverse disproportionating two feeds where the first comprises $C_{1-4}$ and the second comprises $C_{5-12}$ will produce at least one product in the $C_{2-11}$ range. In some embodiments, the amounts of some of the products in that range may be so small as to be ignored. Similarly, reverse disproportionating $C_{1-9}$ and $C_{6-16}$ feeds will produce at least one product in the $C_{2-15}$ range. The amounts of some of those products may be so small as to be ignored. Reverse disproportionating $C_{1-10}$ and $C_{6-25}$ feeds will produce products in the $C_{2-24}$ range. The amounts of some products in the range may be so small as to be ignored. Reverse disproportionating $C_{1-23}$ and $C_{6-100}$ feeds will produce products in the $C_{2-99}$ range. The amounts of some of the products may be so small as to be ignored.

This process has a number of important advantages. The product composition would be tunable based on the ratio and compositions of the feeds. It is a low temperature, low pressure process. It uses ionic liquids that have similar acidity to those used in the alkylation process. It can be used to produce gasoline from butanes, and kerosene and diesel from gasoline. The reaction products are primarily isoparaffins, which would be beneficial for cloud point and octane.

Reactions involved in the tuning process include disproportionation, isomerization, and reverse disproportionation reactions. Reverse disproportionation feeds and reaction conditions are similar to those discussed below for isomerization and disproportionation reactions.

Disproportionation and/or isomerization of a hydrocarbon feed using a liquid catalyst comprising ionic liquids and carbocation promoters is described. The ionic liquids can be supported or unsupported and allow the reactions to occur at temperatures below about 200° C.

The disproportionation reaction involves contacting a hydrocarbon feed comprising a $C_n$ alkane with a liquid catalyst in a reaction zone to form a product mixture containing $C_{n-}$ alkanes and $C_{n+}$ alkanes. The liquid catalyst comprises an ionic liquid and a carbocation promoter, and n=2-200.

The isomerization reaction involves contacting the hydrocarbon feed comprising a normal $C_n$ alkane (or iso $C_n$ alkane) with a liquid catalyst in a reaction zone to form a product mixture containing iso $C_n$ alkanes (or normal $C_n$ alkanes). The liquid catalyst comprises an ionic liquid and a carbocation promoter, and wherein n=4-200.

Disproportionation and isomerization occur simultaneously. There is a substantial disproportionation reaction, which can be seen by the fact that significant amounts of $C_{n+}$ and $C_{n-}$ alkanes form. The product mixture can contain at least about 3 wt % $C_{n+}$ alkanes in 1 hr based on the $C_n$ alkane fraction in the hydrocarbon feed, or at least 5 wt %, or at least about 7 wt %, or at least about 10%, or at least about 15 wt %, or at least about 20 wt %. There is a corresponding formation of the $C_{n-}$ fraction. There can be at least about 3 wt % $C_{n-}$ alkanes in 1 hr based on the $C_n$ alkane fraction in the hydrocarbon feed, or at least 5 wt %, or at least about 7 wt %, or at least about 10%, or at least about 15 wt %, or at least about 20 wt %. The percentages are based on the $C_n$ alkane fraction in the hydrocarbon feed.

It is more complex to evaluate the $C_{n+}$ and $C_{n-}$ fractions when the feed comprises more than one $C_n$ alkane. When the feed comprises more than one $C_n$ alkane, the amount of $C_{n+}$ alkane based on the highest carbon number in the feed can be used. For example if, the feed comprises $C_5$ and $C_6$, the amount of $C_{n+}$ can be evaluated using the $C_7$ fraction. When the feed comprises $C_5$ and $C_5$, the increase may be evaluated using the $C_9$ fraction.

For a feed comprising $C_5$, at least about 5 wt % each of $C_{4-}$ and $C_{6+}$ forms within 30 min, or at least about 10 wt %, or at least about 15 wt %. At least about 10 wt % each of $C_{4-}$ and $C_{6+}$ forms within 1 hr, or at least about 15 wt %, or at least about 20 wt %.

For a feed comprising $C_7$, at least about 3 wt % each of $C_{6-}$ and $C_{8+}$ forms within 1 hr, or at least about 5 wt %, or at least about 7 wt %.

Another indication of the existence of the disproportionation reaction is that the number of moles in the product is nearly equal to the number of moles initially present.

There can also be a substantial isomerization reaction, which can be seen by the fact that significant amounts of iso $C_n$ alkanes form from normal $C_n$ alkanes, and normal $C_n$ alkanes form from iso $C_n$ alkanes initially. The product mixture can contain at least about 2 wt % normal $C_n$ alkanes in 1 hr based on the iso $C_n$ fraction in the hydrocarbon feed, or at least about 3 wt %, or at least 4 wt %, or at least about 5 wt %, or at least about 7 wt %, or at least about 10 wt %. The product mixture can contain at least about 5 wt % iso $C_n$ alkanes in 1 hr based on the normal $C_n$ fraction in the hydrocarbon feed, or at least about 10 wt %, or at least about 15 wt %, or at least about 20 wt %.

For normal $C_5$ isomerization, at least about 10 wt % of iso $C_5$ forms within 30 min, or at least about 15 wt %. At least about 15 wt % iso $C_5$ forms within 1 hr, or at least about 20 wt %.

For iso $C_5$ isomerization, at least about 2 wt % of normal $C_5$ forms within 1 hr min, or at least about 3 wt %, or at least about 4 wt %, or at least about 5 wt %.

For normal $C_7$ isomerization, at least about 5 wt % of iso $C_7$ forms within 1 hr, or at least about 10 wt %.

The conversion rate for volume can be calculated as volume rate=(% conversion/time (h))×(mL HC/mL IL), where the mL of IL is determined by taking the mass of the ionic liquid and carbocation promoter and dividing by the density of the pure ionic liquid. The conversion rate for volume is at least about 60 in the absence of an added metal salt, or at least about 70, or at least about 80, or at least about 90, or at least about 100, or at least about 120, or at least about 140, or at least about 160, or at least about 180, or at least about 200, or at least about 250, or at least about 300, or at least about 350, or at least about 400, or at least about 450, or at least about 500.

The conversion rate for mass can be calculated as mass rate=(% conversion/time (h))×(g HC/g IL), where the mass of the IL is taken to be the summed mass of the IL and carbocation promoter. The conversion rate for mass in the absence of a metal salt is at least about 20, or at least about 30, or at least about 40, or at least about 50, or at least about 60, or at least about 70, or at least about 80, or at least about 90, or at least about 100, or at least about 110, or at least about 120, or at least about 130, or at least about 140, or at least about 150, or at least about 175, or at least about 200, or at least about 220 or at least about 230, or at least about 240, or at least about 250, or at least about 250.

The present invention provides a method of disproportionating a hydrocarbon feed using less ionic liquid, which is expensive, and obtaining better results at a faster rate. It also provides a method of isomerizing a hydrocarbon feed using less ionic liquid, and obtaining better results at a faster rate.

The hydrocarbon feed can be straight chain paraffins, branched chain paraffins, cycloparaffins, naphthenes, or combinations thereof. The hydrocarbon feed may contain a single $C_n$ alkane, such as pentane, or mixtures of two or more alkanes, such as pentane and hexane, or pentane, hexane, and heptane.

In some embodiments, the hydrocarbon feed can be a mixture of 2, 3, 4, 5, or 6 or more consecutive carbon numbers. Typically, there will be one, two, or three carbon numbers that form most of the feed. For example, there could be greater than about 50% of one carbon number, or greater than about 60%, or greater than about 70%, or greater than about 80%. In some embodiments, two or three carbon numbers (or more) could form greater than about 50% of the feed, or greater than about 60%, or greater than about 70%, or greater than about 80%.

In some embodiments, the $C_n$ alkane can be substantially pure $C_n$ alkane e.g., greater than about 90% of a $C_n$ alkane, such as pentane, or greater than about 95%, or greater than about 97%, or greater than about 98%, or greater than about 99%.

In some embodiments, the $C_n$ alkane can be substantially pure normal $C_n$ alkane or substantially pure iso $C_n$ alkane, e.g., greater than about 90% of a specific normal or iso $C_n$ alkane, such as normal pentane, or greater than about 95%, or greater than about 97%, or greater than about 98%, or greater than about 99%.

In other embodiments, mixtures of normal $C_n$ alkane and iso $C_n$ alkane (both a single $C_n$ alkane, such as pentane, and two or more $C_n$ alkanes, such as pentane and hexane) are used. The ratio of normal $C_n$ alkane to iso $C_n$ alkane is typically in the range of about 90:10 to about 10:90, or about 80:20 to about 20:80, or about 70:30 to about 30:70, or about 60:40 to about 40:60, or about 50:50.

Figure 2:
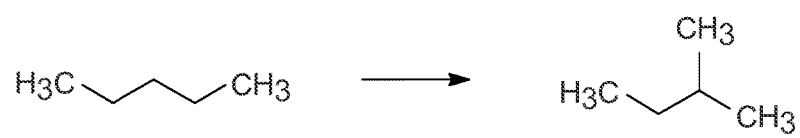
FIG. 2 illustrates the isomerization reaction of n-pentane.
Figure 3:
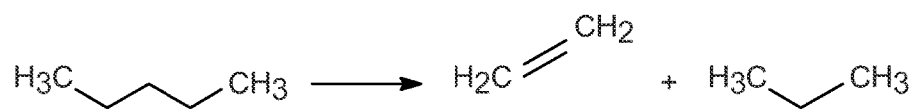
FIG. 3 illustrates a cracking reaction of n-pentane.
Figure 4:
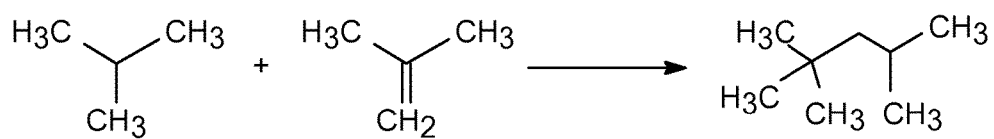
FIG. 4 illustrates an alkylation reaction of isobutane and isobutene.

As discussed above, the disproportionation reaction of a $C_n$ alkane produces $C_{n-}$ and $C_{n+}$ alkanes. For example, the disproportionation of $C_5$ produces $C_{4-}$ and $C_{6+}$ alkanes. The presence of the $C_{n+}$ fraction distinguishes the disproportionation reaction (FIG. 1) from isomerization reactions which produce isomers of the $C_n$ starting material (FIG. 2), or isomerization and cracking which produces isomers of the $C_n$ starting material and $C_{n-}$ alkanes due to cracking (FIGS. 2 and 3). The hydrocarbon feed can be dried to remove water before being contacted with the liquid catalyst. The feed can also be treated to remove undesirable reactive compounds such as alkenes, dienes, nitriles, and the like using known treatment processes.

The hydrocarbon feed can be a fluid. The fluid can be a liquid, a vapor, or a mixture of liquid and vapor. When a liquid or liquid-vapor mixture is used, the method is one of the few liquid-liquid disproportionation methods available.

The processes can produce mixtures of alkanes having desirable RVP and RON. The RVP and RON values are calculated on the $C_{5+}$ fraction. The RVP was calculated as the vapor pressure for the system when the vapor:liquid ratio is 4:1 by volume using the Peng Robinson fluid properties model. The RON was calculated with linear volumetric blending, and the RON values used for this calculation were based on the values listed in Phillips 66 Reference Data for Hydrocarbons and Petro-Sulfur Compounds. Bulletin No. 521.

In one embodiment, the product mixture of alkanes has an RVP in the range of about 1 to about 25, or about 8 to about 16, and an RON in a range of about 50 to about 110, or about 60 to about 100. In another embodiment, the product mixture of alkanes has a similar RVP and RON. The octane numbers can be increased by isomerization of the linear paraffins to the corresponding branched compounds.

In some embodiments, the RVP of the product mixture is less than the RVP of the hydrocarbon feed. In some embodiments, the RVP is reduced at least about 5 numbers compared to the hydrocarbon feed, or at least about 7 numbers, or at least about 8 numbers. For example, the RVP for pure (i.e., greater than 99%) normal pentane is 15.6, and the RVP for the product mixture made from substantially pure normal pentane is 13.0 to 13.5. The RVP for pure (i.e., greater than 99%) isopentane is 20.4, and the RVP for the product mixture made from substantially pure isopentane is 12.3 to 12.5.

When the mass ratio of branched alkanes to normal alkanes (i/n) produced from converted pentane feed is in the range of about 6:1 to about 17:1, the selectivity for isoparaffins is in the range of about 70 to about 90%, and when it is in the range of about 7:1 to about 17:1, the selectivity for isoparaffins is in the range of about 80 to about 90%. The high branched to normal ratios for alkanes obtainable with this system are notable, especially in comparison to the methods employing dehydrogenation and metathesis catalysts to effect disproportionation. Generally, when these catalysts are employed, the major isomers formed within the $C_{n-}$ and $C_{n+}$ systems are normal paraffins. The formation of large amounts of normal paraffins is typically not desired due to their low octane numbers.

The formula for calculating the i/n ratio of the product for pure alkanes is (wt. % $iC_{n-}$+x wt. % $iC_n$+wt. % $iC_{n+}$)/(wt. % $nC_{n-}$+y wt. % $nC_n$+wt. % $nC_{n+}$) with n− greater than or equal to 4, x=1 and y=0 when $C_n$=normal alkane and x=0 and y=1 when $C_n$=isoalkane. For example, for $C_5$, the calculation would be (wt. % $iC_4$+x wt. % $iC_5$+wt. % $iC_6$+wt. % $iC_7$+wt. % $iC_8$)/(wt. % $nC_4$+y wt. % $nC_5$+wt. % $nC_6$+wt. % $nC_7$+wt. % $nC_8$); where x=1 and y=0 when $C_n$=$nC_5$ and x=0 and y=1 when $C_n$ is $iC_5$). Although $C_{9+}$ alkanes will be present in small amounts, they should not substantially affect the i/n ratio as reported. In addition, the $C_{3-}$ compounds are not included because they don't have normal and iso isomers.

The lower reactivity of normal pentane ($nC_5$) has made it generally difficult to for the development of a commercial process using $nC_5$. However, disproportionation of $nC_5$ at reasonable rates has been demonstrated in more than one embodiment of the present invention.

In order for these reactions to proceed, a stable carbocation likely needs to be present. Carbocations readily undergo skeletal rearrangement at low temperatures. Even at −90° C. rapid rearrangement is observed for degenerate 1, 2-methide shifts. Frequently, carbocations are transient intermediates and are short-lived. However, persistent carbocations have been observed in superacidic media.

Ionic liquids offer a number of unique features which make them particularly well suited as reaction mediums for low temperature disproportionation and isomerization. These features include: (1) extremely low volatility, resulting in little to no solvent loss, (2) high chemical diversity, allowing for specific properties to be readily incorporated into the solvent, (3) good thermal stability, (4) readily recyclable, (5) wide liquid ranges, and (6) in some cases (e.g. 1-ethyl-3-methylimidazolium chloroahunminates), they have been shown to be superacidic.

In one embodiment, the liquid hydrocarbon feed comprises a $C_n$ alkane where n=5-200, or n=5-100, or n=5-50, or n=5-25, or n=5-12. A normal $C_n$ alkane is converted to a product mixture comprising iso $C_n$ hydrocarbons, normal and iso $C_{n-}$ hydrocarbons and normal and iso $C_{n+}$ hydrocarbons, and an iso $C_n$ alkane is converted to a product mixture comprising normal $C_n$ hydrocarbons, normal and iso $C_{n-}$ hydrocarbons and normal and iso $C_{n+}$ hydrocarbons. A blend of normal and iso $C_n$ alkane is converted to a product mixture comprising normal and iso $C_n$ hydrocarbons, normal and iso $C_{n-}$ hydrocarbons and normal and iso $C_{n+}$ hydrocarbons. In some embodiments, the highest concentration of $C_{n+}$ hydrocarbons is the $C_{n+1}$ hydrocarbon. For example, for a feed of n-pentane, the product mixture would be isopentane, $C_{4-}$ hydrocarbons and $C_{6+}$ hydrocarbons, and for a feed of isopentane, the product mixture would be n-pentane, $C_{4-}$ hydrocarbons and $C_{6+}$ hydrocarbons, with the highest concentration being $C_6$ hydrocarbons for the $C_{n+}$ fractions. A feed comprising a blend of n-pentane and isopentane would produce a product mixture of n-pentane and isopentane, $C_{4-}$ hydrocarbons and $C_{6+}$ hydrocarbons. The process is particularly useful for conversion of $C_5$, $C_6$, and $C_7$ alkanes.

The liquid catalyst comprises an ionic liquid and a carbocation promoter. The ionic liquid is in liquid form: unlike prior art processes, it is not supported on an oxide support. In addition, in some embodiments, the ionic liquids employed herein do not contain Brønsted acids, so the acid concentration within these systems is less than prior art processes using ionic liquids which are Brønsted acidic organic cations. The acid concentration is less than about 2.5 M, or less than about 2.25 M, or less than about 2.0 M, or less than about 1.75 M, or less than about 1.5 M. In other embodiments, the ionic liquids do contain Brønsted acids.

One or more ionic liquids can be used.

The ionic liquid comprises an organic cation and an anion. Suitable organic cations include, but are not limited to:

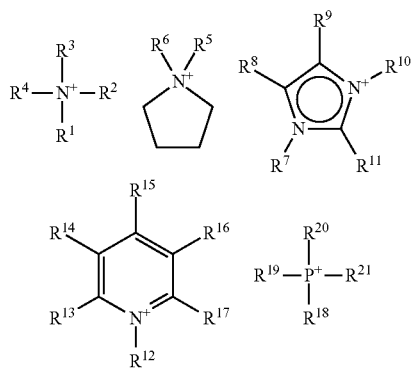

and lactamium based cations, where $R^1$-$R^{21}$ are independently selected from $C_1$-$C_{20}$ hydrocarbons, $C_1$-$C_{20}$ hydrocarbon derivatives, halogens, and H. Suitable hydrocarbons and hydrocarbon derivatives include saturated and unsaturated hydrocarbons, halogen substituted and partially substituted hydrocarbons and mixtures thereof. $C_1$-$C_5$ hydrocarbons are particularly suitable. Lactamium based ionic liquids include, but are not limited to, those described in U.S. Pat. No. 8,709,236. U.S. application Ser. No. 14/271,308, entitled Synthesis of Lactam Based Ionic Liquids, filed May 6, 2014, and U.S. application Ser. No. 14/271,319, entitled Synthesis of N-Derivatized Lactam Based Ionic Liquids, filed May 6, 2014, which are incorporated by reference.

The anion can be derived from halides, sulfates, bisulfates, nitrates, sulfonates, fluoroalkanesulfonates, and combinations thereof. The anion is typically derived from metal and nonmetal halides, such as metal and nonmetal chlorides, bromides, iodides, fluorides, or combinations thereof. Combinations of halides include, but are not limited to, mixtures of two or more metal or nonmetal halides (e.g., $AlCl_4^-$ and $BF_4^-$), and mixtures of two or more halides with a single metal or nonmetal (e.g. $AlCl_3Br^-$). In some embodiments, the metal is aluminum, with the mole fraction of aluminum ranging from 0<Al<0.25 in the anion. Suitable anions include, but are not limited to, $AlCl_4^-$, $Al_2Cl_7^-$, $Al_3Cl_{10}^-$, $AlCl_3Br^-$, $Al_2Cl_6Br^-$, $Al_3Cl_9Br^-$, $AlBr_4^-$, $Al_2Br_7^-$, $Al_3Br_{10}^-$, $GaCl_4^-$, $Ga_2Cl_7^-$, $Ga_3Cl_{10}^-$, $GaCl_3Br^-$, $Ga_2Cl_6Br^-$, $Ga_3Cl_9Br^-$, $CuCl_2^-$, $Cu_2Cl_3^-$, $Cu_3Cl_4^-$, $ZnCl_3^-$, $FeCl_3^-$, $FeCl_4^-$, $Fe_3Cl_7^-$, $PF_6^-$, and $BF_4^-$.

The ionic liquid is combined with one or more carbocation promoters. In some embodiments, the carbocation promoter is added to the ionic liquid. In other embodiments, the carbocation promoter is generated in situ.

Suitable carbocation promoters include, but are not limited to, halo-alkanes, mineral acids alone or combined with alkenes, and combinations thereof. Suitable halo-alkanes include but are not limited to 2-chloro-2-methylpropane, 2-chloropropane, 2-chlorobutane, 2-chloro-2-methylbutane, 2-chloropentane, 1-chlorohexane, 3-chloro-3-methylpentane, or combinations thereof. In some embodiments, the carbocation promoters are not cyclic alkanes.

Suitable mineral acids include, but are not limited to, HCl, HBr, $H_2SO_4$, and $HNO_3$. Although HF can also be used, it is less desirable due to safety issues. If the mineral acid is not strong enough to protonate off a hydrogen from a C—H bond, isobutene or another alkene can be added with the mineral acid to produce the desired carbocation promoter. The mineral acid can be generated in situ by the addition of a compound that reacts with the ionic liquid. In situ acid generation can also occur as a result of reaction with water present in the system. The mineral acid may also be present as an impurity in the ionic liquid.

2-chloropropane, and 2-chlorobutane were used successfully as carbocation promoters. HCl was generated in situ by the addition of methanol to the ionic liquid, resulting in the partial degradation of the $Al_2Cl_7^-$ anion with concomitant formation of HCl. This method was sufficient to catalyze the disproportionation.

The molar ratio of the carbocation promoter to the ionic liquid in the liquid catalyst is typically in the range of about 0:1 to about 3:1, or about 0.1:1 to about 1:1. This relates to forming the carbocation promoter from the halo-alkane or mineral acid. This ratio is important relative to the specific type of anion. For example, if the anion is $AlCl_4^-$, a reaction is unlikely to occur or will be poor because the aluminum is fully coordinated. However, if the anion is $Al_2Cl_7^-$, there is some aluminum present that can coordinate to the carbocation promoter's anion, assisting in generating the carbocation from the carbocation promoter.

The mass or volume ratios of liquid catalyst (ionic liquid and carbocation promoter) to hydrocarbon feed are less than 1:1. This is desirable because the ionic liquid is an expensive component in the process. In some embodiments, the mass ratio of ionic liquid to hydrocarbon feed is not more than about 0.75:1, or not more than about 0.7:1, or not more than about 0.65:1, or not more than about 0.60:1, or not more than about 0.55:1, or not more than about 0.50:1. In some embodiments, the volume ratio of ionic liquid to hydrocarbon feed is not more than about 0.8:1, or not more than about 0.7:1, or not more than about 0.6:1, or not more than about 0.5:1, or not more than about 0.45:1, or not more than about 0.4:1, or not more than about 0.35:1, or not more than about 0.3:1, or not more than about 0.25:1.

The liquid hydrocarbon feed is contacted with the liquid catalyst at temperatures of in the range of about −20° C. to the decomposition temperature of the ionic liquid, or about 250° C. or less, or about 200° C. or less, or about 175° C. or less, or about 150° C. or less, or about 125° C. or less, or about 100° C. or less, or about 90° C. or less, or about 80° C. or less, or about 70° C. or less, or about 60° C. or less, or in the range of about 0° C. to about 250° C., or in the range of about 0° C. to about 200° C., or about 0° C. to about 175° C., or about 0° C. to about 150° C., or about 10° (to about 150° C., or about 25° C. to about 15° C., or about 30° C. to about 150° C., or about 40° C. to about 150° C., or about 50° C. to about 150° C. or about 55° C. to about 150° C.

The pressure in the reaction zone is typically in the range of about 0 MPa to about 20.7 MPa, or about 0 MPa to about 8.1 MPa. In some embodiments, the pressure should be sufficient to ensure that the hydrocarbon feed is in a liquid state. Small amounts of vapor may also be present, but this should be minimized. In other embodiments, using propane and other light paraffins, the temperatures may not allow for a liquid state. In this gas, a gas phase or a supercritical phase can be used. In some embodiments, a supercritical phase can be used.

In some embodiments, the reaction zone operated at temperatures and or pressures greater than or equal to the critical temperature and pressure of the hydrocarbon feed, such as methane, propane, butanes, pentanes, and hexanes.

The reaction typically takes places in the presence of a gas. Suitable gases include, but are not limited to nitrogen, hydrogen, argon, helium, hydrogen chloride and the like.

The residence time in the reaction zone is generally less than about 10 hr, or less than 7 hr, or less than 5 hr, or less than 4 hr, or less than 3 hr, or less than 2 hr, or less than 1 hr. The reaction time and conversion are based on the time needed to reach equilibrium of the initial reaction products, such as 2-methylpentane and isobutane from the disproportionation of isopentane. The reaction time is a fiction of the degree of mixing, the reaction temperature, the concentration of the carbocation promoter, the molar ratio of the carbocation promoter to ionic liquid, and the mass/volume ratio of ionic liquid to hydrocarbon being reacted. Generally, increasing any of these conditions will increase the reaction rate. Under some conditions, greater than 90% conversion is possible.

The % selectivity for the disproportionation reaction is defined as: [(sum of the wt. % $C_{n-}$ and $C_{n+}$ compounds)/(100−wt. % $C_n$ feed)]×100. The % selectivity for the disproportionation reaction is typically at least about 40%, or at least about 45%, or at least about 50%, or at least about 55%, or at least about 60%, or at least about 65%, or at least about 70%, or at least about 75%, or at least about 80%, or at least about 85%, or at least about 90%, or at least about 94%.

For blends, the selectivity for the disproportionation reaction would be similar as above. For example, for a blend consisting of 50% isopentane and 50% n-pentane, the % selectivity for the disproportionation reaction is defined as: [(sum of the wt. % $C_4$— and $C_{6+}$ compounds)/(100−wt. % $C_n$ feed)]×100, where the $C_n$ feed is taken to be the summed wt. % of isopentane and n-pentane. A simple equation similar to this may not be adequate for more complex blends.

The % selectivity for the isomerization reaction to isoparaffins ($S_{iso\text{-}isom}$) is defined as (z(wt. % isoparaffin $C_n$))/(100−wt. % $C_n$ feed)×100, where z=0 when the $C_n$ feed is isoparaffin and z=1 when the $C_n$ feed is n-paraffin. The % selectivity for isoparaffin disproportionation is defined as (wt. % isoparaffins of $C_{n-}$+wt. % isoparaffins $C_{n+}$)/(100−wt. % $C_n$ feed)×100 ($S_{iso\text{-}disp}$). The % selectivity for isoparaffins is defined as (wt. % isoparaffins of $C_{n-}$+wt. % isoparaffins $C_{n+}$+z(wt. % isoparaffin $C_n$))/(100−wt. % $C_n$ feed)×100, where z=0 when the $C_n$ feed is isoparaffin and z=1 when the $C_n$ feed is n-paraffin ($S_{isoparaffin}$); or $S_{isoparaffin}=S_{iso\text{-}isom}+S_{iso\text{-}disp}$. The selectivity for isoparaffins is typically at least about 40%, or at least about 45%, or at least about 50%, or at least about 55%, or at least about 60%, or at least about 65%, or at least about 70%, or at least about 75%, or at least about 80%, or at least about 85%, or at least about 90%.

For blends, the selectivity for isoparaffins would be similar as above. For example, for a blend consisting of 50% isopentane and 50% n-pentane, the % selectivity for the isoparaffins reaction is defined as: [(sum of the wt. % $iC_4$ and $iC_{6+}$ compounds)/(100−wt. % $C_n$ feed)]×100, where the $C_n$ feed is taken to be the summed wt. % of isopentane and n-pentane. A simple equation similar to this may not be adequate for more complex blends.

The selectivity is highly dependent on the type of feed used. For example, for $iC_5$, the selectivity for the disproportionation reaction typically can be in the range of about 92-94%. However, the selectivity for the disproportionation reaction for $nC_5$ is much lower, e.g. in the range of about 67-76% because a substantial amount of isomerization to isopentane occurs.

Conversion for the disproportionation and isomerization reactions is defined as 100−wt. % $C_n$ feed. The conversion is typically at least about 50%, or at least about 55%, or at least about 60%, or at least about 65%, or at least about 70%, or at least about 75%, or at least about 80%, or at least about 85%, or at least about 90%.

For blends, the conversion would be the same as above. For example, for a blend consisting of 50% isopentane and 50% n-pentane, the % conversion is equal to 100−wt. % $C_n$ feed, where the $C_n$ feed taken to be the summed wt. % of isopentane and n-pentane.

For example, with an $iC_5$ feed, initially the products are primarily the isoparaffins of the $C_4$ and $C_6$ compounds along with some $nC_5$. Because $iC_5$ is more thermodynamically preferred, the amount of $nC_5$ that forms is relatively small, and the dominating pathway is disproportionation. Since the kinetic products are isoparaffins, the selectivity for isoparaffins can be similar to disproportionation. However, the mixture is not completely at equilibrium, so as the product continues to react, some of the initially formed isoparaffin of the disproportionation products begin to convert to their corresponding n-paraffins. As this occurs, the selectivity for isoparaffins decreases, but the selectivity for disproportionation does not.

With a feed of $nC_5$, the initial products are again primarily the isoparaffins of the $C_4$ and $C_6$ compounds and $iC_5$. Because $nC_5$ is thermodynamically disfavored the amount of $iC_5$ that forms is substantially greater relative to the formation of nC5 from the iC5 feed. In this case, significant amounts of $nC_5$ are converted to $iC_5$. Since the initial products are isoparaffins, the selectivity for isoparaffins remains high. However, since a significant portion of $nC_5$ is converted to $iC_5$, the selectivity for disproportionation is less than it was when $iC_5$ is used. As the reaction progresses, $iC_5$ and $nC_5$ continue to disproportionate and the selectivity for disproportionation increases during the reaction. Conversely, the selectivity for isoparaffins decreases as the mixture equilibrates because the initially formed isoparaffin disproportionation products convert to their normal isomers.

At higher temperatures, the relative concentration of normal paraffins increases, which ultimately results in decreased selectivities for isoparaffins relative to lower temperatures.

Although the reaction will proceed simply by contacting the hydrocarbon feed and the liquid catalyst, the reaction rate is generally too slow to be commercially viable. The reaction rate can be substantially increased by increasing the stirring speed of the reaction. This indicates that under some conditions the rate of reaction is mass transfer limited and is not reflective of the true elementary steps of the reaction. In addition to simply stirring the reaction mixture, a baffle can be included in the reactor to aid in obtaining good mixing. The baffle helps to prevent a vortex from forming in the reactor. The formation of a vortex would reduce the amount of mixing even in the presence of stirring.

Figure 5:
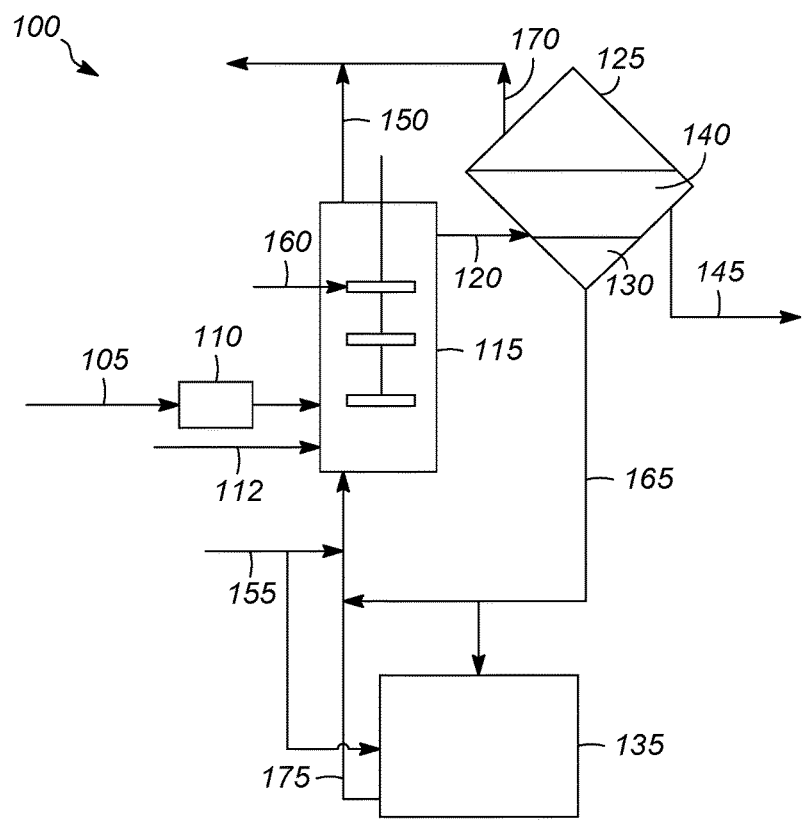
FIG. 5 is a schematic of one embodiment of the process of present invention.

One embodiment of the process 100 is a continuous-flow reactor as shown in FIG. 5. Feed 105, including the liquid hydrocarbon and carbocation promoter (if present), passes over a drying bed 110 and is continuously introduced to the reactor 115 while simultaneously withdrawing product 120. The liquid catalyst (or ionic liquid alone) 112 is introduced to the reactor 115. The carbocation promoter can be added with the hydrocarbon feed, or with the ionic liquid, or both. The reactor desirably includes a stirrer 160 to mix the hydrocarbon feed 105 and the liquid catalyst. The gaseous products 150 can be separated in the reactor 115. The effluent 120 is sent to a settler 125, where the heavier ionic liquid phase separates as a bottom layer 130. The used ionic liquid stream 165 can be recycled to the reactor 115 and/or the regenerator 135. The upper hydrocarbon layer phase 140 is removed from the settler 125, yielding the liquid product 145. The liquid product 145 can be separated into two or more product streams (not shown), if desired. The gaseous products 170 are separated in settler 125. These gaseous products 170 can be combined with gaseous products 150 which could then be used as feed in alkylation units (not shown). The used ionic liquid 165 can be regenerated in regenerator 135 to remove deactivated liquid catalyst so it can be reused. Fresh ionic liquid 155 can be added to the regenerated ionic liquid stream 175 as needed and sent to the reactor 115. Fresh ionic liquid can also be added to the regenerator 135, as needed.

Figure 6:
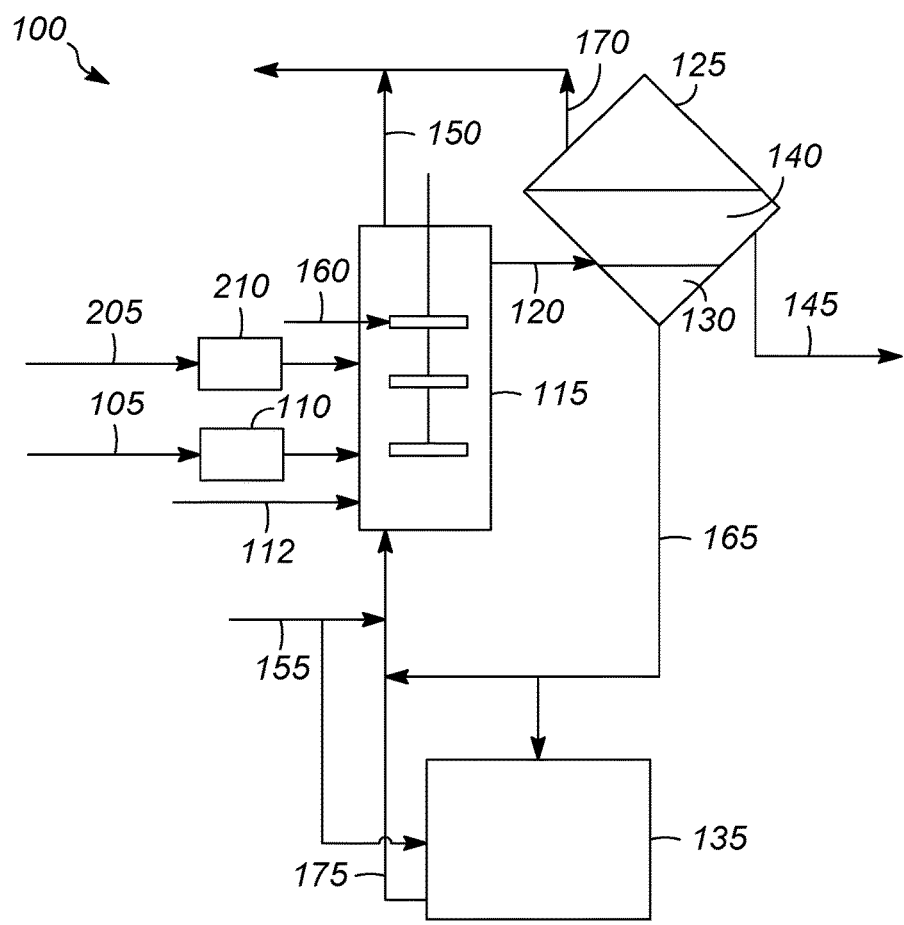
FIG. 6 is a schematic of one embodiment of the process of present invention.

Another embodiment of the process 100 is a continuous-flow reactor as shown in FIG. 6. A first feed 105, including the first hydrocarbon and carbocation promoter (if present), passes over a drying bed 110 and is continuously introduced to the reactor 115. The second feed 205, including the second hydrocarbon and promoter (if present) passes over drying bed 210 and is continuously introduced to the reactor 115. The product 120 is simultaneously withdrawn. The liquid catalyst (or ionic liquid alone) 112 is introduced to the reactor 115. The carbocation promoter can be added with the hydrocarbon feed, or with the ionic liquid, or both. The reactor desirably includes a stirrer 160 to mix the hydrocarbon feeds 105, 205 and the liquid catalyst. The gaseous products 150 can be separated in the reactor 115. The effluent 120 is sent to a settler 125, where the heavier ionic liquid phase separates as a bottom layer 130. The used ionic liquid stream 165 can be recycled to the reactor 115 and/or the regenerator 135. The upper hydrocarbon layer phase 140 is removed from the settler 125, yielding the liquid product 145. The liquid product 145 can be separated into two or more product streams (not shown), if desired. The gaseous products 170 are separated in settler 125. These gaseous products 170 can be combined with gaseous products 150 which could then be used as feed in alkylation units (not shown). The used ionic liquid 165 can be regenerated in regenerator 135 to remove deactivated liquid catalyst so it can be reused. Fresh ionic liquid 155 can be added to the regenerated ionic liquid stream 175 as needed and sent to the reactor 115. Fresh ionic liquid 155 can also be added to the regenerator 135, as needed.

The ionic liquid can be regenerated in a variety of ways. The ionic liquid containing the conjunct polymer could be contacted with a reducing metal (e.g., Al), an inert hydrocarbon (e.g., hexane), and hydrogen and heated to about 100° C. The conjunct polymer will be transferred to the hydrocarbon phase, allowing for the conjunct polymer to be removed from the ionic liquid phase. See e.g., U.S. Pat. No. 7,651,970: U.S. Pat. No. 7,825,055; U.S. Pat. No. 7,956,002; U.S. Pat. No. 7,732,363, each of which is incorporated herein by reference. Another method involves contacting the ionic liquid containing the conjunct polymer with a reducing metal (e.g., Al) in the presence of an inert hydrocarbon (e.g. hexane) and heating to about 100° C. The conjunct polymer will be transferred to the hydrocarbon phase, allowing for the conjunct polymer to be removed from the ionic liquid phase. See e.g., U.S. Pat. No. 7,674,739 B2; which is incorporated herein by reference. Still another method of regenerating the ionic liquid involves contacting the ionic liquid containing the conjunct polymer with a reducing metal (e.g., Al), HCl, and an inert hydrocarbon (e.g. hexane), and heating to about 100° C. The conjunct polymer will be transferred to the hydrocarbon phase, allowing for the conjunct polymer to be removed from the IL phase. See e.g., U.S. Pat. No. 7,727,925, which is incorporated herein by reference. The ionic liquid can be regenerated by adding a homogeneous metal hydrogenation catalyst (e.g., $(PPh_3)_3RhCl$) to the ionic liquid containing the conjunct polymer and an inert hydrocarbon (e.g. hexane). Hydrogen would be introduced, and the conjunct polymer would be reduced and transferred to the hydrocarbon layer. See e.g., U.S. Pat. No. 7,678,727, which is incorporated herein by reference. Another method for regenerating the ionic liquid involves adding HCl, isobutane, and an inert hydrocarbon to the ionic liquid containing the conjunct polymer and heating to about 100° C. The conjunct polymer would react to form an uncharged complex, which would transfer to the hydrocarbon phase. See e.g., U.S. Pat. No. 7,674,740, which is incorporated herein by reference. The ionic liquid could also be regenerated by adding a supported metal hydrogenation catalyst (e.g. Pd/C) to the ionic liquid containing the conjunct polymer and an inert hydrocarbon (e.g. hexane). Hydrogen would be introduced and the conjunct polymer would be reduced and transferred to the hydrocarbon layer. See e.g., U.S. Pat. No. 7,691,771, which is incorporated herein by reference. Still another method involves adding a suitable substrate (e.g. pyridine) to the ionic liquid containing the conjunct polymer. After a period of time, an inert hydrocarbon would be added to wash away the liberated conjunct polymer. The ionic liquid precursor [butylpyridinium][Cl] would be added to the ionic liquid (e.g. [butylpyridinium][$Al_2Cl_7$]) containing the conjunct polymer followed by an inert hydrocarbon. After a given time of mixing, the hydrocarbon layer would be separated, resulting in a regenerated ionic liquid. See, e.g., U.S. Pat. No. 7,737,067, which is incorporated herein by reference. Another method involves adding the ionic liquid containing the conjunct polymer to a suitable substrate (e.g. pyridine) and an electrochemical cell containing two aluminum electrodes and an inert hydrocarbon. A voltage would be applied and the current measured to determine the extent of reduction. After a given time, the inert hydrocarbon would be separated, resulting in a regenerated ionic liquid. See, e.g., U.S. Pat. No. 8,524,623, which is incorporated herein by reference.

The contacting step may be practiced in laboratory scale experiments through full scale commercial operations. The process may be operated in batch, continuous, or semi-continuous mode. The contacting step can take place in various ways, with both concurrent and co-current flow processes being suitable.

Disproportionation of $nC_5$ and $iC_5$ has also been achieved at temperatures as low as 45° C. The reaction was faster with $iC_5$ than with $nC_5$. Gas chromatograph (GC) analysis revealed that the primary compounds formed were isoparaffins using the analytical method ASTM UOP690-99; very few $C_{3-}$ hydrocarbons formed. The products of the reaction for n-$C_5$ were broadly divided into the following categories: $C_{3-}$, n-$C_4$, $iC_4$, $iC_5$, $C_6$ paraffins ($C_6P$) and $C_{7+}$ hydrocarbons. The products of the reaction for iso $C_5$ were broadly divided into the following categories: $C_{3-}$, n-$C_4$, $iC_4$, $nC_5$, $C_6$ paraffins ($C_6P$) and $C_{7+}$ hydrocarbons. The selectivity to these products was constant over a wide range of isopentane conversions. However, at higher conversions, the selectivity to $C_6$ paraffins decreased, while the selectivity to $iC_4$ and $C_{7+}$ hydrocarbons increased, which is likely the result of secondary disproportionation-type reactions. An analysis of both the headspace and the liquid phase revealed that $C_{3-}$ hydrocarbons form in small amounts.

In some places, demand for $iC_4$ exceeds supply, and disproportionation could help alleviate this problem.

For iso-pentane conversion, the selectivity to the various products (product selectivity being defined as [wt. % compound/(100−wt. % $C_n$ feed)]*100) was nearly constant up to about 52% conversion at 55° C. Higher isopentane conversions resulted in decreased selectivity to $C_6$ paraffins and higher selectivities to $iC_4$ and $C_{7+}$ hydrocarbons, which was likely the result of secondary disproportionation-type reactions.

With iso-pentane conversion, the extent of isomerization to n-pentane was minimal, but observable, because the reactant was already present in the more thermodynamically favored state. It was consistently observed that the selectivity for isomerization of isopentane to n-pentane centered around 7%, regardless of the % conversion of isopentane.

A significant stir rate dependence on the reaction rate was observed. Under the conditions used, the benefits of increased mixing began to taper off at stir rates greater than 700 rpm, which indicates that much of the kinetics of the reaction below 700 rpm is mass transfer limited.

The other products that form during the disproportionation reaction of isopentane were mainly isobutane and $C_{6+}$ isoparaffins. The selectivity to these products was also nearly constant with isopentane conversion. However, at higher conversions, the selectivity to the $C_6$ paraffins decreased, while there was a concomitant increase in selectivity for isobutane and $C_{7+}$ isoparaffins. It is important to note that very little $C_{3-}$ formed in the reactions at 55° C. as revealed by a headspace analysis and by the analytical method ASTM UOP980-07.

Under similar conditions (e.g., volume of ionic liquid, temperature, stir rate, etc.), the rate of $nC_5$ conversion is dependent on the type of ionic liquid used, as the same reaction proceeds at a much greater conversion rate in [1-butyl-1-methylpyrrolidinium][$Al_2C_7$] than in [tributyl(hexyl)phosphonium][$Al_2Cl_6Br$] ([("Bu)_3P(Hex)][$Al_2Cl_6Br$]). Despite the increase in reactivity, the selectivities for the products were similar to what was observed with the ionic liquid [("Bu)_3P(Hex)][$Al_2Cl_6Br$].

Isomerization and disproportionation of n-hexane has been found to occur at temperatures as low as 45° C. in several different ionic liquids (e.g. [("Bu)_3P(Hex)][$Al_2Cl_6Br$], [1-butyl-1-methylpyrrolidinium][$Al_2Cl_7$], [1-butyl-3-methylimidazolium][$Al_2Cl_7$] and trihexyl(tetradecyl)phosphonium heptachloroaluminate ([(n-Hex)_3P(tetradecyl)][$Al_2Cl_7$])). The promoter used in all of these reactions, except for [1-butyl-3-methylimidazolium][$Al_2Cl_7$], was 2-chloro-2-methylpropane, which served to generate the active tert-butyl cation. Trace amounts of water or HCl present in [1-butyl-3-methylimidazolium][$Al_2Cl_7$] was sufficient for the catalysis to occur. A wide range of compounds were formed, including naphthenes, n-paraffins, isoparaffins and even some aromatic complexes, but the major products are paraffins.

Increasing the concentration of 2-chloro-2-methylpropane increased the conversion, and the yield for the higher and lighter molecular weight complexes. The major light components formed were identified by headspace analysis as $iC_4$, $iC_5$, 2-methylpentane and unreacted $nC_6$. However, it did little to change the selectivity for isomerization. Similarly, increasing the reaction time, temperature, and ratio of mass of ionic liquid to mass of hydrocarbon feed increased the overall conversion. It is desirable to minimize the amount of ionic liquid used due to the cost and potential increase in the amount of feed processed per unit ionic liquid.

By the term "about," we mean within 10% of the value, or within 5%, or within 1%.

EXAMPLES

Example 1: Experimental Set Up

The set-up included a 300 mL autoclave equipped with a mechanical stirrer, pressure gauge, thermocouple, dipleg, rupture disc and valves to introduce the feed and withdraw an aliquot for GC analysis. The rupture disc vented to a knock out pot. The house nitrogen passed through a pressure regulator to a high surface sodium column and was then split: feeding to the charger for feed introduction or to a line for various uses (i.e., 2-methyl-2-chloropropane/$C_5P$ introduction). The dipleg was constructed such that the height positions it in the paraffin layer. Upon opening the valve, the withdrawn paraffin layer passed through a column of silica, to the GC valve and then through a metering valve into a waste container. The reaction mixture was analyzed using the ASTM UOP690-99 method. The $S_{isoparaffin}$ was calculated by summing the wt. % contribution of the C4-C8 isoparaffins that are separable using the ASTM UOP690-99 method, but does not include the contributions from the C9+ fraction. Consequently, these values represent lower limits for the selectivity. Similarly, the $S_{iso-disp}$ were determined using this analytical method and is also a lower limit. The RVP was calculated on the $C_{5+}$ fraction as the vapor pressure for the system when the vapor:liquid ratio is 4:1 by volume using the Peng Robinson fluid properties model. The RON was calculated on the $C_{5+}$ fraction with linear volumetric blending and the RON values used for this calculation were based on the values listed in Phillips 66 Reference Data for Hydrocarbons and Petro-Sulfur Compounds. Bulletin No. 521.

Example 2: Synthesis of [("Bu)_3P(Hex)][$Al_2Cl_6Br$]

An oven-dried round bottom flask was charged with [("Bu)_3P(Hex)][Br]. The material was attached to a rotary evaporator and dried under vacuum at 110° C. for at least 14 h. The dried [("Bu)$_3$P(Hex)][Br] was immediately brought into a nitrogen glovebox and stored there. A synthesis was achieved by massing 17.589 g (47.88 mmol) of [("Bu)$_3$P (Hex)][Br] into an oven-dried flask equipped with a stir bar in the nitrogen glovebox. To this was added 12.775 g (95.81 mmol) of AlCl$_3$ at ambient temperature. The mixture was stirred and the solids slowly reacted over the course of one week to produce a homogenous pale-yellow liquid.

Example 3: Synthesis of [1-butyl-1-methylpyrrolidinium][Al$_2$Cl$_7$]

An oven-dried round bottom flask was charged with [1-butyl-1-methylpyrrolidinium][C]. The material was attached to a rotary evaporator, dried under vacuum at 110° C. for at least 14 h, and then sealed under vacuum with a connecting adapter. The dried [1-butyl-1-methylpyrrolidinium][Cl] was immediately brought into a nitrogen glovebox and stored there. A synthesis was achieved by massing 57.14 g (322 mmol) of [1-butyl-1-methylpyrrolidinium][Cl] into an oven-dried flask equipped with a stir bar in the nitrogen glovebox. To this was added 83.93 g (629 mmol) of AlCl$_3$ at ambient temperature and the mixture stirred. The solids reacted to produce a homogenous liquid.

Example 4: Synthesis of with [1-butyl-3-methylimidazolium][Al$_2$Cl$_7$]

An oven-dried round bottom flask was charged with 1-butyl-3-methylimidazolium chloride. The material was attached to a rotary evaporator, dried under vacuum at 110° C. for at least 14 h and then sealed under vacuum with a connecting adapter. Afterwards, the dried 1-butyl-3-methylimidazolium chloride was stored in a nitrogen glovebox. A synthesis was achieved by massing 50.04 g (286 mmol) of 1-butyl-3-methylimidazolium chloride into an oven-dried flask equipped with a stir bar in the nitrogen glovebox. To this was added 76.40 g (573 mmol) of AlCl$_3$ at ambient temperature, and the mixture stirred. The solids react to produce a homogenous liquid.

Example 5: iC$_5$—Stir Rate Effect at 350 rpm with [("Bu)$_3$P(Hex)][Al$_2$Cl$_6$Br]

A 300 mL stainless steel autoclave, stainless steel baffle, and 75 mL stainless steel sample cylinder were dried in a 120° (oven for at least 8 h. The dried autoclave and sample cylinder were brought into a nitrogen glovebox and allowed to cool to ambient temperature. The autoclave was charged with 50.39 g of [("Bu)$_3$P(Hex)][Al$_2$Cl$_6$Br], and the autoclave head was attached. To the sample cylinder, 1.451 g of 2-chloro-2-methylpropane, which had previously been dried over activated sieves, was added. The sample cylinder was closed under nitrogen, and both the autoclave and sample cylinder were removed from the glovebox. The autoclave was charged with 119 g of iso-pentane from a pressurized feed charger without displacing the nitrogen present in the autoclave. The iso-pentane passed over a high surface sodium column to remove any water before entering the autoclave. Similarly, the nitrogen used to pressurize the charger and for all other work passed over a separate high surface sodium column. The sample cylinder was charged with 18 g of iso-pentane using the same method described above and attached to the autoclave. The autoclave was heated to 55° C. and the 2-chloro-2-methylpropane/iso-pentane solution in the sample cylinder was added with an over-pressure of nitrogen. After complete addition, the initial pressure in the autoclave was 145 psi (1 MPa), and the autoclave was then set to stir at 350 rpm. The reaction was monitored periodically by GC. In order to analyze the paraffinic layer, the stirring was stopped, and the product was allowed to settle for 5 minutes. An aliquot was sampled directly from the autoclave by opening a valve from the autoclave, passing the paraffinic layer through a SiO$_2$ column, and then passing it directly into a GC sample loop. The mass ratio of liquid catalyst to iso-pentane was 0.38 and the volume ratio was 0.19. The mass rate of reaction was 38, and the volume rate was 75 after 1.4 h. The results of the run are shown in Tables 1 and 2.

TABLE 1

Disproportionation and Isomerization of iso-Pentane at 55° C., 350 rpm wt. % of reaction mixture

| t (h) | % Conv. | C3– | iC4 | nC4 | iC5 | nC5 | C6P | C7+ | i/n | S. Disp. | S$_{isoparaffin}$ |
|---|---|---|---|---|---|---|---|---|---|---|---|
| 1.4 | 20 | 0.00 | 7.20 | 0.02 | 80.46 | 1.31 | 6.84 | 4.13 | 11.2 | 93 | 82 |
| 2.7 | 28 | 0.01 | 10.38 | 0.04 | 72.48 | 2.04 | 9.93 | 5.09 | 9.94 | 92 | 84 |
| 4.4 | 36 | 0.01 | 13.64 | 0.07 | 64.29 | 2.70 | 12.75 | 6.54 | 9.48 | 92 | 85 |

TABLE 2

Disproportionation and Isomerization of iso-Pentane at 55° C. 350 rpm, wt. % of reaction mixture

| Time (h) | 1.4 | 2.7 | 4.4 | NA |
|---|---|---|---|---|
| Wt. % | | | | feed |
| C3P | 0.00 | 0.01 | 0.01 | 0.00 |
| C4P | 7.22 | 10.43 | 13.71 | 0.00 |
| C5P | 81.77 | 74.53 | 66.99 | 99.86 |
| C6P | 6.84 | 9.94 | 12.74 | 0.00 |
| C7P | 1.67 | 2.47 | 3.32 | 0.00 |
| C8P | 0.52 | 0.73 | 1.00 | 0.00 |
| C9+ | 1.56 | 1.51 | 1.80 | 0.00 |
| C5N | 0.00 | 0.00 | 0.00 | 0.00 |
| C6N | 0.00 | 0.00 | 0.00 | 0.00 |
| C7N | 0.01 | 0.00 | 0.00 | 0.00 |
| C8N | 0.34 | 0.34 | 0.38 | 0.00 |
| C6A | 0.00 | 0.00 | 0.00 | 0.00 |
| C7A | 0.00 | 0.00 | 0.00 | 0.00 |
| C8A | 0.05 | 0.05 | 0.05 | 0.00 |
| nC4-nC5 unknowns | 0.00 | 0.00 | 0.00 | 0.14 |
| mmoles (based on wt. %) | | | | |
| C3P | 0 | 0 | 0 | 0 |
| C4P | 124 | 179 | 236 | 0 |
| C5P | 1133 | 1033 | 928 | 1384 |
| C6P | 79 | 115 | 148 | 0 |
| C7P | 17 | 25 | 33 | 0 |
| C8P | 5 | 6 | 9 | 0 |
| C9+ | 12 | 12 | 14 | 0 |

TABLE 2-continued

Disproportionation and Isomerization of iso-Pentane at 55° C. 350 rpm, wt. % of reaction mixture

| Time (h) | 1.4 | 2.7 | 4.4 | NA |
|---|---|---|---|---|
| C5N | 0 | 0 | 0 | 0 |
| C6N | 0 | 0 | 0 | 0 |
| C7N | 0 | 0 | 0 | 0 |
| C8N | 3 | 3 | 3 | 0 |
| C6A | 0 | 0 | 0 | 0 |
| C7A | 0 | 0 | 0 | 0 |
| C8A | 0 | 0 | 1 | 0 |
| nC4-nC5 unknowns | 0 | 0 | 0 | 2 |
| Total mmoles | 1374 | 1374 | 1372 | 1386 |

Example 6: iC5—Stir Rate Effect at 700 rpm with [(″Bu)$_3$P(Hex)][Al$_2$Cl$_6$Br]

A 300 mL stainless steel autoclave, stainless steel baffle, and 75 mL stainless steel sample cylinder were dried in a 120° C. oven for at least 8 h. The dried autoclave and sample cylinder were brought into a nitrogen glovebox and allowed to cool to ambient temperature. The autoclave was charged with 50.352 g of [(″Bu)$_3$P(Hex)][Al$_2$Cl$_6$Br], and the autoclave head was attached. To the sample cylinder, 1.453 g of 2-chloro-2-methylpropane, which had previously been dried over activated sieves, was added. The sample cylinder was closed under nitrogen, and both the autoclave and sample cylinder were removed from the glovebox. The autoclave was charged with 112 g of iso-pentane from a pressurized feed charger without displacing the nitrogen present in the autoclave. The iso-pentane passed over a high surface sodium column to remove any water before entering the autoclave. Similarly, the nitrogen used to pressurize the charger and for all other work passed over a separate high surface sodium column. The sample cylinder was charged with 15 g of iso-pentane using the same method described above and attached to the autoclave. The autoclave was heated to 55° C., and the 2-chloro-2-methylpropane/iso-pentane solution in the sample cylinder was added with an over-pressure of nitrogen. After complete addition, the initial pressure in the autoclave was 115 psi (0.793 MPa), and the autoclave was then set to stir at 700 rpm. The reaction was monitored periodically by GC. In order to analyze the paraffinic layer, the stirring was stopped, and the product was allowed to settle for 5 minutes. An aliquot was sampled directly from the autoclave by opening a valve from the autoclave, passing the paraffinic layer through a SiO$_2$ column, and then passing it directly into a GC sample loop. The mass ratio of liquid catalyst to iso-pentane was 0.40 and the volume ratio was 0.20. The mass rate of reaction was 47, and the volume rate was 93 after 1.5 h. The results of the run are shown in Tables 3 and 4.

TABLE 3

Disproportionation and Isomerization of iso-Pentane at 55° C., 700 rpm, wt. % of reaction mixture

| t (h) | % Conv. | C3− | iC4 | nC4 | iC5 | nC5 | C6P | C7+ | i/n | S. Disp. | S$_{isoparaffin}$ |
|---|---|---|---|---|---|---|---|---|---|---|---|
| 1.5 | 28 | 0.02 | 10.35 | 0.04 | 72.07 | 1.94 | 9.83 | 5.74 | 10.5 | 93 | 83 |
| 2.7 | 39 | 0.02 | 14.84 | 0.10 | 61.22 | 2.82 | 13.35 | 7.65 | 9.5 | 93 | 84 |
| 4.4 | 52 | 0.03 | 20.18 | 0.18 | 47.98 | 3.66 | 16.71 | 11.25 | 9.1 | 93 | 84 |

TABLE 4

Disproportionation and Isomerization of iso-Pentane at 55° C. 700 rpm, wt. % of reaction mixture

| Time (h) | 1.5 | 2.7 | 4.4 | NA |
|---|---|---|---|---|
| Wt. % | | | | feed |
| C3P | 0.02 | 0.02 | 0.03 | 0.00 |
| C4P | 10.39 | 14.93 | 20.35 | 0.00 |
| C5P | 74.02 | 64.05 | 51.64 | 99.86 |
| C6P | 9.83 | 13.34 | 16.71 | 0.00 |
| C7P | 2.55 | 3.79 | 5.53 | 0.00 |
| C8P | 0.82 | 1.25 | 1.99 | 0.00 |
| C9+ | 1.99 | 2.17 | 3.13 | 0.00 |
| C5N | 0.00 | 0.00 | 0.00 | 0.00 |
| C6N | 0.00 | 0.00 | 0.00 | 0.00 |
| C7N | 0.00 | 0.01 | 0.01 | 0.00 |
| C8N | 0.33 | 0.37 | 0.51 | 0.00 |
| C6A | 0.00 | 0.00 | 0.00 | 0.00 |
| C7A | 0.00 | 0.00 | 0.01 | 0.00 |
| C8A | 0.06 | 0.06 | 0.09 | 0.00 |
| nC4-nC5 unknowns | 0.00 | 0.00 | 0.00 | 0.14 |
| mmoles (based on wt. %) | | | | |
| C3P | 0 | 0 | 1 | 0 |
| C4P | 179 | 257 | 350 | 0 |
| C5P | 1026 | 888 | 716 | 1384 |
| C6P | 114 | 155 | 194 | 0 |
| C7P | 25 | 38 | 55 | 0 |
| C8P | 7 | 11 | 17 | 0 |
| C9+ | 16 | 17 | 24 | 0 |
| C5N | 0 | 0 | 0 | 0 |
| C6N | 0 | 0 | 0 | 0 |
| C7N | 0 | 0 | 0 | 0 |
| C8N | 3 | 3 | 5 | 0 |
| C6A | 0 | 0 | 0 | 0 |
| C7A | 0 | 0 | 0 | 0 |
| C8A | 1 | 1 | 1 | 0 |
| nC4-nC5 unknowns | 0 | 0 | 0 | 2 |
| Total mmoles | 1371 | 1370 | 1363 | 1386 |

Example 7: iC5—Stir Rate Effect at 1700 rpm with [(″Bu)$_3$P(Hex)][Al$_2$Cl$_6$Br]

A 300 mL stainless steel autoclave, stainless steel baffle, and 75 mL stainless steel sample cylinder were dried in a 120° C. oven for at least 8 h. The dried autoclave and sample cylinder were brought into a nitrogen glovebox and allowed to cool to ambient temperature. The autoclave was charged with 50.398 g of [(″Bu)$_3$P(Hex)][Al$_2$Cl$_6$Br], and the autoclave head was attached. To the sample cylinder 1.453 g of 2-chloro-2-methylpropane, which had previously been dried over activated sieves, was added. The sample cylinder was closed under nitrogen, and both the autoclave and sample cylinder were removed from the glovebox. The autoclave was charged with 106 g of iso-pentane from a pressurized feed charger without displacing the nitrogen present in the autoclave. The iso-pentane passed over a high surface sodium column to remove any water before entering the autoclave. Similarly, the nitrogen used to pressurize the charger and for all other work passed over a separate high surface sodium column. The sample cylinder was charged with 23 g of iso-pentane using the same method described above and attached to the autoclave. The autoclave was heated to 55° C., and the 2-chloro-2-methylpropane/iso-pentane solution in the sample cylinder was added with an over-pressure of nitrogen. After complete addition, the initial pressure in the autoclave was 139 psi (0.958 MPa), and the autoclave was set to stir at 1700 rpm. The reaction was monitored periodically by GC. In order to analyze the paraffinic layer, the stirring was stopped, and the product was allowed to settle for 5 minutes. An aliquot was sampled directly from the autoclave by opening a valve from the autoclave, passing the paraffinic layer through a $SiO_2$ column, and then passing it directly into a GC sample loop. The mass ratio of liquid catalyst to iso-pentane was 0.40 and the volume ratio was 0.20. The mass rate of reaction was 41, and the volume rate was 82 after 2.5 h. The results of the run are shown in Tables 5 and 6.

TABLE 5

Disproportionation and Isomerization of iso-Pentane at 55° C., 1700 rpm, wt. % of reaction mixture

| t (h) | % Conv. | C3− | iC4 | nC4 | iC5 | nC5 | C6P | C7+ | i/n | S. Disp. | $S_{isoparaffin}$ |
|---|---|---|---|---|---|---|---|---|---|---|---|
| 2.5 | 41 | 0.01 | 15.70 | 0.13 | 58.64 | 2.94 | 14.48 | 8.09 | 9.6 | 93 | 84 |
| 3.7 | 49 | 0.02 | 19.55 | 0.19 | 50.66 | 3.51 | 16.73 | 9.34 | 9.3 | 93 | 85 |

TABLE 6

Disproportionation and Isomerization of iso-Pentane at 55° C. 1700 rpm, wt. % of reaction mixture

| Time (h) | 2.5 | 3.7 | NA |
|---|---|---|---|
| Wt. % | | | feed |
| C3P | 0.01 | 0.02 | 0.00 |
| C4P | 15.83 | 19.74 | 0.00 |
| C5P | 61.58 | 54.17 | 99.86 |
| C6P | 14.48 | 16.73 | 0.00 |
| C7P | 4.06 | 4.97 | 0.00 |
| C8P | 1.31 | 1.59 | 0.00 |
| C9+ | 2.30 | 2.33 | 0.00 |
| C5N | 0.00 | 0.00 | 0.00 |
| C6N | 0.00 | 0.00 | 0.00 |
| C7N | 0.01 | 0.00 | 0.00 |
| C8N | 0.36 | 0.39 | 0.00 |
| C6A | 0.00 | 0.00 | 0.00 |
| C7A | 0.00 | 0.01 | 0.00 |
| C8A | 0.06 | 0.07 | 0.00 |
| nC4-nC5 unknowns | 0.00 | 0.00 | 0.14 |
| mmoles (based on wt. %) | | | |
| C3P | 0 | 0 | 0 |
| C4P | 272 | 340 | 0 |
| C5P | 854 | 751 | 1384 |
| C6P | 168 | 194 | 0 |
| C7P | 41 | 50 | 0 |
| C8P | 11 | 14 | 0 |
| C9+ | 18 | 18 | 0 |
| C5N | 0 | 0 | 0 |
| C6N | 0 | 0 | 0 |
| C7N | 0 | 0 | 0 |
| C8N | 3 | 3 | 0 |
| C6A | 0 | 0 | 0 |
| C7A | 0 | 0 | 0 |
| C8A | 1 | 1 | 0 |
| nC4-nC5 unknowns | 0 | 0 | 2 |
| Total mmoles | 1368 | 1371 | 1386 |

Example 8: iC5—Stir Rate at 700 rpm with [("Bu)$_3$P(Hex)][Al$_2$Cl$_6$Br] in Hastelloy C Autoclave at 55° C.

A 300 mL Hastelloy C autoclave. Hastelloy C baffle, and 75 mL stainless steel sample cylinder were dried in a 120° C. oven for at least 8 h. The dried autoclave and sample cylinder were brought into a nitrogen glovebox and allowed to cool to ambient temperature. The autoclave was charged with 50.416 g of [("Bu)$_3$P(Hex)][Al$_2$Cl$_6$Br], and the autoclave head was attached. To the sample cylinder 1.422 g of 2-chloro-2-methylpropane, which had previously been dried over activated sieves, was added. The sample cylinder was closed under nitrogen, and both the autoclave and sample cylinder were removed from the glovebox. The autoclave was charged with 114 g of iso-pentane from a pressurized feed charger without displacing the nitrogen present in the autoclave. The iso-pentane passed over a high surface sodium column to remove any water before entering the autoclave. Similarly, the nitrogen used to pressurize the charger and for all other work passed over a separate high surface sodium column. The sample cylinder was charged with 16 g of iso-pentane using the same method described above and attached to the autoclave. The autoclave was heated to 55° C., and the 2-chloro-2-methylpropane/iso-pentane solution in the sample cylinder was added with an over-pressure of nitrogen. After complete addition, the initial pressure in the autoclave was 140 psi (0.965 MPa), and the autoclave was set to stir at 700 rpm. The reaction was monitored periodically by GC. In order to analyze the paraffinic layer, the stirring was stopped, and the product was allowed to settle for 5 minutes. An aliquot was sampled directly from the autoclave by opening a valve from the autoclave, passing the paraffinic layer through a $SiO_2$ column, and then passing it directly into a GC sample loop. The mass ratio of liquid catalyst to iso-pentane was 0.40 and the volume ratio was 0.20. The mass rate of reaction was 70, and the volume rate was 140 after 0.5 h. The results of the run are shown in Tables 7 and 8.

TABLE 7

Disproportionation and Isomerization of iso-Pentane at 55° C., 700 rpm, Hastelloy C autoclave, wt. % of reaction mixture

| t (h) | % Conv. | C3− | iC4 | nC4 | iC5 | nC5 | C6F | C7+ | i/n | S. Disp. | $S_{isoparaffin}$ |
|---|---|---|---|---|---|---|---|---|---|---|---|
| 0.5 | 14 | 0.00 | 5.04 | 0.01 | 85.85 | 0.94 | 4.98 | 3.16 | 11.4 | 93 | 82 |
| 2.8 | 38 | 0.14 | 14.04 | 0.11 | 62.48 | 3.13 | 12.89 | 7.08 | 8.1 | 92 | 83 |
| 4.5 | 54 | 0.03 | 20.70 | 0.25 | 46.32 | 4.41 | 16.82 | 11.45 | 7.6 | 92 | 82 |

TABLE 8

Disproportionation and Isomerization of iso-Pentane at 55° C. 700 rpm, Hastelloy C autoclave, wt. % of reaction mixture

| Time (h) | 0.5 | 2.8 | 4.5 | NA |
|---|---|---|---|---|
| Wt. % | | | | feed |
| C3P | 0.00 | 0.14 | 0.03 | 0.00 |
| C4P | 5.05 | 14.16 | 20.94 | 0.00 |
| C5P | 86.79 | 65.61 | 50.73 | 99.86 |
| C6P | 4.99 | 12.88 | 16.83 | 0.00 |
| C7P | 1.19 | 3.60 | 5.73 | 0.00 |
| C8P | 0.38 | 1.15 | 2.05 | 0.00 |
| C9+ | 1.30 | 2.07 | 3.08 | 0.00 |
| C5N | 0.00 | 0.00 | 0.00 | 0.00 |
| C6N | 0.00 | 0.00 | 0.00 | 0.00 |
| C7N | 0.00 | 0.01 | 0.01 | 0.00 |
| C8N | 0.25 | 0.33 | 0.50 | 0.00 |
| C6A | 0.00 | 0.00 | 0.00 | 0.00 |
| C7A | 0.00 | 0.00 | 0.01 | 0.00 |
| C8A | 0.02 | 0.03 | 0.05 | 0.00 |
| nC4-nC5 unknowns | 0.00 | 0.00 | 0.00 | 0.14 |
| mmoles (based on wt. %) | | | | |
| C3P | 0 | 3 | 1 | 0 |
| C4P | 87 | 244 | 360 | 0 |
| C5P | 1203 | 909 | 703 | 1384 |
| C6P | 58 | 150 | 195 | 0 |
| C7P | 12 | 36 | 57 | 0 |
| C8P | 3 | 10 | 18 | 0 |
| C9+ | 10 | 16 | 24 | 0 |
| C5N | 0 | 0 | 0 | 0 |
| C6N | 0 | 0 | 0 | 0 |
| C7N | 0 | 0 | 0 | 0 |
| C8N | 2 | 3 | 4 | 0 |
| C6A | 0 | 0 | 0 | 0 |
| C7A | 0 | 0 | 0 | 0 |
| C8A | 0 | 0 | 1 | 0 |
| nC4-nC5 unknowns | 0 | 0 | 0 | 2 |
| Total mmoles | 1375 | 1371 | 1364 | 1386 |

Example 9: iC5—Stir Rate at 700 rpm with [1-Butyl-1-methylimidazolium][$Al_2Cl_7$] at 55° C. in a Hastelloy C Autoclave A 300 mL Hastelloy C autoclave. Hastelloy C baffle, and 75 mL stainless steel sample cylinder were dried in a 120° C. oven for at least 8. The dried autoclave and sample cylinder were brought into a nitrogen glovebox and allowed to cool to ambient temperature. The autoclave was charged with 55.310 g of [1-butyl-1-methylimidazolium][$Al_2Cl_7$], and the autoclave head was attached. To the sample cylinder 2.311 g of 2-chloro-2-methylpropane, which had previously been dried over activated sieves, was added. The sample cylinder was closed under nitrogen, and both the autoclave and sample cylinder were removed from the glovebox. The autoclave was charged with 111 g of iso-pentane from a pressurized feed charger without displacing the nitrogen present in the autoclave. The iso-pentane passed over a high surface sodium column to remove any water before entering the autoclave. Similarly, the nitrogen used to pressurize the charger and for all other work passed over a separate high surface sodium column. The sample cylinder was charged with 28 g of iso-pentane using the same method described above and attached to the autoclave. The autoclave was heated to 55° C., and the 2-chloro-2-methylpropane/iso-pentane solution in the sample cylinder was added with an over-pressure of nitrogen. After complete addition, the initial pressure in the autoclave was 150 psi (1.034 MPa), and the autoclave was set to stir at 700 rpm. The reaction was monitored periodically by GC. In order to analyze the paraffinic layer, the stirring was stopped, and the product was allowed to settle for 5 minutes. An aliquot was sampled directly from the autoclave by opening a valve from the autoclave, passing the paraffinic layer through a $SiO_2$ column, and then passing it directly into a GC sample loop. The mass ratio of liquid catalyst to iso-pentane was 0.41 and the volume ratio was 0.20. The mass rate of reaction was 150, and the volume rate was 310 after 0.6 h. The results of the run are shown in Tables 9 and 10.

TABLE 9

Disproportionation and Isomerization of iso-Pentane at 55° C., 700 rpm, with [1-butyl-3-methylimidazolium][$Al_2Cl_7$] in a Hastelloy C autoclave, wt. % of reaction mixture

| t (h) | % Conv. | C3− | iC4 | nC4 | iC5 | nC5 | C6P | C7+ | i/n | S. Disp. | $S_{isoparaffin}$ |
|---|---|---|---|---|---|---|---|---|---|---|---|
| 0.6 | 37 | 0.01 | 13.86 | 0.08 | 62.83 | 3.11 | 11.50 | 8.59 | 8.2 | 92 | 80 |
| 1.7 | 69 | 0.04 | 27.55 | 0.56 | 31.04 | 5.47 | 18.18 | 17.15 | 6.9 | 92 | 80 |
| 2.9 | 75 | 0.07 | 31.33 | 1.10 | 24.52 | 5.47 | 18.13 | 19.38 | 6.6 | 93 | 79 |
| 4.5 | 76 | 0.09 | 32.31 | 1.56 | 23.41 | 5.34 | 18.37 | 18.90 | 6.4 | 93 | 80 |

TABLE 10

Disproportionation and Isomerization of iso-Pentane at 55° C. 700 rpm, with [1-butyl-3-methylimidazolium][Al$_2$Cl$_7$] in a Hastelloy C autoclave, wt. % of reaction mixture

| Time (h) | 0.6 | 1.7 | 2.9 | 4.5 | NA |
|---|---|---|---|---|---|
| Wt. % | | | | | feed |
| C3P | 0.01 | 0.04 | 0.07 | 0.09 | 0.00 |
| C4P | 13.95 | 28.12 | 32.44 | 33.88 | 0.00 |
| C5P | 65.94 | 36.51 | 29.98 | 28.75 | 99.86 |
| C6P | 11.50 | 18.17 | 18.12 | 18.38 | 0.00 |
| C7P | 3.68 | 7.80 | 8.61 | 8.65 | 0.00 |
| C8P | 1.37 | 3.36 | 4.18 | 4.25 | 0.00 |
| C9+ | 3.01 | 5.09 | 5.43 | 5.09 | 0.00 |
| C5N | 0.00 | 0.00 | 0.00 | 0.00 | 0.00 |
| C6N | 0.00 | 0.00 | 0.00 | 0.00 | 0.00 |
| C7N | 0.01 | 0.01 | 0.01 | 0.01 | 0.00 |
| C8N | 0.45 | 0.84 | 0.93 | 0.86 | 0.00 |
| C6A | 0.00 | 0.00 | 0.00 | 0.00 | 0.00 |
| C7A | 0.00 | 0.03 | 0.04 | 0.04 | 0.00 |
| C8A | 0.08 | 0.06 | 0.23 | 0.06 | 0.00 |
| nC4-nC5 unknowns | 0.00 | 0.00 | 0.00 | 0.00 | 0.14 |
| mmoles (based on wt. %) | | | | | |
| C3P | 0 | 1 | 2 | 2 | 0 |
| C4P | 240 | 484 | 558 | 583 | 0 |
| C5P | 914 | 506 | 416 | 398 | 1384 |
| C6P | 133 | 211 | 210 | 213 | 0 |
| C7P | 37 | 78 | 86 | 86 | 0 |
| C8P | 12 | 29 | 37 | 37 | 0 |
| C9+ | 23 | 40 | 42 | 40 | 0 |
| C5N | 0 | 0 | 0 | 0 | 0 |
| C6N | 0 | 0 | 0 | 0 | 0 |
| C7N | 0 | 0 | 0 | 0 | 0 |
| C8N | 4 | 7 | 8 | 8 | 0 |
| C6A | 0 | 0 | 0 | 0 | 0 |
| C7A | 0 | 0 | 0 | 0 | 0 |
| C8A | 1 | 1 | 2 | 1 | 0 |
| nC4-nC5 unknowns | 0 | 0 | 0 | 0 | 2 |
| Total mmoles | 1365 | 1357 | 1361 | 1368 | 1386 |

Example 10: iC5 [("Bu)$_3$P(Hex)][Al$_2$Cl$_6$Br] in Hastelloy C Autoclave at 95° C.

A 300 mL Hastelloy C autoclave. Hastelloy C baffle, and 75 mL stainless steel sample cylinder were dried in a 120° C. oven for at least 8 h. The dried autoclave and sample cylinder were brought into a nitrogen glovebox and allowed to cool to ambient temperature. The autoclave was charged with 50.419 g of [("Bu)$_3$P(Hex)][Al$_2$Cl$_6$Br], and the autoclave head was attached. To the sample cylinder 3.680 g of 2-chloro-2-methylpropane, which had previously been dried over activated sieves, was added. The sample cylinder was closed under nitrogen, and both the autoclave and sample cylinder were removed from the glovebox. The autoclave was charged with 102 g of iso-pentane from a pressurized feed charger without displacing the nitrogen present in the autoclave. The iso-pentane passed over a high surface sodium column to remove any water before entering the autoclave. Similarly, the nitrogen used to pressurize the charger and for all other work passed over a separate high surface sodium column. The sample cylinder was charged with 15 g of iso-pentane using the same method described above and then attached to the autoclave. The autoclave was heated to 95° C., and the 2-chloro-2-methylpropane/iso-pentane solution in the sample cylinder was added with an over-pressure of nitrogen. After complete addition, the initial pressure in the autoclave was 165 psi (1.138 MPa), and the autoclave was set to stir at 1700 µm. The reaction was monitored periodically by GC. In order to analyze the paraffinic layer, the stirring was stopped, and the product was allowed to settle for 5 minutes. An aliquot was sampled directly from the autoclave by opening a valve from the autoclave, passing the paraffinic layer through a SiO$_2$ column, and then passing it directly into a GC sample loop. The mass ratio of liquid catalyst to iso-pentane was 0.46 and the volume ratio was 0.23. The mass rate of reaction was 260, and the volume rate was 520 after 0.6 h. The results of the run are shown in Tables 11 and 12.

TABLE 11

Disproportionation and Isomerization of iso-Pentane at 95° C., wt. % of reaction mixture

| t (h) | % Conv. | C3− | iC4 | nC4 | iC5 | nC5 | C6P | C7+ | i/n | S. Disp. | S$_{isoparaffin}$ | RON | RVP (psi) |
|---|---|---|---|---|---|---|---|---|---|---|---|---|---|
| 0.6 | 72 | 0.37 | 27.78 | 1.72 | 28.32 | 4.2 | 16.21 | 21.36 | 6.3 | 94 | 73 | 80.0 | 12.5 |
| 1.8 | 76 | 0.82 | 31.73 | 3.91 | 23.66 | 5.4 | 17.15 | 17.29 | 4.6 | 93 | 76 | 77.6 | 12.3 |
| 3.1 | 77 | 1.05 | 31.50 | 5.12 | 23.14 | 5.71 | 17.1 | 16.38 | 4.0 | 92 | 74 | ND | ND |
| 4.6 | 77 | 1.21 | 31.56 | 6.14 | 22.79 | 5.90 | 16.91 | 15.42 | 3.7 | 92 | 73 | ND | ND |

TABLE 12

Disproportionation and Isomerization of iso-Pentane at 95° C., wt. % of reaction mixture

| Time (h) | 0.6 | 1.8 | 3.1 | 4.6 | NA |
|---|---|---|---|---|---|
| Wt. % | | | | | feed |
| C3P | 0.37 | 0.82 | 1.05 | 1.21 | 0.00 |
| C4P | 29.50 | 35.64 | 36.62 | 37.70 | 0.00 |
| C5P | 32.51 | 29.06 | 28.85 | 28.69 | 99.86 |
| C6P | 16.22 | 17.16 | 17.10 | 16.91 | 0.00 |
| C7P | 7.66 | 8.19 | 7.96 | 7.56 | 0.00 |
| C8P | 3.42 | 3.88 | 3.79 | 3.57 | 0.00 |
| C9+ | 9.74 | 4.63 | 4.04 | 3.81 | 0.00 |
| C5N | 0.00 | 0.00 | 0.00 | 0.00 | 0.00 |
| C6N | 0.00 | 0.00 | 0.00 | 0.00 | 0.00 |
| C7N | 0.01 | 0.02 | 0.02 | 0.02 | 0.00 |
| C8N | 0.51 | 0.56 | 0.53 | 0.48 | 0.00 |
| C6A | 0.00 | 0.00 | 0.00 | 0.00 | 0.00 |
| C7A | 0.04 | 0.04 | 0.04 | 0.03 | 0.00 |
| C8A | 0.01 | 0.02 | 0.02 | 0.02 | 0.00 |
| nC4-nC5 | 0.00 | 0.00 | 0.00 | 0.00 | 0.14 |
| unknowns | | | | | |
| mmoles (based on wt. %) | | | | | |
| C3P | 8 | 19 | 24 | 27 | 0 |
| C4P | 508 | 613 | 630 | 649 | 0 |
| C5P | 451 | 403 | 400 | 398 | 1384 |
| C6P | 188 | 199 | 198 | 196 | 0 |
| C7P | 76 | 82 | 79 | 75 | 0 |
| C8P | 30 | 34 | 33 | 31 | 0 |
| C9+ | 76 | 36 | 31 | 30 | 0 |
| C5N | 0 | 0 | 0 | 0 | 0 |
| C6N | 0 | 0 | 0 | 0 | 0 |
| C7N | 0 | 0 | 0 | 0 | 0 |
| C8N | 5 | 5 | 5 | 4 | 0 |
| C6A | 0 | 0 | 0 | 0 | 0 |
| C7A | 0 | 0 | 0 | 0 | 0 |
| C8A | 0 | 0 | 0 | 0 | 0 |
| nC4-nC5 | 0 | 0 | 0 | 0 | 2 |
| unknowns | | | | | |
| Total mmoles | 1343 | 1391 | 1402 | 1411 | 1386 |

Example 11: nC5 with [("Bu)$_3$P(Hex)][AlCl$_6$Br] at 95° C. in a Hastelloy C Autoclave A 300 mL Hastelloy C autoclave, Hastelloy C baffle, and 75 mL stainless steel sample cylinder were dried in a 120° C. oven for at least 8 h. The dried autoclave and sample cylinder were brought into a nitrogen glovebox and allowed to cool to ambient temperature. The autoclave was charged with 50.409 g of [("Bu)$_3$P(Hex)][Al$_2$Cl$_6$Br], and the autoclave head was attached. To the sample cylinder 3.679 g of 2-chloro-2-methylpropane, which had previously been dried over activated sieves, was added. The sample cylinder was closed under nitrogen, and both the autoclave and sample cylinder were removed from the glovebox. The autoclave was charged with 102 g of n-pentane from a pressurized feed charger without displacing the nitrogen present in the autoclave. The n-pentane passed over a high surface sodium column to remove any water before entering the autoclave. Similarly, the nitrogen used to pressurize the charger and for all other work passed over a separate high surface sodium column. The sample cylinder was charged with 15 g of n-pentane using the same method described above and then attached to the autoclave. The autoclave was heated to 95° C., and the 2-chloro-2-methylpropane/n-pentane solution in the sample cylinder was added with an over-pressure of nitrogen. After complete addition, the initial pressure in the autoclave was 160 psi (1.103 MPa), and the autoclave was then set to stir at 1700 rpm. The reaction was monitored periodically by GC. In order to analyze the paraffinic layer, the stirring was stopped, and the product was allowed to settle for 5 minutes. An aliquot was sampled directly from the autoclave by opening a valve from the autoclave, passing the paraffinic layer through a SiO$_2$ column, and then passing it directly into a GC sample loop. The mass ratio of liquid catalyst to n-pentane was 0.46 and the volume ratio was 0.24. The mass rate of reaction was 130, and the volume rate was 240 after 1 h. The results of the rxn are shown in Tables 13 and 14.

TABLE 13

Disproportionation and Isomerization of n-Pentane at 95° C., wt. % of reaction mixture

| t (h) | % Conv. | C3− | iC4 | nC4 | iC5 | nC5 | C6P | C7+ | i/n | S. Disp. | $S_{isoparaffin}$ | $S_{iso-isom}$ |
|---|---|---|---|---|---|---|---|---|---|---|---|---|
| 1.0 | 59 | 0.42 | 18.63 | 1.71 | 19.46 | 41.34 | 10.27 | 8.14 | 16.9 | 67 | 90 | 33 |
| 2.2 | 70 | 0.94 | 22.7 | 3.08 | 20.83 | 29.43 | 12.54 | 10.30 | 12.1 | 70 | 87 | 30 |
| 3.5 | 76 | 0.91 | 25.1 | 4.06 | 21.56 | 23.72 | 13.57 | 11.03 | 10.4 | 72 | 86 | 28 |
| 4.8 | 80 | 1.05 | 26.39 | 4.78 | 21.83 | 20.06 | 14.26 | 11.63 | 9.4 | 73 | 86 | 27 |
| 8.0 | 85 | 1.35 | 27.64 | 6.10 | 21.68 | 14.82 | 14.78 | 12.84 | 8.0 | 74 | 83 | 25 |

TABLE 14

Disproportionation and Isomerization of n-Pentane at 95° C., wt. % of reaction mixture

| Time (h) | 1.0 | 2.2 | 3.5 | 4.8 | 8.0 | NA |
|---|---|---|---|---|---|---|
| Wt. % | | | | | | feed |
| C3P | 0.42 | 0.94 | 0.91 | 1.05 | 1.35 | 0.00 |
| C4P | 20.35 | 25.78 | 29.16 | 31.17 | 33.74 | 0.00 |
| C5P | 60.81 | 50.26 | 45.28 | 41.90 | 36.50 | 99.60 |
| C6P | 10.27 | 12.55 | 13.59 | 14.25 | 14.78 | 0.00 |
| C7P | 4.17 | 5.17 | 5.67 | 5.96 | 6.24 | 0.00 |
| C8P | 1.63 | 2.11 | 2.40 | 2.57 | 2.82 | 0.00 |
| C9+ | 2.02 | 2.71 | 2.58 | 2.67 | 4.10 | 0.00 |
| C5N | 0.00 | 0.00 | 0.00 | 0.00 | 0.00 | 0.00 |
| C6N | 0.00 | 0.00 | 0.00 | 0.00 | 0.00 | 0.00 |
| C7N | 0.01 | 0.02 | 0.02 | 0.02 | 0.02 | 0.00 |
| C8N | 0.26 | 0.32 | 0.36 | 0.38 | 0.41 | 0.00 |
| C6A | 0.00 | 0.00 | 0.00 | 0.00 | 0.00 | 0.00 |
| C7A | 0.01 | 0.02 | 0.02 | 0.02 | 0.02 | 0.00 |
| C8A | 0.06 | 0.13 | 0.03 | 0.03 | 0.04 | 0.00 |
| nC4-nC5 unknowns | 0.00 | 0.00 | 0.00 | 0.00 | 0.00 | 0.34 |
| nC5-nC6 unknowns | 0.00 | 0.00 | 0.00 | 0.00 | 0.00 | 0.05 |
| mmoles (based on wt. %) | | | | | | |
| C3P | 10 | 21 | 21 | 24 | 31 | 0 |
| C4P | 350 | 444 | 502 | 536 | 580 | 0 |
| C5P | 843 | 697 | 628 | 581 | 506 | 1380 |
| C6P | 119 | 146 | 158 | 165 | 172 | 0 |
| C7P | 42 | 52 | 57 | 59 | 62 | 0 |
| C8P | 14 | 18 | 21 | 23 | 25 | 0 |
| C9+ | 16 | 21 | 20 | 21 | 32 | 0 |
| C5N | 0 | 0 | 0 | 0 | 0 | 0 |
| C6N | 0 | 0 | 0 | 0 | 0 | 0 |
| C7N | 0 | 0 | 0 | 0 | 0 | 0 |
| C8N | 2 | 3 | 3 | 3 | 4 | 0 |
| C6A | 0 | 0 | 0 | 0 | 0 | 0 |
| C7A | 0 | 0 | 0 | 0 | 0 | 0 |
| C8A | 1 | 1 | 0 | 0 | 0 | 0 |
| nC4-nC5 unknowns | 0 | 0 | 0 | 0 | 0 | 5 |
| nC5-nC6 unknowns | 0 | 0 | 0 | 0 | 0 | 1 |
| Total mmoles | 1396 | 1403 | 1409 | 1413 | 1412 | 1386 |

Example 12: nC5 with [1-butyl-1-methylpyrrolidinium][$Al_2Cl_7$] at 95° C.

A 300 mL Hastelloy C autoclave. Hastelloy C baffle, and 75 mL stainless steel sample cylinder were dried in a 120° C. oven for at least 8 h. The dried autoclave and sample cylinder were brought into a nitrogen glovebox and allowed to cool to ambient temperature. The autoclave was charged with 52.795 g of [1-butyl-1-methylpyrrolidinium][$Al_2Cl_7$] and the autoclave head was attached. To the sample cylinder 5.24 g of 2-chloro-2-methylpropane, which had previously been dried over activated sieves, was added. The sample cylinder was closed under nitrogen, and both the autoclave and sample cylinder were removed from the glovebox. The autoclave was charged with 98 g of n-pentane from a pressurized feed charger without displacing the nitrogen present in the autoclave. The n-pentane passed over a high surface sodium column to remove any water before entering the autoclave. Similarly, the nitrogen used to pressurize the charger and for all other work passed over a separate high surface sodium column. The sample cylinder was charged with 33 g of n-pentane using the same method described above and attached to the autoclave. The autoclave was heated to 95° C., and the 2-chloro-2-methylpropane/n-pentane solution in the sample cylinder was added with an over-pressure of nitrogen. After complete addition, the initial pressure in the autoclave was 260 psi (1.793 MPa), and the autoclave was set to stir at 1700 rpm. The reaction was monitored periodically by GC. In order to analyze the paraffinic layer, the stirring was stopped, and the product was allowed to settle for 5 minutes. An aliquot was sampled directly from the autoclave by opening a valve from the autoclave, passing the paraffinic layer through a $SiO_2$ column, and then passing it directly into a GC sample loop. The mass ratio of liquid catalyst to n-pentane was 0.44 and the volume ratio was 0.21. The mass rate of reaction was 220, and the volume rate was 450 after 0.6 h. The results of the run are shown in Tables 15 and 16.

TABLE 15

Disproportionation and Isomerization of n-Pentane at 95° C. with [1-butyl-1-methylpyrrolidinium][$Al_2Cl_7$], wt. % of reaction mixture

| t (h) | % Conv. | C3− | iC4 | nC4 | iC5 | nC5 | C6P | C7+ | i/n | S. Disp. | $S_{isoparaffin}$ | $S_{iso-isom}$ | RON | RVP (psi) |
|---|---|---|---|---|---|---|---|---|---|---|---|---|---|---|
| 0.6 | 57 | 0.49 | 18.16 | 2.44 | 18.55 | 42.87 | 10.02 | 7.48 | 13.0 | 68 | 89 | 32 | ND | ND |
| 1.9 | 84 | 1.22 | 28.59 | 5.73 | 22.01 | 15.60 | 14.75 | 12.00 | 8.7 | 74 | 85 | 26 | 76.1 | 13.5 |
| 3.2 | 89 | 1.70 | 30.42 | 7.70 | 21.66 | 10.57 | 15.38 | 12.54 | 7.1 | 76 | 83 | 24 | 77.1 | 13.2 |
| 4.4 | 91 | 1.96 | 30.79 | 8.72 | 21.31 | 9.06 | 15.51 | 12.65 | 6.5 | 76 | 81 | 23 | 77.4 | 13.0 |

Disproportionation and Isomerization of n-Pentane at 95° C. with [1-butyl-1-methylpyrrolidinium][Al$_2$Cl$_7$], wt. % of reaction mixture

| Time (h) | 0.6 | 1.9 | 3.2 | 4.4 | NA |
|---|---|---|---|---|---|
| Wt. % | | | | | feed |
| C3P | 0.49 | 1.22 | 1.70 | 1.96 | 0.00 |
| C4P | 20.60 | 34.32 | 38.12 | 39.51 | 0.00 |
| C5P | 61.41 | 37.61 | 32.23 | 30.37 | 99.60 |
| C6P | 10.02 | 14.76 | 15.39 | 15.50 | 0.00 |
| C7P | 3.93 | 6.04 | 6.24 | 6.25 | 0.00 |
| C8P | 1.52 | 2.64 | 2.85 | 2.89 | 0.00 |
| C9+ | 1.71 | 2.97 | 3.00 | 3.05 | 0.00 |
| C5N | 0.00 | 0.00 | 0.00 | 0.00 | 0.00 |
| C6N | 0.00 | 0.00 | 0.00 | 0.00 | 0.00 |
| C7N | 0.01 | 0.01 | 0.02 | 0.02 | 0.00 |
| C8N | 0.25 | 0.39 | 0.41 | 0.41 | 0.00 |
| C6A | 0.00 | 0.00 | 0.00 | 0.00 | 0.00 |
| C7A | 0.01 | 0.02 | 0.02 | 0.02 | 0.00 |
| C8A | 0.04 | 0.01 | 0.02 | 0.02 | 0.00 |
| nC4-nC5 unknowns | 0.00 | 0.00 | 0.00 | 0.00 | 0.34 |
| nC5-nC6 unknowns | 0.00 | 0.00 | 0.00 | 0.00 | 0.05 |
| mmoles (based on wt. %) | | | | | |
| C3P | 11 | 28 | 39 | 44 | 0 |
| C4P | 354 | 591 | 656 | 680 | 0 |
| C5P | 851 | 521 | 447 | 421 | 1380 |
| C6P | 116 | 171 | 179 | 180 | 0 |
| C7P | 39 | 60 | 62 | 62 | 0 |
| C8P | 13 | 23 | 25 | 25 | 0 |
| C9+ | 13 | 23 | 23 | 24 | 0 |
| C5N | 0 | 0 | 0 | 0 | 0 |
| C6N | 0 | 0 | 0 | 0 | 0 |
| C7N | 0 | 0 | 0 | 0 | 0 |
| C8N | 2 | 4 | 4 | 4 | 0 |
| C6A | 0 | 0 | 0 | 0 | 0 |
| C7A | 0 | 0 | 0 | 0 | 0 |
| C8A | 0 | 0 | 0 | 0 | 0 |
| nC4-nC5 unknowns | 0 | 0 | 0 | 0 | 5 |
| nC5-nC6 unknowns | 0 | 0 | 0 | 0 | 1 |
| Total mmoles | 1402 | 1421 | 1435 | 1441 | 1386 | several days) and then the autoclave head was attached. The sample cylinder was charged with 8.833 g of a 82.29 wt. % n-heptane and 17.71 wt. % 2-chloro-2-methylpropane mixture, both of which had previously been dried over activated sieves. The sample cylinder was closed under nitrogen, and both the autoclave and sample cylinder were removed from the glovebox. The autoclave was heated to 55° C. and then the 2-chloro-2-methylpropane/n-heptane solution in the sample cylinder was added with an over-pressure of nitrogen. The nitrogen used to provide this overpressure was passed over a high surface sodium column. After complete addition, the initial pressure in the autoclave was 340 psi (2.34 MPa), and the autoclave was set to stir at 1700 rpm. The reaction was monitored by GC. In order to analyze the paraffinic layer, the stirring was stopped, and the product was allowed to settle for 5 minutes. An aliquot was sampled directly from the autoclave by opening a valve from the autoclave, passing the paraffinic layer through a SiO$_2$ column, and then passing it directly into a GC sample loop. After about 24 the temperature was increased to 80° C. At the end of the reaction (45 h), an aliquot was sampled directly from the autoclave by opening a valve from the autoclave, passing the paraffinic layer through a SiO$_2$ column, and into a sample cylinder. The sample cylinder was then charged to about 300 psi using nitrogen prior to offline analysis. The mass ratio of liquid catalyst to n-heptane was 0.36 and the volume ratio was 0.20. The mass rate of reaction was 2, and the volume rate was 3 after 45 h. The results of the run are shown in Table 17 and were determined using the UOP980 method offline.

TABLE 17

Disproportionation and Isomerization of n-heptane at 55-80° C., 1700 rpm, with [("Bu)$_3$P(Hex)][Al$_2$Cl$_6$Br] in a Hastelloy C autoclave, wt. % of reaction mixture

| t (h) | % Conv. | C3– | iC4 | nC4 | iC5 | nC5 | C6P | nC7 | C7P | C8P | Heavies | S. i/n | S. Disp. | S. Isom. C7P |
|---|---|---|---|---|---|---|---|---|---|---|---|---|---|---|
| 0.0 (feed) | NA | 0.00 | 0.00 | 0.00 | 0.04 | 0.00 | 0.00 | 99.25 | 99.55 | 0.00 | | NA | NA | NA |
| 45 | 26 | 0.07 | 3.90 | 0.14 | 3.31 | 0.16 | 2.89 | 73.44 | | | 15.14 | | | |

Example 13: nC7—Stir Rate at 1700 rpm with [("Bu)$_3$P(Hex)][Al$_2$Cl$_6$Br] at 55° C.-80° C. in a Hastelloy C Autoclave A 300 mL Hastelloy C autoclave, Hastelloy C baffle, and 75 mL stainless steel sample cylinder were dried in a 110° C. oven for at least 8 h. The dried autoclave and sample cylinder were brought into a nitrogen glovebox and allowed to cool to ambient temperature. The autoclave was charged with 50.425 g of [("Bu)$_3$P(Hex)][Al$_2$Cl$_6$Br], 201 mL of n-heptane (pre-dried by storing over activated 3 A MS for Example 14: nC7—Stir Rate at 1700 rpm with [1-Butyl-1-methylimidazolium][Al$_2$Cl$_7$] at 95° C. in a Hastelloy C Autoclave A 300 mL Hastelloy C autoclave, Hastelloy C baffle, and 50 mL stainless steel sample cylinder were dried in a 110° C. oven for at least 5 h and then placed in a glovebox antechamber and evacuated over night. The autoclave and sample cylinder were then brought into a nitrogen glovebox. The autoclave was charged with 55.335 g of [1-butyl-1-methylimidazolium][Al$_2$Cl$_7$], 211 mL of n-heptane (pre-dried by storing over activated 3 A MS for at least 1 week) and then the autoclave head was attached. The sample cylinder was charged with 15.358 g of a 62.30 wt. % n-heptane and 37.70 wt. % 2-chloro-2-methylpropane mixture, both of which had previously been dried over activated sieves. The sample cylinder was closed under nitrogen, and both the autoclave and sample cylinder were removed from the glovebox. The autoclave was heated to 95° C., and then the 2-chloro-2-methylpropane/n-heptane solution in the sample cylinder was added with an over-pressure of nitrogen. The nitrogen used to provide this overpressure was passed over a high surface sodium column. After complete addition, the initial pressure in the autoclave was 280 psi (1.93 MPa), and the autoclave was set to stir at 1700 rpm. The reaction was monitored by GC. In order to analyze the paraffinic layer, the stirring was stopped, and the product was allowed to settle for 5 minutes. An aliquot was sampled directly from the autoclave by opening a valve from the autoclave, passing the paraffinic layer through a $SiO_2$ column, and then passing it directly into a GC sample loop. The mass ratio of liquid catalyst to n-heptane was 0.40 and the volume ratio was 0.21. The mass rate of reaction was 110, and the volume rate was 210 after 1 h. The results of the run are shown in Tables 18 and 19 and were determined using the UOP690 method. Alternatively, the aliquot could be introduced to a sample cylinder, after passing through the $SiO_2$ column, and analyzed offline. If this method was used, after introduction of the sample to the sample cylinder, the cylinder would then be charged to about 300 psi using nitrogen prior to offline analysis and analyzed using the UOP980 method.

TABLE 18

Disproportionation and Isomerization of n-heptane at 95° C., 1700 rpm, with [1-butyl-3-methylimidazolium][$Al_2Cl_7$] in a Hastelloy C autoclave, wt. % of reaction mixture

| t (h) | % Conv. | C3− | iC4 | nC4 | iC5 | nC5 | C6P | nC7 | C7P | C8P | nC8-nC10 | C10+ | i/n | S. Disp. | $S_{iso-isom}$ |
|---|---|---|---|---|---|---|---|---|---|---|---|---|---|---|---|
| 0.0 (feed) | NA | 0.00 | 0.00 | 0.00 | 0.04 | 0.00 | 0.00 | 99.25 | 99.55 | 0.00 | | | NA | NA | NA |
| 1.0 | 44 | 0.58 | 7.63 | 0.89 | 7.58 | 0.77 | 7.06 | | 66.21 | 3.26 | 3.07 | 2.43 | 15 | 77 | 22 |

TABLE 19

Disproportionation and Isomerization of n-heptane at 95° C., 1700 rpm, with [1-butyl-3-methylimidazolium][$Al_2Cl_7$] in a Hastelloy C autoclave, wt. % of reaction mixture

| Time (h) | 1.0 | NA |
|---|---|---|
| Wt. % | | Feed |
| C3P | 0.58 | 0.00 |
| C4P | 8.52 | 0.00 |
| C5P | 8.35 | 0.04 |
| C6P | 7.06 | 0.00 |
| C7P | 66.21 | 99.55 |
| C8P | 3.26 | 0.00 |
| C9P | 1.62 | 0.00 |
| C10P | 1.40 | 0.00 |
| C10+ | 2.43 | 0.00 |
| C5N | 0.00 | 0.00 |
| C6N | 0.00 | 0.01 |
| C7N | 0.03 | 0.40 |
| C8N | 0.40 | 0.00 |
| C6A | 0.00 | 0.00 |

TABLE 19-continued

Disproportionation and Isomerization of n-heptane at 95° C., 1700 rpm, with [1-butyl-3-methylimidazolium][$Al_2Cl_7$] in a Hastelloy C autoclave, wt. % of reaction mixture

| Time (h) | 1.0 | NA |
|---|---|---|
| C7A | 0.06 | 0.00 |
| C8A | 0.04 | 0.00 |
| nC4-nC5 | 0.00 | |
| nC5-nC6 unknowns | 0.00 | 0.00 |
| mmoles (based on wt. %) | | |
| C3P | 13 | 0 |
| C4P | 147 | 0 |
| C5P | 116 | 1 |
| C6P | 82 | 0 |
| C7P | 661 | 993 |
| C8P | 29 | 0 |
| C9P | 13 | 0 |
| C10P | 10 | 0 |
| C10+ | 16 | 0 |
| C5N | 0 | 0 |
| C6N | 0 | 0 |
| C7N | 0 | 4 |
| C8N | 4 | 0 |
| C6A | 0 | 0 |
| C7A | 1 | 0 |
| C8A | 0 | 0 |
| nC4-nC5 | 0 | |
| nC5-nC6 unknowns | 0 | 0 |
| Total mmoles | 1090 | 998 |

Example 15: nC4—Stir Rate at 1700 rpm with [("Bu)$_3$P(Hex)][$Al_2Cl_6Br$] in Hastelloy C Autoclave at 95° C.-105° C.

A 300 mL Hastelloy C autoclave. Hastelloy C baffle, and 75 mL stainless steel sample cylinder were dried in a 110° C. oven for at least 8 h. The dried autoclave and sample cylinder were brought into a nitrogen glovebox and allowed to cool to ambient temperature. The autoclave was charged with 50.467 g of [("Bu)P(Hex)][$Al_2Cl_6Br$], and the autoclave head was attached. To the sample cylinder 3.692 g of 2-chloro-2-methylpropane, which had previously been dried over activated sieves, was added. The sample cylinder was closed under nitrogen, and both the autoclave and sample cylinder were removed from the glovebox. The autoclave was charged with 103.1 g of n-butane from a pressurized feed charger without displacing the nitrogen present in the autoclave. The sample cylinder was charged with 10.9 g of n-butane using the same method described above and attached to the autoclave. The autoclave was heated to 105° C., and the 2-chloro-2-methylpropane/iso-pentane solution in the sample cylinder was added with an over-pressure of nitrogen. The nitrogen used to pressurize the charger and for all other work passed over a separate high surface sodium column. After complete addition, the initial pressure in the autoclave was 420 psi (2.90 MPa), the autoclave was set to stir at 1700 rpm and the temperature dropped to 101° C. The temperature was difficult to maintain above 100° C., so the reaction was cooled to 95° C. where it was easier to maintain temperature. The reaction was in the 98-101° C. region for about 1 h before being allowed to cool to 95° C. The reaction was monitored periodically by GC offline. In order to analyze the paraffinic layer, the stirring was stopped, and the product was allowed to settle for 5 minutes. An aliquot was sampled directly from the autoclave by opening a valve from the autoclave, passing the paraffinic layer through a $SiO_2$ column, and into a sample cylinder. The sample cylinder was then charged to about 300 psi using nitrogen prior to offline analysis. The mass ratio of ionic liquid to n-butane was 0.48 and the volume ratio of ionic liquid:n-butane was 0.22 using the following densities: 1.22 g/mL for the liquid catalyst and 0.57 g/mL for n-butane. The mass reaction rate was 5, and the volume reaction rate was 10. The results of the run are shown in Table 20 and were determined using the UOP980 method.

2-methylpropane/n-heptane solution in the sample cylinder was added with an over-pressure of nitrogen. The nitrogen used to pressurize the charger and for all other work passed over a separate high surface sodium column. After complete addition, the initial pressure in the autoclave was 360 psi (2.48 MPa) and the autoclave was set to stir at 1700 rpm. The reaction was monitored periodically by GC. In order to analyze the paraffinic layer, the stirring was stopped, and the product was allowed to settle for 5 minutes. An aliquot was sampled directly from the autoclave by opening a valve from the autoclave, passing the paraffinic layer through a $SiO_2$ column, and then passing it directly into a GC sample loop. At the end of the reaction, an aliquot was sampled directly from the autoclave by opening a valve from the autoclave, passing the paraffinic layer through a $SiO_2$ column, and into a sample cylinder. The sample cylinder was then charged to about 300 psi using nitrogen prior to offline analysis. The mass ratio of ionic liquid to hydrocarbon feed was 0.44. The volume ratio of ionic liquid to hydrocarbon feed was 0.22 using the following densities: 1.22 g/mL for the liquid catalyst, 0.68 g/mL for n-heptane and 0.55 g/mL for isobu-

TABLE 20

Disproportionation and Isomerization of n-butane at 95° C., 1700 rpm, Hastelloy C autoclave, wt. % of reaction mixture

| t (h) | % Conv. | C3− | iC4 | nC4 | iC5 | nC5 | C6P | C7+ | i/n | S. Disp | S. Isom iC4 |
|---|---|---|---|---|---|---|---|---|---|---|---|
| 0 (feed) | 0 | 0.01 | 0.18 | 99.09 | 0.00 | 0.00 | 0.00 | 0.60 | NA | NA | NA |
| 3.5 | 7 | 0.07 | 6.76 | 91.97 | 0.71 | 0.08 | 0.16 | 0.14 | 72 | 8 | 92 |
| 27.0 | 15 | 0.09 | 13.67 | 84.53 | 0.93 | 0.15 | 0.17 | 0.33 | 80 | 7 | 93 |

Example 16: iC4 and nC7 Reverse Disproportionation—Stir Rate at 1700 rpm with [($^n$Bu)$_3$P(Hex)][Al$_2$Cl$_6$Br] in Hastelloy C Autoclave at 95° C.

A 300 mL Hastelloy C autoclave. Hastelloy C baffle, and 75 mL stainless steel sample cylinder were dried in a 110° C. oven for at least 8 h. The dried autoclave and sample cylinder were brought into a nitrogen glovebox and allowed to cool to ambient temperature. The autoclave was charged with 50.428 g of [($^n$Bu)$_3$P(Hex)][Al$_2$Cl$_6$Br], 40.368 g of n-heptane (pre-dried by storing over activated 3 A MS for several days) and the autoclave head was attached. To the sample cylinder 1.501 g of 2-chloro-2-methylpropane, which had previously been dried over activated sieves, and 12.868 g of n-heptane was added. The sample cylinder was closed under nitrogen, and both the autoclave and sample cylinder were removed from the glovebox. The autoclave was charged with 65 g of iso-butane from a pressurized feed charger without displacing the nitrogen present in the autoclave. The autoclave was heated to 95° C., and the 2-chlorotane. The mass reaction rate was 2, and the volume reaction rate was 3 after 28 h. The mass reaction rate was 2 and the volume reaction rate was 3 after 21 h. The results of the run are shown in Table 21 and were determined using the UOP980 method offline. The feed composition (t (O)) is based on the mass of the added reagents.

TABLE 21

Reverse Disproportionation of n-Heptane and iso-Butane at 95° C., 1700 rpm, Hastelloy C autoclave, wt. % of reaction mixture

| t (h) | % Conv. | C3− | iC4 | nC4 | iC5 | nC5 | C6P | nC7 | Heavies | i/n | S. Disp. | S. Isom. iC4 |
|---|---|---|---|---|---|---|---|---|---|---|---|---|
| 0 (feed) | 0 | | 55 | | | | | 45 | | NA | NA | NA |
| 28 | 19 | 0.27 | 56.99 | 1.38 | 3.16 | 0.08 | 1.70 | 23.80 | 11.39 | | | |

Example 17: nC4/nC5—Stir Rate at 1700 rpm with [1-butyl-3-methylimidazolium][Al$_2$Cl$_7$] in Hastelloy C Autoclave at 100° C.

A 300 mL Hastelloy C autoclave, Hastelloy C baffle, and 75 mL stainless steel sample cylinder were dried in a 110° C. oven for at least 8 h. The dried autoclave and sample cylinder were brought into a nitrogen glovebox and allowed to cool to ambient temperature. The autoclave was charged with 55.387 g of [1-butyl-3-methylimidazolium][Al$_2$Cl$_7$], and the autoclave head was attached. 5.6 g of 2-chloro-2-methylpropane, which had previously been dried over activated 3 A molecular sieves, was added to the sample cylinder. The sample cylinder was closed under nitrogen, and both the autoclave and sample cylinder were removed from the glovebox. The autoclave was charged with 103 g of n-butane from a pressurized feed charger without displacing the nitrogen present in the autoclave, but was then vented down to 86 g of n-butane. The sample cylinder was charged with 31 g of n-pentane from a pressurized feed charger without displacing the nitrogen present in the sample cylinder. The autoclave was heated to 103° C. while stirring at 100 rpm. Once this temperature was reached, stirring was stopped and the 2-chloro-2-methylpropane/n-pentane solution in the sample cylinder was added with an over-pressure of nitrogen. The nitrogen used to pressurize the charger and for all other work passed over a separate high surface sodium column. After complete addition, the reaction mixture was stirred at 1700 rpm and the temperature increased to 110° C. The pressure in the autoclave at this point was 600 psi (4.14 MPa). After 0.1 h, during which time the temperature fluctuated from 104-111° C., stirring was stopped, the reaction mixture was allowed to settle for 5 minutes, and the paraffinic layer was analyzed by GC. An aliquot was sampled directly from the autoclave by opening a valve from the autoclave, passing the paraffinic layer through a $SiO_2$ column, and then passing it directly into a GC sample loop. The GC method employed was UOP690. Afterwards, a liquid sample was removed by filtering through a $SiO_2$ column into a sample cylinder. The liquid contained within the sample cylinder was pressurized with nitrogen to 300 psi (2.07 MPa) and was then analyzed offline using an analogous method. During sampling, the reaction cooled to 91° C. Afterwards, the reaction was reheated to 100° C. with stirring at 1700 rpm, which took 0.7 h to achieve, and the pressure at this point was 350 psi (2.41 MPa). The reaction was continued for an additional 17.6 h at this temperature, and the mixture was then analyzed is a similar manner. The results of the run are shown in Table 22 and were determined using the UOP690 method online. The mass ratio of liquid catalyst to hydrocarbon feed was 0.52, and the volume ratio was 0.23 using the following densities: 1.34 g/mL for the liquid catalyst, 0.626 g/mL for n-pentane and 0.57 g/mL for n-butane. The mass reaction rate was 650, and the volume reaction rate was 1500 after 0.1 h.

Example 18: nC4/nC5—Stir Rate at 1700 rpm with [1-butyl-3-methylimidazolium][$Al_2Cl_7$] in Hastelloy C Autoclave at 100° C.

A 300 mL Hastelloy C autoclave. Hastelloy C baffle, and 500 mL stainless steel sample cylinder were dried in a 110° C. oven for at least 8 h. The dried autoclave and sample cylinder were brought into a nitrogen glovebox and allowed to cool to ambient temperature. The autoclave was charged with 55.404 g of [1-butyl-3-methylimidazolium][$Al_2Cl_7$], and the autoclave head was attached. 11.821 g of 2-chloro-2-methylpropane, which had previously been dried over activated 3 A molecular sieves, was added to a 500 mL sample cylinder. The sample cylinder was closed under nitrogen, and both the autoclave and sample cylinder were removed from the glovebox. The sample cylinder was charged with 61.9 g of n-pentane, which was passed over a high surface sodium column, followed by 200.9 g of n-butane from a pressurized feed charger. The sample cylinder was then charged to about 600 psi (4.14 MPa) with nitrogen. A portion of the stock solution was analyzed by GC offline. The autoclave was charged with 130.3 g of the n-butane/n-pentane/2-chloro-2-methylpropane stock solution at room temperature, without displacing the nitrogen present in the autoclave. The initial temperature and pressure were 26° C. and 340 psi (2.34 MPa). The reaction mixture was set to stir at 1700 rpm while the autoclave was heated to 100° C.; it took 1.2 h to reach temperature, and the initial pressure was 980 psi (6.76 MPa). After a total of 18.8 h, the pressure was 1090 psi (7.52 MPa) within the autoclave. At this time, the reaction mixture was cooled to 85° C. which took 1.6 h, and it was then analyzed by GC. In order to analyze the paraffinic layer, the stirring was stopped, and the product was allowed to settle for 5 minutes. An aliquot was sampled directly from the autoclave by opening a valve from the autoclave, passing the paraffinic layer through a $SiO_2$ column, and then passing it directly into a GC sample loop. The GC method employed was UOP690. Afterwards, a liquid sample was removed by filtering through a $SiO_2$ column into a sample cylinder. The liquid contained within the sample cylinder was pressurized with nitrogen to about 300 psi (2.07 MPa) and was then analyzed offline using an analogous method. The results of the run are shown in Table 23 and were determined using the UOP690 method. The GC of the feed (0.0 h in Table 23) is the wt. % of the components in the 500 mL sample cylinder, without integrating 2-chloro-2-methylpropane. The mass ratio of liquid catalyst to hydrocarbon feed was 0.49, and the volume ratio was 0.21 using the following densities: 1.34 g/mL for the liquid catalyst, 0.626 g/mL for n-pentane and 0.57 g/mL for n-butane. The mass reaction rate was 6, and the volume reaction rate was 14 after 20.4 h.

TABLE 22

Isomerization and disproportionation of a n-butane/n-pentane feed at 100° C., 1700 rpm, Hastelloy C autoclave, wt. % of feed and reaction mixture

| HC | C3P | iC4 | nC4 | iC5 | nC5 | C6P | C7P | C8P | nC4-nC5[b] | nC5-nC6[b] | nC8-nC9[b] | nC9-nC10[b] | nC10+[b] |
|---|---|---|---|---|---|---|---|---|---|---|---|---|---|
| nC5[a] | 0.00 | 0.00 | 0.00 | 0.03 | 99.05 | 0.00 | 0.00 | 0.00 | 0.88 | 0.03 | 0.00 | 0.00 | 0.00 |
| nC4[a] | 0.01 | 0.17 | 99.71 | 0.00 | 0.00 | 0.00 | 0.00 | 0.00 | 0.10 | 0.00 | 0.00 | 0.00 | 0.00 |
| time (h) | C3P | iC4 | nC4 | iC5 | nC5 | C6P | C7P | C8P | nC4-nC5[b] | nC5-nC6[b] | nC8-nC9[b] | nC9-nC10[b] | nC10+[b] |
| 0.1 | 0.44 | 15.52 | 52.06 | 11.64 | 13.97 | 3.87 | 0.81 | 0.49 | 0.64 | 0.11 | 0.11 | 0.06 | 0.05 |
| 18.4 | 4.35 | 42.59 | 24.64 | 15.16 | 4.17 | 6.80 | 1.03 | 0.67 | 0.19 | 0.00 | 0.13 | 0.05 | 0.10 |

[a]Composition of the pure hydrocarbon feed, [b]Unknowns within these ranges

TABLE 23

Isomerization and disproportionation of a n-butane/n-pentane feed at 100° C., 1700 rpm, Hastelloy C autoclave, wt. % of feed and reaction mixture

| time (h) | C3P | iC4 | nC4 | iC5 | nC5 | C6P | C7P | C8P | nC4-nC5[a] | nC5-nC6[a] | nC8-nC9[a] | nC9-nC10[a] | nC10+[a] |
|---|---|---|---|---|---|---|---|---|---|---|---|---|---|
| 0.0 | 0.01 | 0.13 | 73.81 | 0.01 | 25.26 | 0.00 | 0.00 | 0.00 | 0.21 | 0.01 | 0.00 | 0.00 | 0.06 |
| 20.4 | 1.35 | 40.64 | 33.77 | 13.40 | 3.78 | 5.30 | 0.73 | 0.57 | 0.08 | 0.00 | 0.10 | 0.04 | 0.09 |

[a]Unknowns within these ranges

Example 19: nC4—Stir Rate at 1700 rpm with [1-butyl-3-methylimidazolium][Al$_2$Cl$_7$] in Hastelloy C Autoclave at 100° C.

A 300 mL Hastelloy C autoclave, Hastelloy C baffle, and 75 mL stainless steel sample cylinder were dried in a 110° C. oven for at least 8 h. The dried autoclave and sample cylinder were brought into a nitrogen glovebox and allowed to cool to ambient temperature. The autoclave was charged with 55.394 g of [1-butyl-3-methylimidazolium][Al$_2$Cl$_7$] and the autoclave head was attached. 5.818 g of 2-chloro-2-methylpropane, which had previously been dried over activated 3 A molecular sieves, was added to the sample cylinder. The sample cylinder was closed under nitrogen, and both the autoclave and sample cylinder were removed from the glovebox. The autoclave was charged with 120 g of n-butane from a pressurized feed charger, which was then vented down to 94 g of n-butane in the autoclave. The sample cylinder was charged with 15 g of n-butane from a pressurized feed charger without displacing the nitrogen present in the sample cylinder. The autoclave was heated to 100° C. while stirring at 138 rpm. Once the temperature was achieved, stirring was stopped, and the 2-chloro-2-methylpropane/n-butane solution in the sample cylinder was added with an over-pressure of nitrogen. The nitrogen used to pressurize the charger and for all other work passed over a separate high surface sodium column. After complete addition, stirring was started again at 1700 rpm: the initial pressure in the autoclave was 540 psi (3.72 MPa), and the temperature was 112° C. After 0.2 h, during which time the temperature fluctuated from 98-112° C. stirring was stopped, the reaction mixture was allowed to settle, and the paraffinic layer was analyzed by GC. In order to analyze the paraffinic layer, the stirring was stopped, and the product was allowed to settle for 5 minutes. An aliquot was sampled directly from the autoclave by opening a valve from the autoclave, passing the paraffinic layer through a SiO$_2$ column, and then passing it directly into a GC sample loop. The GC method employed was UOP690. Afterwards, a liquid sample was removed by filtering through a SiO$_2$ column into a sample cylinder. The liquid contained within the sample cylinder was pressurized with nitrogen to 300 psi (2.07 MPa) and was then analyzed offline using an analogous method. After GC analysis, the reaction was stirred at 1700 rpm and the temperature had cooled to 96° C. Reheating to 100° C. took 0.6 h. The reaction was continued for an additional 21.1 h at this temperature. The mixture was then analyzed in a similar manner. The results of the nm are shown in Table 24 and were determined using the UOP690 method online. The mass ratio of liquid catalyst to hydrocarbon feed was 0.56, and the volume ratio was 0.24 using the following densities: 1.34 g/mL for the liquid catalyst and 0.57 g/mL for n-butane. The mass reaction rate was 240, and the volume reaction rate was 570 after 0.2 h.

TABLE 24

Isomerization and disproportionation of n-butane at 100° C., 1700 rpm, Hastelloy C autoclave, wt. % of feed and reaction mixture

| time (h) | C3P | iC4 | nC4 | iC5 | nC5 | C6P | C7P | C8P | nC4-nC5[a] | nC5-nC6[a] | nC8-nC9[a] | nC9-nC10[a] | nC10+[a] |
|---|---|---|---|---|---|---|---|---|---|---|---|---|---|
| 0.0 | 0.01 | 0.17 | 99.71 | 0.00 | 0.00 | 0.00 | 0.00 | 0.00 | 0.10 | 0.00 | 0.00 | 0.00 | 0.00 |
| 0.2 | 0.37 | 21.55 | 72.71 | 3.04 | 0.77 | 0.79 | 0.19 | 0.31 | 0.11 | 0.00 | 0.02 | 0.00 | 0.05 |
| 21.9 | 0.85 | 52.78 | 38.09 | 5.06 | 1.38 | 0.78 | 0.07 | 0.30 | 0.11 | 0.00 | 0.07 | 0.05 | 0.15 |

[a]Unknowns within these ranges

Example 20: nC4—Stir Rate at 1700 rpm with [1-butyl-3-methylimidazolium][Al$_2$Cl$_7$] in Hastelloy C Autoclave at 90° C.

A 300 mL Hastelloy C autoclave, Hastelloy C baffle, and 75 mL stainless steel sample cylinder were dried in a 110° C. oven for at least 8 h. The dried autoclave and sample cylinder were brought into a nitrogen glovebox and allowed to cool to ambient temperature. The autoclave was charged with 55.392 g of [1-butyl-3-methylimidazolium][Al$_2$Cl$_7$], and the autoclave head was attached. 5.823 g of 2-chloro-2-methylpropane, which had previously been dried over activated 3 A molecular sieves, was added to the sample cylinder. The sample cylinder was closed under nitrogen, and both the autoclave and sample cylinder were removed from the glovebox. The autoclave was charged with 117 g of n-butane from a pressurized feed charger, which was then vented down to 101 g of n-butane in the autoclave. The sample cylinder was charged with 15.7 g of n-butane from a pressurized feed charger without displacing the nitrogen present in the sample cylinder. The autoclave was heated to 90° C. with stirring at 115 rpm. Once the temperature had stabilized, stirring was stopped, and the 2-chloro-2-methylpropane/n-butane solution in the sample cylinder was added with an over-pressure of nitrogen. The nitrogen used to pressurize the charger and for all other work passed over a separate high surface sodium column. After complete addition, the initial pressure in the autoclave was 320 psi (2.21 MPa), and the autoclave was set to stir at 1700 rpm. After 97 h, stirring was stopped and the reaction mixture was allowed to settle and the paraffinic layer was analyzed by GC. In order to analyze the paraffinic layer, the stirring was stopped, and the product was allowed to settle for 5 minutes. An aliquot was sampled directly from the autoclave by opening a valve from the autoclave, passing the paraffinic layer through a SiO$_2$ column, and then passing it directly into a GC sample loop. The GC method employed was UOP690. Afterwards, a liquid sample was removed by filtering through a SiO$_2$ column into a sample cylinder. The liquid contained within the sample cylinder was pressurized with nitrogen to 300 psi (2.07 MPa) and was then analyzed offline using an analogous method. The results of the run are shown in Table 25 and were determined using the UOP690 method online. The mass ratio of liquid catalyst to hydrocarbon feed was 0.52, and the volume ratio was 0.22 using the following densities: 1.34 g/mL for the liquid catalyst and 0.57 g/mL for n-butane. The mass reaction rate was 0.8, and the volume reaction rate was 2 after 97 h.

autoclave by opening a valve from the autoclave, passing the paraffinic layer through a $SiO_2$ column, and then passing it directly into a GC sample loop. The GC method employed was UOP690. Afterwards, a liquid sample was removed by filtering through a $SiO_2$ column into a sample cylinder. The

TABLE 25

Isomerization and disproportionation of n-butane at 90° C., 1700 rpm, Hastelloy C autoclave, wt. % of feed and reaction mixture

| time (h) | C3P | iC4 | nC4 | iC5 | nC5 | C6P | CV | C8P | nC4-nC5[a] | nC5-nC6[a] | nC8-nC9[a] | nC9-nC10[a] | nC10+[a] |
|---|---|---|---|---|---|---|---|---|---|---|---|---|---|
| 0.0 | 0.01 | 0.17 | 99.71 | 0.00 | 0.00 | 0.00 | 0.00 | 0.00 | 0.10 | 0.00 | 0.00 | 0.00 | 0.00 |
| 97 | 0.33 | 33.74 | 60.38 | 3.03 | 0.77 | 0.61 | 0.14 | 0.45 | 0.11 | 0.00 | 0.08 | 0.06 | 0.10 |

[a]Unknowns within these ranges

Example 21: nC4—Stir Rate at 1700 rpm with [1-butyl-3-methylimidazolium][Al₂Cl₇] in Hastelloy C Autoclave at 100° C.

A 300 mL Hastelloy C autoclave. Hastelloy C baffle, and 500 mL stainless steel sample cylinder were dried in a 110° C. oven for at least 8 h. The dried autoclave and sample cylinder were brought into a nitrogen glovebox and allowed to cool to ambient temperature. The autoclave was charged with 55.390 g of [1-butyl-3-methylimidazolium][Al₂Cl₇], and the autoclave head was attached. 8.754 g of 2-chloro-2-methylpropane, which had previously been dried over activated 3 A molecular sieves, was added to the 500 mL sample cylinder. The sample cylinder was closed under nitrogen, and both the autoclave and sample cylinder were removed from the glovebox. Nitrogen and any other gaseous compounds were removed from the autoclave by evacuation using standard Schlenk techniques on a Schlenk line. The sample cylinder was charged with 165 g of n-butane. The autoclave was charged with 113 g of the n-butane/2-chloro-2-methylpropane stock solution at room temperature. The initial temperature and pressure were 27° C. and 60 psi (0.41 MPa). The reaction mixture was set to stir at 1700 rpm while the autoclave was heated to 100° C. It took 1 h to reach temperature, and the pressure was 320 psi (2.21 MPa). After a total of 19.4 h, the pressure was 360 psi (2.48 MPa) within the autoclave. At this time, the reaction mixture was analyzed by GC. In order to analyze the paraffinic layer, the stirring was stopped, and the product was allowed to settle for 5 minutes. An aliquot was sampled directly from the liquid contained within the sample cylinder was pressurized with nitrogen to about 300 psi (2.07 MPa) and was then analyzed offline using an analogous method. The results of the run are shown in Table 26 and were obtained using the UOP690 method. The mass ratio of liquid catalyst to hydrocarbon feed was 0.57, and the volume ratio was 0.24 using the following densities: 1.34 g/mL for the liquid catalyst and 0.57 g/mL for n-butane. The mass reaction rate was 4, and the volume reaction rate was 9 after 19.4 h.

TABLE 26

Isomerization and disproportionation of n-butane feed at 100° C., 1700 rpm, Hastelloy C autoclave, wt % of feed and reaction mixture

| time (h) | C3P | iC4 | nC4 | iC5 | nC5 | C6P | C7P | C8P | nC4-nC5[a] | nC5-nC6[a] | nC8-nC9[a] | nC9-nC10[a] | nC10+[a] | iC4/nC4 |
|---|---|---|---|---|---|---|---|---|---|---|---|---|---|---|
| 0.0 | 0.01 | 0.17 | 99.71 | 0.00 | 0.00 | 0.00 | 0.00 | 0.00 | 0.10 | 0.00 | 0.00 | 0.00 | 0.00 | 0.00 |
| 19.4 | 0.34 | 33.54 | 58.91 | 4.10 | 1.09 | 1.04 | 0.19 | 0.41 | 0.08 | 0.00 | 0.04 | 0.03 | 0.08 | 0.57 |

[a]Unknowns within these ranges

Example 22: nC4—Stir Rate at 1700 rpm with [1-butyl-3-methylimidazolium][Al₂Cl₇] in Hastelloy C Autoclave at 100° C.

A 300 mL Hastelloy C autoclave equipped with a Hastelloy C dipleg and Hastelloy B nut and connector, Hastelloy C baffle, and 75 mL stainless steel sample cylinder were dried in a 110° C. oven for at least 8 h. The dried autoclave and sample cylinder were brought into a nitrogen glovebox and allowed to cool to ambient temperature. The autoclave was charged with 55.391 g of [1-butyl-3-methylimidazolium][Al₂Cl₇] and the autoclave head was attached. 5.894 g of 2-chloro-2-methylpropane, which had previously been dried over activated 3 A molecular sieves, was added to the sample cylinder. The sample cylinder was closed under nitrogen, and both the autoclave and sample cylinder were removed from the glovebox. The autoclave was charged with 104 g of n-butane from a pressurized feed charger without displacing the nitrogen present in the autoclave. The composition of the n-butane feed is listed in Table 27, entry 1. The sample cylinder was charged with 15.25 g of n-butane from a pressurized feed charger without displacing the nitrogen present in the sample cylinder. The autoclave was heated to 100° C. with stirring at 100 rpm. Once the temperature was reached, stirring was stopped, and the 2-chloro-2-methylpropane/n-butane solution in the sample cylinder was added with an over-pressure of nitrogen. The nitrogen used to pressurize the charger and for all other work passed over a separate high surface sodium column. Once the addition was complete, stirring was set to 1700 rpm. Initially, the temperature increased to 102° C., and the pressure was 740 psi (5.10 MPa) within the autoclave. During the first 0.6 h, the temperature fluctuated from 98-102° C. After this time, the temperature stabilized at 100° C. and the initial pressure was 720 psi (4.96 MPa). After an additional 7.2 h, the pressure had increased to 830 psi (5.72 MPa), and the reaction mixture was analyzed by GC (entry 2. Table 27). In order to analyze the paraffinic layer, the stirring was stopped, and the product was allowed to settle for 5 minutes. An aliquot was sampled directly from the autoclave by opening a valve from the autoclave, passing the paraffinic layer through a $SiO_2$ column, and then passing it directly into a GC sample loop. The GC method employed was UOP690. Afterwards, a liquid sample was removed by filtering through a $SiO_2$ column into a sample cylinder. The liquid contained within the sample cylinder was pressurized with nitrogen to 300 psi (2.07 MPa) and was then analyzed offline using an analogous method. Once the stirring was recommenced, the temperature increased to 113° C., and, after 0.6 h, it stabilized at 100° C. with a pressure of 410 psi (2.83 MPa). The reaction was continued for an additional 14.5 h at this temperature, and the mixture was analyzed is a similar manner (entry 3. Table 27). Afterwards, the autoclave was cooled to ambient temperature, and a portion of the product was vented off. Fresh n-butane was added to the partially emptied autoclave. The composition of this new mixture is shown in entry 4. Table 27. The autoclave was then heated back to 100° C. with stirring at 1700 rpm, which took 1 h to achieve, and the pressure was 300 psi (2.07 MPa). After an additional 16.9 h of reaction, the product was analyzed. The results of the nm are shown in Table 27 and were determined using the UOP690 method online. The mass ratio of liquid catalyst to hydrocarbon feed was 0.51 and the volume ratio was 0.22 using the following densities: 1.34 g/mL for the liquid catalyst and 0.57 g/mL for n-butane. The mass reaction rate was 15, and the volume reaction rate was 35 after 7.8 h.

and removed from the glovebox. Nitrogen and any other gaseous compounds were removed from the autoclave by evacuation using standard Schlenk techniques and a Schlenk line. The autoclave was charged with 2.5 g of anhydrous HCl at ambient temperature. Afterwards, 123 g of n-butane was added to the autoclave from a pressurized feed charger. The reaction mixture was set to stir at 1700 rpm, and the autoclave was heated to 100° C. with stirring at 1700 rpm. It took 1.2 h to reach temperature, and the initial pressure was 460 psi (3.17 MPa). After a total of 4.8 h, the pressure was 440 psi (3.03 MPa) within the autoclave, and an aliquot was removed for GC analysis. In order to analyze the paraffinic layer, the stirring was stopped, and the product was allowed to settle for 5 minutes. An aliquot was sampled directly from the autoclave by opening a valve from the autoclave, passing the paraffinic layer through a $SiO_2$ column, and then passing it directly into a GC sample loop. The GC method employed was UOP690 (entry 2. Table 28). Entry 1 in Table 28 is the composition of the butane feed. Afterwards, a liquid sample was removed by filtering through a $SiO_2$ column into a sample cylinder. The liquid contained within the sample cylinder was pressurized with nitrogen to 300 psi (2.07 MPa) and was then analyzed offline using an analogous method. Afterwards, stirring was set to 1700 rpm, and the pressure was 320 psi (2.21 MPa). The reaction was continued for an additional 17.0 h the pressure was 320 psi (2.21 MPa) and had not increased. The reaction temperature was increased to 120° C.; it took 1 h to reach temperature. At this temperature, the pressure within the autoclave was 510 psi (3.52 MPa). The reaction was stirred at this temperature for 3.9 h, and the pressure had increased to 530 psi (3.65 MPa). The temperature was then increased to 130° C. It took 0.5 h to reach temperature, and the reaction was allowed to continue at that temperature for an additional 2.7 h. Afterwards, the temperature was decreased to 100° C.; it took 0.7 h to reach temperature. After maintaining the temperature at 100° C. for 0.1 h, the pressure within the autoclave was 350 psi (2.41 MPa), and the product mixture was analyzed in a similar manner (entry 3, Table 28), as discussed above. Afterwards, stirring was set to 1700 rpm, and the reaction mixture heated to 120° C. It took 1.1 h to

TABLE 27

Isomerization and disproportionation of n-butane at 100° C., 1700 rpm, Hastelloy C autoclave, wt. % of feed and reaction mixture

| Entry | time (h) | C3P | iC4 | nC4 | iC5 | nC5 | C6P | C7P | C8P | nC4-nC5[a] | nC5-nC6[a] | nC8-nC9[a] | nC9-nC10[a] | nC10+[a] | iC4/nC4 |
|---|---|---|---|---|---|---|---|---|---|---|---|---|---|---|---|
| 1 | 0.0 | 0.01 | 0.17 | 99.71 | 0.00 | 0.00 | 0.00 | 0.00 | 0.00 | 0.10 | 0.00 | 0.00 | 0.00 | 0.00 | 0.00 |
| 2 | 7.8 | 0.97 | 52.69 | 39.89 | 4.18 | 1.13 | 0.62 | 0.07 | 0.23 | 0.12 | 0.00 | 0.00 | 0.00 | 0.05 | 1.32 |
| 3 | 22.9 | 1.38 | 57.72 | 33.11 | 5.19 | 1.41 | 0.70 | 0.05 | 0.18 | 0.12 | 0.00 | 0.00 | 0.00 | 0.07 | 1.74 |
| 4 | 22.9 | 0.66 | 31.01 | 64.14 | 3.03 | 0.75 | 0.35 | 0.00 | 0.01 | 0.00 | 0.00 | 0.00 | 0.00 | 0.00 | 0.48 |
| 5 | 40.8 | 0.72 | 50.72 | 42.75 | 3.75 | 1.02 | 0.48 | 0.04 | 0.19 | 0.12 | 0.00 | 0.02 | 0.01 | 0.07 | 1.19 |

[a]Unknowns within these ranges

Example 23: nC4—Stir Rate at 1700 rpm with [1-butyl-3-methylimidazolium][$Al_2Cl_7$] in Hastelloy C Autoclave at 100° C. Using HCl A 300 mL Hastelloy C autoclave equipped with a Hastelloy C dipleg and Hastelloy B nut and connector, and Hastelloy C baffle were dried in a 110° C. oven for at least 8 h. The dried autoclave and sample cylinder were brought into a nitrogen glovebox and allowed to cool to ambient temperature. The autoclave was charged with 55.390 g of [1-butyl-3-methylimidazolium][$Al_2Cl_7$], and the autoclave head was attached. The autoclave was closed under nitrogen reach temperature, and the pressure at this temperature was 500 psi (3.45 MPa). The reaction mixture was allowed to continue to react at this temperature for an additional 13.5 h. At this time, the pressure within the autoclave was 510 psi (3.52 MPa). The reaction mixture was then cooled to 24° C. and analyzed by GC (entry 4, Table 28). The results of the run are shown in Table 28 and were determined using the UOP690 method online. The mass ratio of liquid catalyst to hydrocarbon feed was 0.47, and the volume ratio was 0.20 using the following densities: 1.34 g/mL for the liquid catalyst and 0.57 g/mL for n-butane. The mass reaction rate was 3, and the volume reaction rate was 8 after 4.8 h.

TABLE 28

Isomerization and disproportionation of n-butane at 100-130° C. Using HCl, 1700 rpm, Hastelloy C autoclave, wt. % of feed and reaction mixture

| Entry | time (h) | C3P | iC4 | nC4 | iC5 | nC5 | C6P | C7P | C8P | nC4-nC5[a] | nC5-nC6[a] | nC8-nC9[a] | nC9-nC10[a] | nC10+[a] | iC4/nC4 | % C4P Conv. |
|---|---|---|---|---|---|---|---|---|---|---|---|---|---|---|---|---|
| 1 | 0.0 | 0.01 | 0.17 | 99.71 | 0.00 | 0.00 | 0.00 | 0.00 | 0.00 | 0.10 | 0.00 | 0.00 | 0.00 | 0.00 | 0.00 | 0 |
| 2 | 4.8 | 0.01 | 7.37 | 92.45 | 0.00 | 0.00 | 0.00 | 0.00 | 0.00 | 0.16 | 0.00 | 0.00 | 0.00 | 0.00 | 0.08 | 7 |
| 3 | 30.7 | 0.34 | 57.95 | 40.95 | 0.46 | 0.13 | 0.00 | 0.00 | 0.02 | 0.12 | 0.00 | 0.00 | 0.00 | 0.00 | 1.42 | 59 |
| 4 | 45.3 | 2.11 | 59.83 | 33.93 | 3.00 | 0.82 | 0.13 | 0.00 | 0.00 | 0.12 | 0.00 | 0.00 | 0.00 | 0.00 | 1.76 | 66 |

[a]Unknowns within these ranges

Example 24: GC Method and Procedure for Offline Analysis

The sample cylinder containing the hydrocarbon product was positioned so that it was held vertically in a hood or well-vented area and connected to the GC by means of 1/16" stainless steel capillary tubing. The capillary tubing led to an LPG injection valve with a 0.5 µL sample loop. The exit of the injection valve used 1/8" translucent FEP Teflon rated to 500 psig, which was connected to a shutoff valve, which then led to a vent. The injection valve was put into the fill position, and the vent shut-off valve was closed. The bottom valve on the sample cylinder was opened, and the vent shut-off valve was partially opened to permit the flow of the hydrocarbon product. Once the entrained bubbles are no longer observed in the translucent tubing, the vent shut-off valve was closed. The sample was injected immediately by switching the injection valve to the injection position, and starting the integrator and the column temperature programming sequence. The injection valve remains in the inject position for the duration of the sample run. The valve on the sample cylinder was immediately closed, and the vent shut-off valve was opened to vent the sampling system. The GC column used was a 100 m 0.25 mm ID fused silica capillary column, internally coated to a film thickness of 0.5 µm with crosslinked dimethyl polysiloxane, Petrocol DH, Supelco. Cat. No. 24160-U. The GC method used a flame ionization detector. The carrier gas was hydrogen and operated in the constant pressure mode at an equivalent flow at 34° C. of 2.3 mL/min. The split flow rate was 200 mL/min, and the injection port temperature was 215° C. The initial column temperature was 34° C., and it was held for 15 minutes at this temperature. The temperature was then ramped to 75° C. at 8° C./min ramp rate and held at 75° C. for 15 minutes. The temperature was then ramped to 250° C. at 20° C./min ramp rate and held at 250° C. for 22 minutes. The detector temperature was 250° C. with a hydrogen flow rate of 30 mL/min and an air flow rate of 400 mL/min. The makeup gas can be either nitrogen or helium and was set at 30 mL/min. There were 76 components identified.

Example 25: Modification of the GC Method Used for Analysis of the Reaction with the FT Wax The GC method used to quantify the products from the reaction with the FT wax was a modification of the UOP690 method used for online analysis. The inlet temperature was increased to 265° C., and the run time and temperature were increased. At the end of the temperature program employed in the UOP690 method, instead of ending the run, the temperature was increased to 315° C. at a ramp rate of 20° C./min and held at that temperature for 35 minutes.

Example 26: nC4/nC7—Stir Rate at 1700 rpm with [1-butyl-3-methylimidazolium][Al$_2$Cl$_7$] in Hastelloy C Autoclave at 100° C.

A 300 mL Hastelloy C autoclave equipped with a Hastelloy C dipleg and Hastelloy B nut and connector, Hastelloy C baffle, and 75 mL stainless steel sample cylinder were dried in a 110° C. oven for at least 8 h. The dried autoclave and sample cylinder were brought into a nitrogen glovebox and allowed to cool to ambient temperature. The autoclave was charged with 38.339 g of [1-butyl-3-methylimidazolium][Al$_2$Cl$_7$], and the autoclave head was attached. The 75 mL sample cylinder was charged with 4.024 g of 2-chloro-2-methylpropane, and 12.228 g of n-heptane, both compounds having previously been dried over activated 3 A molecular sieves. The sample cylinder was closed under nitrogen, and both the autoclave and sample cylinder were removed from the glovebox. The autoclave was charged with 111 g of n-butane from a pressurized feed charger without displacing the nitrogen present in the autoclave. The composition of the n-butane feed is listed in Table 29, entry 1. The autoclave was heated to 100° C. with stirring at 100 rpm. Once the temperature was reached, stirring was stopped, and the 2-chloro-2-methylpropane-heptane solution in the sample cylinder was added with an over-pressure of nitrogen. The nitrogen used to pressurize the charger and for all other work passed over a separate high surface sodium column. Once the addition was complete, stirring was set to 1700 rpm. Initially, the temperature increased to 110° C., and the pressure was 460 psi (3.17 MPa) within the autoclave. After 8 minutes of stirring, the temperature decreased to 105° C., and the pressure was 360 psi (2.48 MPa). After 8 minutes, stirring was stopped and the paraffinic layer was analyzed by online and offline GC. In order to analyze the paraffinic layer with online GC, the stirring was stopped, and the product was allowed to settle for 5 minutes. An aliquot was sampled directly from the autoclave by opening a valve from the autoclave, passing the paraffinic layer through a SiO$_2$ column, and then passing it directly into a GC sample loop. The GC method employed was UOP690. Afterwards, a liquid sample was removed by filtering through a SiO$_2$ column into a sample cylinder for offline GC analysis. The liquid contained within the sample cylinder was pressurized with nitrogen to about 300 psi (2.07 MPa) and was then analyzed offline using an analogous method as described above. The reported results are those from the offline analysis and are depicted in Table 29. This procedure was repeated two more times and the results are reported in Table 29. After stirring was recommenced, the temperature stabilized at 100° C. after an additional 42 minutes of reaction. The mass ratio of liquid catalyst to hydrocarbon feed was 0.34, and the volume ratio was 0.15 using the following densities: 1.34 g/mL for the liquid catalyst, 0.684 g/mL for n-heptane and 0.57 g/mL for n-butane.

TABLE 29

Reverse disproportionation of an n-butane/n-heptane feed at 100° C., 1700 rpm, Hastelloy C autoclave, wt. % of feed and reaction mixture

| time (h) | C3P | iC4 | nC4 | iC5 | nC5 | C6P | C7P | C8P | Other[a] | C4P | C5P | iC4/nC4 | iC5/nC5 |
|---|---|---|---|---|---|---|---|---|---|---|---|---|---|
| NA | 0.01 | 0.17 | 99.71 | 0.00 | 0.00 | 0.00 | 0.00 | 0.00 | 0.11 | 99.88 | 0.00 | 0.00 | NA |
| 0.0[b] | 0.0 | 0.0 | 90.1 | 0.0 | 0.0 | 0.0 | 9.9 | 0.0 | 0.0 | 90.1 | 0.0 | 0.0 | NA |
| 0.1 | 0.71 | 12.67 | 73.35 | 4.15 | 0.67 | 1.81 | 5.83 | 0.38 | 0.43 | 86.02 | 4.82 | 0.17 | 6.19 |
| 4.5 | 2.36 | 40.53 | 38.24 | 10.74 | 2.83 | 3.60 | 0.81 | 0.49 | 0.40 | 78.77 | 13.57 | 1.06 | 3.80 |
| 17.6 | 5.25 | 50.62 | 26.53 | 10.77 | 2.77 | 2.89 | 0.37 | 0.23 | 0.57 | 77.15 | 13.54 | 1.91 | 3.89 |

[a]Other compounds present,
[b]wt. % composition at t = 0 h is based on mass of added reagents Example 27: nC4/nC9—Stir Rate at 1700 rpm with [1-butyl-3-methylimidazolium][Al$_2$Cl$_7$] in Hastelloy C Autoclave at 100° C.

A 300 mL Hastelloy C autoclave equipped with a Hastelloy C dipleg and Hastelloy B nut and connector, Hastelloy C baffle, and 75 mL stainless steel sample cylinder were dried in a 110° C. oven for at least 8 h. The dried autoclave and sample cylinder were brought into a nitrogen glovebox and allowed to cool to ambient temperature. The autoclave was charged with 38.34 g of [1-butyl-3-methylimidazolium][Al$_2$Cl$_7$], and the autoclave head was attached. The 75 mL sample cylinder was charged with 4.02 g of 2-chloro-2-methylpropane and 15.65 g of n-nonane, both compounds having previously been dried over activated 3 A molecular sieves. The sample cylinder was closed under nitrogen, and both the autoclave and sample cylinder were removed from the glovebox. The autoclave was charged with 111 g of n-butane from a pressurized feed charger without displacing the nitrogen present in the autoclave. The composition of the n-butane feed is listed in Table 30, entry 1. The autoclave was heated to 100° C. with stirring at 100 rpm. Once the temperature was reached, stirring was stopped, and the 2-chloro-2-methylpropane/n-nonane solution in the sample cylinder was added with an over-pressure of nitrogen. The nitrogen used to pressurize the charger and for all other work passed over a separate high surface sodium column. Once the addition was complete, stirring was set to 1700 rpm. Initially, the temperature increased to 105° C., and the pressure was 520 psi (3.58 MPa) within the autoclave. After 9 minutes of stirring, the temperature decreased to 101° C., and the pressure was 355 psi (2.45 MPa). After 9 minutes, stirring was stopped, and the paraffinic layer was analyzed by online and offline GC. In order to analyze the paraffinic layer with online GC, the stirring was stopped, and the product was allowed to settle for 5 minutes. An aliquot was sampled directly from the autoclave by opening a valve from the autoclave, passing the paraffinic layer through a SiO$_2$ column, and then passing it directly into a GC sample loop. The GC method employed was UOP690. Afterwards, a liquid sample was removed by filtering through a SiO$_2$ column into a sample cylinder for offline GC analysis. The liquid contained within the sample cylinder was pressurized with nitrogen to about 300 psi (2.07 MPa) and was then analyzed offline using an analogous method as described above. The reported results are those from the offline analysis and are depicted in Table 30. This procedure was repeated two more times and the results are reported in Table 30. After stirring was recommenced, the temperature stabilized at 100° C. after an additional 27 minutes of reaction. The mass ratio of liquid catalyst to hydrocarbon feed was 0.33, and the volume ratio was 0.14 using the following densities: 1.34 g/mL for the liquid catalyst, 0.718 g/mL for n-nonane and 0.57 g/mL for n-butane.

TABLE 30

Reverse disproportionation of an n-butane/n-nonane feed at 100° C., 700 rpm, Hastelloy C autoclave, wt. % of feed and reaction mixture

| time (h) | C3P | iC4 | nC4 | iC5 | nC5 | C6P | C7P | C8P | nC9 | C9+ | Other[a] | C4P | C5P | iC4/nC4 | iC5/nC5 |
|---|---|---|---|---|---|---|---|---|---|---|---|---|---|---|---|
| NA | 0.01 | 0.17 | 99.71 | 0.00 | 0.00 | 0.00 | 0.00 | 0.00 | 0.00 | 0.00 | 0.11 | 99.88 | 0.00 | 0.00 | NA |
| 0.0[b] | 0.0 | 0.0 | 87.6 | 0.0 | 0.0 | 0.0 | 0.0 | 0.0 | 12.4 | 0.00 | 0.0 | 90.1 | 0.0 | 0.0 | NA |
| 0.2 | 0.43 | 13.31 | 71.62 | 5.27 | 0.76 | 2.04 | 0.86 | 0.57 | 4.14 | 0.59 | 0.41 | 84.93 | 6.03 | 0.18 | 6.93 |
| 4.6 | 1.68 | 37.39 | 39.82 | 11.60 | 2.95 | 4.23 | 1.04 | 0.67 | 0.04 | 0.28 | 0.30 | 77.21 | 14.55 | 0.94 | 3.93 |
| 21.1 | 3.38 | 48.92 | 27.50 | 11.82 | 3.05 | 3.97 | 0.59 | 0.35 | 0.01 | 0.19 | 0.22 | 76.42 | 14.87 | 1.78 | 3.88 |

[a]Other compounds present,
[b]wt. % composition at t = 0 h is based on mass of added reagents Example 28: nC4/nC9—Stir Rate at 1700 rpm with [1-butyl-3-methylimidazolium][Al$_2$Cl$_7$] in Hastelloy C Autoclave at 100° C.

A 300 mL Hastelloy C autoclave equipped with a Hastelloy C dipleg and Hastelloy B nut and connector, Hastelloy C baffle, and 75 mL stainless steel sample cylinder were dried in a 110° C. oven for at least 8 h. The dried autoclave and sample cylinder were brought into a nitrogen glovebox and allowed to cool to ambient temperature. The autoclave was charged with 38.341 g of [1-butyl-3-methylimidazolium][Al$_2$Cl$_7$], and the autoclave head was attached. The 75 mL sample cylinder was charged with 4.038 g of 2-chloro-2-methylpropane and 43.003 g of n-nonane, both compounds having previously been dried over activated 3 A molecular sieves. The sample cylinder was closed under nitrogen, and both the autoclave and sample cylinder were removed from the glovebox. The autoclave was charged with 89 g of n-butane from a pressurized feed charger without displacing the nitrogen present in the autoclave. The composition of the n-butane feed is listed in Table 31, entry 1. The autoclave was heated to 100° C. with stirring at 100 rpm. Once the temperature was reached, stirring was stopped, and the 2-chloro-2-methylpropane/n-nonane solution in the sample cylinder was added with an over-pressure of nitrogen. The nitrogen used to pressurize the charger and for all other work passed over a separate high surface sodium column. Once the addition was complete, stirring was set to 1700 rpm. Initially, the temperature increased to 114° C., and the pressure was 505 psi (3.48 MPa) within the autoclave. After 7 minutes of stirring, the temperature decreased to 106° C., and the pressure was 400 psi (2.76 MPa). After 7 minutes, stirring was stopped, and the paraffinic layer was analyzed by online and offline GC. In order to analyze the paraffinic layer with online GC, the stirring was stopped, and the product was allowed to settle for 5 minutes. An aliquot was sampled directly from the autoclave by opening a valve from the autoclave, passing the paraffinic layer through a $SiO_2$ column, and then passing it directly into a GC sample loop. The GC method employed was UOP690. Afterwards, a liquid sample was removed by filtering through a $SiO_2$ column into a sample cylinder for offline GC analysis. The liquid contained within the sample cylinder was pressurized with nitrogen to about 300 psi (2.07 MPa) and was then analyzed offline using an analogous method as described above. The reported results are those from the offline analysis and are depicted in Table 31. This procedure was repeated two more times and the results are reported in Table 31. After stirring was recommenced, the temperature stabilized at 100° C. after an additional 18 minutes of reaction. The mass ratio of liquid catalyst to hydrocarbon feed was 0.32, and the volume ratio was 0.15 using the following densities: 1.34 g/mL for the liquid catalyst, 0.718 g/mL for n-nonane and 0.57 g/mL for n-butane.

C baffle, and 150 mL stainless steel sample cylinder were dried in a 110° C. oven for at least 8 h. The dried autoclave and sample cylinder were brought into a nitrogen glovebox and allowed to cool to ambient temperature. The autoclave was charged with 38.34 g of [1-butyl-3-methylimidazolium][$Al_2Cl_7$], and the autoclave head was attached. The 150 mL sample cylinder was charged with 4.02 g of 2-chloro-2-methylpropane and 87.82 g of n-nonane, both compounds having previously been dried over activated 3 A molecular sieves. The sample cylinder was closed under nitrogen, and both the autoclave and sample cylinder were removed from the glovebox. The autoclave was charged with 60 g of n-butane from a pressurized feed charger without displacing the nitrogen present in the autoclave. The composition of the n-butane feed is listed in Table 32, entry 1. The autoclave was heated to 100° C. with stirring at 100 rpm. Once the temperature was reached, stirring was stopped, and the 2-chloro-2-methylpropane/n-nonane solution in the sample cylinder was added with an over-pressure of nitrogen. The nitrogen used to pressurize the charger and for all other work passed over a separate high surface sodium column. Once the addition was complete, stirring was set to 1700 rpm. Initially, the temperature increased to 109° C., and the pressure was 460 psi (3.17 MPa) within the autoclave. After 7 minutes of stirring, the temperature decreased to 104° C., and the pressure was 440 psi (3.03 MPa). After 7 minutes, stirring was stopped, and the paraffinic layer was analyzed by online and offline GC. In order to analyze the paraffinic layer with online GC, the stirring was stopped, and the product was allowed to settle for 5 minutes. An aliquot was sampled directly from the autoclave by opening a valve from the autoclave, passing the paraffinic layer through a $SiO_2$ column, and then passing it directly into a GC sample loop. The GC method employed was UOP690. Afterwards, a liquid sample was removed by filtering through a $SiO_2$ column into a sample cylinder for offline GC analysis. The liquid contained within the sample cylinder was pressurized with nitrogen to about 300 psi (2.07 MPa) and was then analyzed offline using an analogous method as described above. The reported results are those from the offline analysis and are depicted in Table 32. This procedure was repeated two more times and the results are reported in Table

TABLE 31

Reverse disproportionation of an n-butane/n-nonane feed at 100° C., 1700 rpm, Hastelloy C autoclave, wt. % of feed and reaction mixture

| time (h) | C3P | iC4 | nC4 | iC5 | nC5 | C6P | C7P | C8P | nC9 | C9+ | Other[a] | C4P | C5P | iC4/nC4 | iC5/nC5 |
|---|---|---|---|---|---|---|---|---|---|---|---|---|---|---|---|
| NA | 0.01 | 0.17 | 99.71 | 0.00 | 0.00 | 0.00 | 0.00 | 0.00 | 0.00 | 0.00 | 0.11 | 99.88 | 0.00 | 0.00 | NA |
| 0.0[b] | 0.0 | 0.0 | 67.4 | 0.0 | 0.0 | 0.0 | 0.0 | 0.0 | 32.6 | 0.00 | 0.0 | 67.4 | 0.0 | 0.0 | NA |
| 0.1 | 0.54 | 11.31 | 59.02 | 6.45 | 0.82 | 3.03 | 1.35 | 0.82 | 14.76 | 1.37 | 0.53 | 70.33 | 7.27 | 0.19 | 7.87 |
| 4.6 | 1.03 | 21.34 | 45.76 | 12.49 | 2.16 | 6.37 | 2.62 | 1.29 | 4.64 | 1.59 | 0.71 | 67.1 | 14.65 | 0.47 | 5.78 |
| 23.4 | 1.34 | 27.88 | 37.76 | 15.04 | 3.35 | 7.74 | 2.77 | 1.24 | 0.90 | 1.34 | 0.64 | 65.64 | 18.39 | 0.74 | 4.49 |

[a]Other compounds present,
[b]wt. % composition at t = 0 h is based on mass of added reagents Example 29: nC4/nC9—Stir Rate at 1700 rpm with [1-butyl-3-methylimidazolium][$Al_4Cl_7$] in Hastelloy C Autoclave at 100° C.

A 300 mL Hastelloy C autoclave equipped with a Hastelloy C dipleg and Hastelloy B nut and connector. Hastelloy 32. After stirring was recommenced, the temperature stabilized at 100° C. after an additional 38 minutes of reaction. The mass ratio of liquid catalyst to hydrocarbon feed was 0.29, and the volume ratio was 0.14 using the following densities: 1.34 g/mL for the liquid catalyst, 0.718 g/mL for n-nonane and 0.57 g/mL for n-butane.

TABLE 32

Reverse disproportionation of an n-butane/n-nonane feed at 100° C., 1700 rpm, Hastelloy C autoclave, wt. % of feed and reaction mixture

| time (h) | C3P | iC4 | nC4 | iC5 | nC5 | C6P | C7P | C8P | nC9 | C9+ | Other[a] | C4P | C5P | iC4/nC4 | iC5/nC5 |
|---|---|---|---|---|---|---|---|---|---|---|---|---|---|---|---|
| NA | 0.01 | 0.17 | 99.71 | 0.00 | 0.00 | 0.00 | 0.00 | 0.00 | 0.00 | 0.00 | 0.11 | 99.88 | 0.00 | 0.00 | NA |
| 0.0[b] | 0.0 | 0.0 | 40.6 | 0.0 | 0.0 | 0.0 | 0.0 | 0.0 | 59.4 | 0.00 | 0.0 | 40.6 | 0.0 | 0.0 | NA |
| 0.1 | 0.33 | 7.72 | 38.45 | 5.77 | 0.58 | 3.08 | 1.58 | 0.95 | 38.61 | 2.16 | 0.77 | 46.17 | 6.35 | 0.20 | 9.95 |
| 4.7 | 0.56 | 12.03 | 35.91 | 9.05 | 1.06 | 5.04 | 2.55 | 1.44 | 28.22 | 3.23 | 0.91 | 47.94 | 10.11 | 0.34 | 8.54 |
| 22.8 | 0.60 | 13.44 | 35.82 | 9.92 | 1.23 | 5.62 | 2.79 | 1.50 | 24.69 | 3.46 | 0.93 | 49.26 | 11.15 | 0.38 | 8.07 |

[a] Other compounds present,
[b] wt. % composition at t = 0 h is based on mass of added reagents

Example 30: nC4/nC16—Stir Rate at 1700 rpm with [1-butyl-3-methylimidazolium][Al$_2$Cl$_7$] in Hastelloy C Autoclave at 100° C.

A 300 mL Hastelloy C autoclave equipped with a Hastelloy C dipleg and Hastelloy B nut and connector, Hastelloy C baffle, and 75 mL stainless steel sample cylinder were dried in a 110° C. oven for at least 8 h. The dried autoclave and sample cylinder were brought into a nitrogen glovebox and allowed to cool to ambient temperature. The autoclave was charged with 38.34 g of [1-butyl-3-methylimidazolium][Al$_2$Cl$_7$], and the autoclave head was attached. The 75 mL sample cylinder was charged with 3.9 g of 2-chloro-2-methylpropane and 27.1 g of n-hexadecane, both compounds having previously been dried over activated 3 A molecular sieves. The sample cylinder was closed under nitrogen, and both the autoclave and sample cylinder were removed from the glovebox. The autoclave was charged with 111 g of n-butane from a pressurized feed charger without displacing the nitrogen present in the autoclave. The composition of the n-butane feed is listed in Table 33, entry 1. The autoclave was heated to 100° C. with stirring at 100 rpm. Once the temperature was reached, stirring was stopped, and the 2-chloro-2-methylpropane/n-hexadecane solution in the sample cylinder was added with an overpressure of nitrogen. The nitrogen used to pressurize the charger and for all other work passed over a separate high surface sodium column. Once the addition was complete, stirring was set to 1700 rpm. Initially, the temperature increased to 105° C., and the pressure was 650 psi (4.48 MPa) within the autoclave. After 18 minutes of stirring, the temperature decreased to 98° C., and the pressure was 490 psi (3.38 MPa). After 18 minutes, stirring was stopped and the paraffinic layer analyzed by online and offline GC. In order to analyze the paraffinic layer with online GC, the stirring was stopped, and the product was allowed to settle for 5 minutes. An aliquot was sampled directly from the autoclave by opening a valve from the autoclave, passing the paraffinic layer through a SiO$_2$ column, and then passing it directly into a GC sample loop. The GC method employed was UOP690. Afterwards, a liquid sample was removed by filtering through a SiO$_2$ column into a sample cylinder for offline GC analysis. The liquid contained within the sample cylinder was pressurized with nitrogen to about 300 psi (2.07 MPa) and was then analyzed offline using an analogous method as described above. The reported results are those from the offline analysis and are depicted in Table 33. This procedure was repeated two more times and the results are reported in Table 33. After stirring was recommenced, the temperature stabilized at 10° C. after an additional 40 minutes of reaction. The mass ratio of liquid catalyst to hydrocarbon feed was 0.30, and the volume ratio was 0.14 using the following densities: 1.34 g/mL for the liquid catalyst, 0.773 g/mL for n-hexadecane and 0.57 g/mL for n-butane.

TABLE 33

Reverse disproportionation of an n-butane/n-hexadecane feed at 100° C., 1700 rpm, Hastelloy C autoclave, wt. % of feed and reaction mixture

| time (h) | C3P | iC4 | nC4 | iC5 | nC5 | C6P | C7P | C8P | nC16 | C9+ | Other[a] | C4P | C5P | iC4/nC4 | iC5/nC5 |
|---|---|---|---|---|---|---|---|---|---|---|---|---|---|---|---|
| NA | 0.01 | 0.17 | 99.71 | 0.00 | 0.00 | 0.00 | 0.00 | 0.00 | 0.00 | 0.00 | 0.11 | 99.88 | 0.00 | 0.00 | NA |
| 0.0[b] | 0.0 | 0.0 | 80.4 | 0.0 | 0.0 | 0.0 | 0.0 | 0.0 | 19.6 | 0.00 | 0.0 | 80.4 | 0.0 | 0.0 | NA |
| 0.3 | 0.41 | 11.40 | 68.77 | 5.85 | 0.78 | 2.85 | 1.34 | 0.72 | 6.38 | 1.06 | 0.44 | 80.17 | 6.63 | 0.17 | 7.50 |
| 4.8 | 1.51 | 26.24 | 39.95 | 13.45 | 2.88 | 6.92 | 2.65 | 1.24 | 3.38 | 1.20 | 0.58 | 66.19 | 16.33 | 0.66 | 4.67 |
| 23.5 | 2.36 | 34.25 | 29.63 | 16.09 | 4.11 | 8.08 | 2.45 | 1.11 | 0.46 | 0.90 | 0.56 | 63.88 | 20.2 | 1.16 | 3.91 |

[a] Other compounds present,
[b] wt. % composition at t = 0 h is based on mass of added reagents

Example 31: nC4/nC7—Stir Rate at 1700 rpm with [1-butyl-3-methylimidazolium][Al$_2$Cl$_7$] in Hastelloy C Autoclave at 100° C.

A 300 mL Hastelloy C autoclave equipped with a Hastelloy C dipleg and Hastelloy B nut and connector, Hastelloy C baffle, and 75 mL stainless steel sample cylinder were dried in a 110° C. oven for at least 8 h. The dried autoclave and sample cylinder were brought into a nitrogen glovebox and allowed to cool to ambient temperature. The autoclave was charged with 38.342 g of [1-butyl-3-methylimidazolium][Al$_2$Cl$_7$], and the autoclave head was attached. The 75 mL sample cylinder was charged with 4.020 g of 2-chloro-2-methylpropane and 12.232 g of n-heptane, both compounds having previously been dried over activated 3 A molecular sieves. The sample cylinder was closed under nitrogen, and both the autoclave and sample cylinder were removed from the glovebox. The autoclave was charged with 113 g of n-butane from a pressurized feed charger without displacing the nitrogen present in the autoclave. The composition of the n-butane feed is listed in Table 34, entry 1. The autoclave was heated to 100° C. with stirring at 100 rpm. Once the temperature was reached, stirring was stopped, and the 2-chloro-2-methylpropane/n-heptane solution in the sample cylinder was added with an over-pressure of nitrogen. The nitrogen used to pressurize the charger and for all other work passed over a separate high surface sodium column. Once the addition was complete, stirring was set to 1700 rpm. Initially, the temperature increased to 101° C., and the pressure was 500 psi (3.45 MPa) within the autoclave. After 9 minutes of stirring, the temperature decreased to 99° C., and the pressure was 450 psi (3.10 MPa). After 9 minutes, stirring was stopped, and the paraffinic layer was analyzed by online and offline GC. In order to analyze the paraffinic layer with online GC, the stirring was stopped, and the product was allowed to settle for 5 minutes. An aliquot was sampled directly from the autoclave by opening a valve from the autoclave, passing the paraffinic layer through a $SiO_2$ column, and then passing it directly into a GC sample loop. The GC method employed was UOP690. Afterwards, a liquid sample was removed by filtering through a $SiO_2$ column into a sample cylinder for offline GC analysis. The liquid contained within the sample cylinder was pressurized with nitrogen to about 300 psi (2.07 MPa) and was then analyzed offline using an analogous method as described above. The reported results are those from the offline analysis and are depicted in Table 34. This procedure was repeated two more times and the results are reported in Table 34. After stirring was recommenced, the temperature stabilized at 100° C. after an additional 38 minutes of reaction. The mass ratio of liquid catalyst to hydrocarbon feed was 0.34, and the volume ratio was 0.15 using the following densities: 1.34 g/mL for the liquid catalyst, 0.684 g/mL for n-heptane and 0.57 g/mL for n-butane.

sample cylinder were brought into a nitrogen glovebox and allowed to cool to ambient temperature. The autoclave was charged with 38.341 g of [1-butyl-3-methylimidazolium][$Al_2Cl_7$], and the autoclave head was attached. The 75 mL sample cylinder was charged with 4.020 g of 2-chloro-2-methylpropane and 12.233 g of n-heptane, both compounds having previously been dried over activated 3 A molecular sieves. The sample cylinder was closed under nitrogen, and both the autoclave and sample cylinder were removed from the glovebox. The autoclave was charged with 86 g of propane from a pressurized feed charger, displacing the nitrogen present in the autoclave. The composition of the propane feed is listed in Table 35, entry 1. The autoclave was heated to about 90° C. with stirring at about 700 rpm. Stirring was then stopped, and the 2-chloro-2-methylpropane/n-heptane solution in the sample cylinder was added with an over-pressure of nitrogen. The nitrogen used to pressurize the charger and for all other work passed over a separate high surface sodium column. Once the addition was complete, stirring was set to 1700 rpm, and the mixture was heated to 110° C. It required 14 minutes to bring the mixture from the initial temperature of 96° C. to 110° C. The pressure increased from 950 psi (6.55 MPa) to 1460 psi (10.07 MPa) during this time. After 3.6 h, the temperature was decreased to 90° C., and the mixture was analyzed by online and offline (GC. In order to analyze the paraffinic layer with online GC, the stirring was stopped, and the product was allowed to settle for 5 minutes. An aliquot was sampled directly from the autoclave by opening a valve from the autoclave, passing the paraffinic layer through a $SiO_2$ column, and then passing it directly into a GC sample loop. The GC method employed was UOP690. Afterwards, a liquid sample was removed by filtering through a $SiO_2$ column into a sample cylinder for offline GC analysis. The liquid contained within the sample cylinder was pressurized with nitrogen to about 300 psi (2.07 MPa) and was then analyzed offline using an analogous method as described above. The reported results are those from the offline analy-

TABLE 34

Reverse disproportionation of an n-butane/n-heptane feed at 100° C., 1700 rpm, Hastelloy C autoclave, wt. % of feed and reaction mixture

| time (h) | C3P | iC4 | nC4 | iC5 | nC5 | C6P | C7P | C8P | Other[a] | C4P | C5P | iC4/nC4 | iC5/nC5 |
|---|---|---|---|---|---|---|---|---|---|---|---|---|---|
| NA | 0.01 | 0.17 | 99.71 | 0.00 | 0.00 | 0.00 | 0.00 | 0.00 | 0.11 | 99.88 | 0.00 | 0.00 | NA |
| 0.0[b] | 0.0 | 0.0 | 90.2 | 0.0 | 0.0 | 0.0 | 9.8 | 0.0 | 0.0 | 90.1 | 0.0 | 0.0 | NA |
| 0.2 | 0.63 | 13.31 | 73.09 | 4.25 | 0.64 | 1.82 | 5.37 | 0.39 | 0.50 | 86.40 | 4.89 | 0.18 | 6.64 |
| 4.6 | 2.66 | 41.61 | 37.75 | 10.33 | 2.70 | 3.36 | 0.76 | 0.44 | 0.39 | 79.36 | 13.03 | 1.10 | 3.83 |

[a]Other compounds present,
[b]wt. % composition at t = 0 h is based on mass of added reagents Example 32: C3P/nC7—Stir Rate at 1700 rpm with [1-butyl-3-methylimidazolium][$Al_2Cl_7$] in Hastelloy C Autoclave at 110° C.

A 300 mL Hastelloy B autoclave equipped with a Hastelloy B dipleg and Hastelloy B nut and connector, Hastelloy B baffle, and 75 mL stainless steel sample cylinder were dried in a 110°: oven for at least 8 h. The dried autoclave and sis and are depicted in Table 7. The reaction mixture was then reheated to 110° C. which took 1.7 h to stabilize at 110° C., and allowed to keep reacting. This procedure was repeated one more time and the results are reported in Table 35. The mass ratio of liquid catalyst to hydrocarbon feed was 0.43, and the volume ratio was 0.16 using the following densities: 1.34 g/mL for the liquid catalyst, 0.684 g/mL for n-heptane and 0.49 g/mL for propane.

TABLE 35

Reverse disproportionation of a propane/n-heptane feed at 110° C., 1700 rpm, Hastelloy B autoclave, wt. % of feed and reaction mixture

| time (h) | C3P | iC4 | nC4 | iC5 | nC5 | C6P | C7P | C8P | Other[a] | C4P | C5P | iC4/nC4 | iC5/nC5 |
|---|---|---|---|---|---|---|---|---|---|---|---|---|---|
| NA | 99.25 | 0.06 | 0.00 | 0.08 | 0.00 | 0.61 | 0.00 | 0.00 | 0.00 | 0.06 | 0.08 | NA | NA |
| 0.0[b] | 88.0 | 0.0 | 0.0 | 0.0 | 0.0 | 0.0 | 12.0 | 0.0 | 0.0 | 0.0 | 0.0 | NA | NA |
| 3.6 | 86.80 | 6.07 | 2.30 | 2.44 | 0.64 | 1.16 | 0.46 | 0.04 | 0.09 | 8.37 | 3.08 | 2.64 | 3.81 |
| 21.4 | 85.59 | 7.27 | 3.85 | 1.84 | 0.52 | 0.69 | 0.10 | 0.00 | 0.14 | 11.12 | 2.36 | 1.89 | 3.54 |

[a]Other compounds present,
[b]wt. % composition at t = 0 h is based on mass of added reagents Example 33: nC4/nC5—Stir Rate at 1700 rpm with [1-butyl-3-methylimidazolium][Al$_2$Cl$_7$] in Hastelloy C Autoclave at 100° C.

A 300 mL Hastelloy B autoclave equipped with a Hastelloy B dipleg and Hastelloy B nut and connector, Hastelloy B baffle, and 75 mL stainless steel sample cylinder were dried in a 110° C. oven for at least 8 h. The dried autoclave and sample cylinder were brought into a nitrogen glovebox and allowed to cool to ambient temperature. The autoclave was charged with 38.34 g of [1-butyl-3-methylimidazolium] [Al$_2$Cl$_7$], and the autoclave head was attached. The 75 mL sample cylinder was charged with 4.02 g of 2-chloro-2-methylpropane and 9.44 g of n-pentane, both compounds having previously been dried over activated 3 A molecular sieves. The sample cylinder was closed under nitrogen, and both the autoclave and sample cylinder were removed from the glovebox. The autoclave was charged with 43 g of n-butane from a pressurized feed charger, without displacing the nitrogen present in the autoclave. The composition of the n-butane feed is listed in Table 36, entry 1. The autoclave was then charged with 92 g of n-pentane from a pressurized feed charger, which passed over a high surface sodium drier, without displacing the nitrogen. The autoclave was heated to 100° C. with stirring at 100 rpm. Once the temperature was achieved, stirring was stopped, and the 2-chloro-2-methylpropane/n-pentane solution in the sample cylinder was added with an over-pressure of nitrogen. The nitrogen used to pressurize the charger and for all other work passed over a separate high surface sodium column. Once the addition was complete, stirring was set to 1700 rpm. Initially, the temperature increased to 105° C., and the pressure was 1240 psi (8.55 MPa) within the autoclave. After 20 minutes of stirring, the temperature decreased to 100° C., and the pressure was 1050 psi (7.24 MPa). After 20 minutes, stirring was stopped, and the paraffinic layer was analyzed by online and offline GC. In order to analyze the paraffinic layer with online GC, the stirring was stopped, and the product was allowed to settle for 5 minutes. An aliquot was sampled directly from the autoclave by opening a valve from the autoclave, passing the paraffinic layer through a SiO$_2$ column, and then passing it directly into a GC sample loop. The GC method employed was UOP690. Afterwards, a liquid sample was removed by filtering through a SiO$_2$ column into a sample cylinder for offline GC analysis. The liquid contained within the sample cylinder was pressurized with nitrogen to about 300 psi (2.07 MPa) and was then analyzed offline using an analogous method as described above. The reported results are those from the offline analysis and are depicted in Table 36. This procedure was repeated one more time and the results are reported in Table 36. The mass ratio of liquid catalyst to hydrocarbon feed was 0.29, and the volume ratio was 0.13 using the following densities: 1.34 g/mL for the liquid catalyst, 0.626 g/mL for n-pentane and 0.57 g/mL for n-butane.

TABLE 36

Disproportionation/reverse disproportionation of an n-butane/n-pentane feed at 100° C., 1700 rpm, Hastelloy B autoclave, wt. % of feed and reaction mixture

| time (h) | C3P | iC4 | nC4 | iC5 | nC5 | C6P | C7P | C8P | Other[a] | C4P | C5P | iC4/nC4 | iC5/nC5 |
|---|---|---|---|---|---|---|---|---|---|---|---|---|---|
| NA | 0.01 | 0.17 | 99.71 | 0.00 | 0.00 | 0.00 | 0.00 | 0.00 | 0.11 | 99.88 | 0.00 | 0.00 | NA |
| 0.0[b] | 0.0 | 0.0 | 30.0 | 0.0 | 70.0 | 0.0 | 0.0 | 0.0 | 0.0 | 30.0 | 70.0 | 0.00 | NA |
| 0.3 | 0.72 | 14.79 | 22.71 | 15.64 | 33.98 | 7.65 | 2.43 | 0.79 | 1.29 | 37.50 | 49.62 | 0.65 | 0.46 |
| 23.6 | 4.01 | 33.20 | 18.26 | 18.39 | 5.37 | 12.51 | 4.00 | 1.77 | 2.49 | 51.46 | 23.76 | 1.82 | 3.42 |

[a]Other compounds present,
[b]wt. % composition at t = 0 h is based on mass of added reagents Example 34: nC6 Isomerization and Disproportionation—Stir Rate at 1700 rpm with [1-butyl-3-methylimidazolium][Al$_2$Cl$_7$] in Hastelloy B Autoclave at 100° C.

A 300 mL Hastelloy B autoclave equipped with a Hastelloy B dipleg, Hastelloy B nut and connector and Hastelloy B baffle, and a 50 mL stainless steel sample cylinder were dried in a 110° C. oven for at least 8 h. The dried autoclave and sample cylinder were then brought into a nitrogen glovebox. The autoclave was charged with 38.34 g of [1-butyl-3-methylimidazolium][Al$_2$Cl$_7$] and 129.4 g of n-hexane, which had previously been dried over activated 3 A molecular sieves, and the autoclave head was attached. The 50 mL sample cylinder was then charged with 4.02 g of 2-chloro-2-methylpropane, which had previously been dried over activated 3 A molecular sieves, and 10.0 g of the n-hexane feed. The sample cylinder was closed under nitrogen, and both the autoclave and the sample cylinder were removed from the glovebox. The composition of the n-hexane feed is listed in Table 37, entry 1. The autoclave was then heated to 100° C. with stirring at 300 rpm for 29 minutes, followed by stirring at 93 rpm for 30 minutes until the reaction temperature was reached. At this point, stirring was stopped, and the 2-chloro-2-methylpropane/n-hexane solution in the sample cylinder was added with an over-pressure of nitrogen. The nitrogen used to pressurize the charger and for all other work passed over a separate high surface sodium column. Once the addition was complete, stirring was set to 1700 rpm. Initially, the temperature decreased to 96° C. after 6 minutes of stirring, and the pressure was 340 psi (2.34 MPa) within the autoclave. After 6 minutes of reaction, the reaction mixture was analyzed by GC (entry 2. Table 37). During the course of the reaction, the reaction mixture was periodically analyzed online by GC. The pressure within the autoclave varied from 320-340 psi (2.21 to 2.34 MPa) at 100° C. during the course of the reaction. In order to analyze the paraffinic layer, the stirring was stopped, and the product was allowed to settle for 5 minutes. An aliquot was sampled directly from the autoclave by opening a valve from the autoclave, passing the paraffinic layer through a $SiO_2$ column, and then passing it directly into a GC sample loop. The GC method employed was UOP690. The mass ratio of liquid catalyst to hydrocarbon feed was 0.30, and the volume ratio was 0.15 using the following densities: 1.34 g % mL for the liquid catalyst and 0.659 g/mL for n-hexane. The mass reaction rate was 760, and the volume reaction rate was 1500 after 0.1 h.

available FT wax. The sample cylinder was closed under nitrogen, and both the autoclave and sample cylinder were removed from the glovebox. The autoclave containing the ionic liquid was then put under vacuum (50 mTorr, 6.7 Pa) and 2 g of anhydrous HCl was charged into the autoclave. The autoclave was then charged with 115 g of n-butane from a pressurized feed charger, without displacing the gases present in the autoclave. The composition of the n-butane feed is listed in Table 38, entry 1. The sample cylinder containing the FT wax was charged with 10.51 g of n-butane, and the cylinder was then heated to 80° C. in an oven. The autoclave was heated to 100° C. with stirring at 100 rpm. Once the temperature was achieved, stirring was stopped and the FT wax/n-butane solution in the sample cylinder was added with an over-pressure of nitrogen. Not all of the material was added: about 29.39 g of the material was added based on the mass difference within the sample cylinder before and after addition. Assuming that the material added was of similar composition to what was initially present in the sample cylinder, 20.3 g of FT wax and an additional 9.0 g of n-butane were added. The nitrogen used to pressurize the charger and for all other work passed over a separate high surface sodium column. Once the addition was complete, stirring was set to 1700 rpm. Initially, the temperature increased to 102° C., and the pressure was 760

TABLE 37

Isomerization and disproportionation of n-hexane at 100° C., 1700 rpm, Hastelloy B autoclave, wt. % of feed and reaction mixture

| Entry | time (h) | C3P | C4P | C5P | nC6 | iC6 | C7P | C8P | C7N | C8N | C8A | nC4-nC5[a] | nC5-nC6[a] | nC6-nC7[a] | nC7-nC8[a] | nC8-nC9[a] | nC9-nC10[a] | nC10+[a] |
|---|---|---|---|---|---|---|---|---|---|---|---|---|---|---|---|---|---|---|
| 1 | 0.0 | 0.00 | 0.00 | 0.00 | 98.02 | 1.34 | 0.60 | 0.00 | 0.00 | 0.00 | 0.00 | 0.03 | 0.00 | 0.00 | 0.00 | 0.00 | 0.00 | 0.01 |
| 2 | 0.1 | 0.21 | 3.84 | 4.94 | 73.53 | 9.83 | 3.03 | 0.44 | 0.22 | 0.34 | 0.05 | 0.00 | 0.00 | 0.00 | 0.22 | 0.42 | 0.38 | 0.47 |
| 3 | 1.2 | 0.73 | 12.20 | 13.33 | 45.08 | 14.92 | 6.62 | 1.63 | 0.57 | 0.80 | 0.09 | 0.02 | 0.00 | 0.00 | 0.00 | 1.32 | 1.12 | 1.55 |
| 4 | 4.0 | 0.80 | 13 26 | 14.58 | 38.16 | 15.80 | 7.95 | 2.22 | 0.62 | 1.08 | 0.12 | 0.00 | 0.00 | 0.02 | 0.00 | 1.79 | 1.48 | 2.07 |

[a]Unknowns eluting between the retention times for these normal paraffins and
[b]unknown eluting after nC10

Example 35: nC4/FT Wax—Stir Rate at 1700 rpm with [1-butyl-3-methylimidazolium][Al$_2$Cl$_7$] in Hastelloy C Autoclave at 100° C.

A 300 mL Hastelloy B autoclave equipped with a Hastelloy B dipleg and Hastelloy B nut and connector, Hastelloy B baffle, and 75 mL stainless steel sample cylinder were dried in a 110° C. oven for at least 8 h. The dried autoclave and sample cylinder were brought into a nitrogen glovebox and allowed to cool to ambient temperature. The autoclave was charged with 38.34 g of [1-butyl-3-methylimidazolium] [Al$_2$Cl$_7$], and the autoclave head was attached. The 75 mL sample cylinder was charged with 23.62 g of a commercially psi (5.24 MPa) within the autoclave. After 11 minutes of stirring, the temperature stabilized at 100° C. and the pressure was 765 psi (5.27 MPa). After 3.3 hours, stirring was stopped, and the paraffinic layer was analyzed by online GC. In order to analyze the paraffinic layer with online GC, the stirring was stopped, and the product was allowed to settle for 5 minutes. An aliquot was sampled directly from the autoclave by opening a valve from the autoclave, passing the paraffinic layer through a SiO$_2$ column, and then passing it directly into a GC sample loop. The GC method employed was UOP690. The reported results are depicted in Table 38. This procedure was repeated one more time and the results are reported in Table 38.

TABLE 38

Reverse disproportionation of an n-butane/FT wax feed at 100° C., 1700 rpm, Hastelloy B autoclave, wt. % of feed and reaction mixture

| time (h) | C3P | iC4 | nC4 | iC5 | nC5 | C6P | C7P | C8P | nC18+ | Other[a] | C4P | C5P | iC4/nC4 | iC5/nC5 |
|---|---|---|---|---|---|---|---|---|---|---|---|---|---|---|
| NA | 0.01 | 0.17 | 99.71 | 0.00 | 0.00 | 0.00 | 0.00 | 0.00 | 0.00 | 0.11 | 99.88 | 0.00 | 0.00 | NA |
| 0.0[b] | 0.0 | 0.0 | 86 | 0.0 | 70.0 | 0.0 | 0.0 | 0.0 | 14 | 0 | 86 | 0.0 | 0.00 | NA |
| 3.3 | 3.33 | 39.29 | 26.20 | 15.74 | 4.38 | 7.62 | 1.67 | 1.09 | 0.05 | 0.63 | 65.49 | 20.12 | 1.50 | 3.59 |
| 19.5 | 8.08 | 35.52 | 20.16 | 16.94 | 4.78 | 10.20 | 2.24 | 1.18 | 0.15 | 0.75 | 55.68 | 21.72 | 1.76 | 3.54 |

[a]Other compounds present,
[b]wt. % composition at t = 0 h is based on mass of added reagents Example 36: nC4/nC7—Stir Rate at 1700 rpm with [1-butyl-3-methylimidazolium][Al$_2$Cl$_7$] in Hastelloy C Autoclave at 100° C.

A 300 mL Hastelloy B autoclave equipped with a Hastelloy B dipleg and Hastelloy B nut and connector, Hastelloy B baffle, and 75 mL stainless steel sample cylinder were dried in a 110° C. oven for at least 8 h. The dried autoclave and sample cylinder were brought into a nitrogen glovebox and allowed to cool to ambient temperature. The autoclave was charged with 38.34 g of [1-butyl-3-methylimidazolium][Al$_2$Cl$_7$], and the autoclave head was attached. The 75 mL sample cylinder was charged with 43.30 g of n-heptane, which had previously been dried over activated 3 A molecular sieves. The sample cylinder was closed under nitrogen, and both the autoclave and sample cylinder were removed from the glovebox. The autoclave containing the ionic liquid was then put under vacuum (100 mTorr, 13.3 Pa) and 2 g of anhydrous HCl was charged into the autoclave. The autoclave was then charged with 85 g of n-butane from a pressurized feed charger, without displacing the gases present in the autoclave. The composition of the n-butane feed is listed in Table 39, entry 1. The autoclave was heated to 100° C. with stirring at 100 rpm. Once the temperature was achieved stirring was stopped and the n-heptane solution in the sample cylinder was added with an over-pressure of nitrogen, 42.94 g was actually added. The nitrogen used to pressurize the charger and for all other work passed over a separate high surface sodium column. Once the addition was complete, stirring was set to 1700 rpm. Initially, the temperature decreased to 96° C., and the pressure was 570 psi (3.93 MPa) within the autoclave. After 7 minutes of stirring, the temperature increased to 101° C. and the pressure was 540 psi (3.72 MPa). After 7 minutes, stirring was stopped and the paraffinic layer analyzed by online GC. In order to analyze the paraffinic layer with online GC, the stirring was stopped, and the product was allowed to settle for 5 minutes. An aliquot was sampled directly from the autoclave by opening a valve from the autoclave, passing the paraffinic layer through a SiO$_2$ column, and then passing it directly into a GC sample loop. The GC method employed was UOP690. After stirring was recommenced, the temperature stabilized at 100° C. after an additional 33 minutes of reaction. The results are depicted in Table 39. This procedure was repeated two more times and the results are reported in Table 39. The mass ratio of liquid catalyst to hydrocarbon feed was 0.32, and the volume ratio was 0.14 using the following densities: 1.34 g/mL for the liquid catalyst, 0.684 g/mL for n-heptane and 0.57 g/mL for n-butane.

Example 37: nC4/nC5—Stir Rate at 1700 rpm with [1-butyl-3-methylimidazolium][Al$_2$Cl$_7$] in Hastelloy C Autoclave at 100° C.

A 300 mL Hastelloy B autoclave equipped with a Hastelloy B dipleg and Hastelloy B nut and connector and a Hastelloy B baffle were dried in a 110° C. oven for at least 8 h. The dried autoclave was brought into a nitrogen glovebox and allowed to cool to ambient temperature. The autoclave was charged with 38.34 g of [1-butyl-3-methylimidazolium][Al$_2$Cl$_7$], and the autoclave head was attached. The autoclave was removed from the glovebox. The autoclave containing the ionic liquid was then put under vacuum (90 mTorr, 12.0 Pa), and 2 g of anhydrous HCl was charged into the autoclave. The autoclave was then charged with 41 g of n-butane from a pressurized feed charger, without displacing the gases present in the autoclave. The composition of the n-butane feed is listed in Table 40, entry 1. The autoclave was next charged with 96 g of n-pentane, which passed over a high surface sodium drier, from a pressurized feed charger, the mixture was stirred at ambient temperature for 5 minutes, and the reaction mixture was analyzed by online GC. In order to analyze the paraffinic layer with online GC, the stirring was stopped, and the product was allowed to settle for 5 minutes. An aliquot was sampled directly from the autoclave by opening a valve from the autoclave, passing the paraffinic layer through a SiO$_2$ column, and then passing it directly into a GC sample loop. The GC method employed was UOP690. After stirring was recommenced, the mixture was heated to 100° C., which took 49 minutes to reach. Once the temperature reached 100° C., the pressure was 830 psi (5.72 MPa). After 27 minutes of reaction at 100° C., the pressure was 910 psi (6.27 MPa). At this point, the reaction mixture was analyzed by online GC using the procedure described above. The reaction was continued at 100° C., and the results are depicted in Table 40. The mass ratio of liquid catalyst to hydrocarbon feed was 0.29, and the volume ratio was 0.13 using the following densities: 1.34 g/mL for the liquid catalyst, 0.626 g/mL for n-pentane and 0.57 g/mL for n-butane.

TABLE 39

Disproportionation/reverse disproportionation of an n-butane/n-heptane feed at 100° C., 1700 rpm, Hastelloy B autoclave, wt. % of feed and reaction mixture

| time (h) | C3P | iC4 | nC4 | iC5 | nC5 | C6P | C7P | C8P | Other[a] | C4P | C5P | iC4/nC4 | iC5/nC5 |
|---|---|---|---|---|---|---|---|---|---|---|---|---|---|
| NA | 0.01 | 0.17 | 99.71 | 0.00 | 0.00 | 0.00 | 0.00 | 0.00 | 0.11 | 99.88 | 0.00 | 0.00 | NA |
| 0.0[b] | 0.0 | 0.0 | 66 | 0.0 | 70.0 | 0.0 | 34 | 0.0 | 0.0 | 66 | 0.0 | 0.00 | NA |
| 0.1 | 1.02 | 12.06 | 47.16 | 8.52 | 1.21 | 6.08 | 20.30 | 1.70 | 1.95 | 59.22 | 9.73 | 0.26 | 7.04 |
| 5 | 3.19 | 30.44 | 27.57 | 16.83 | 4.41 | 10.02 | 3.98 | 1.86 | 1.70 | 58.01 | 21.24 | 1.10 | 3.82 |
| 21.5 | 4.91 | 34.56 | 21.19 | 17.66 | 4.97 | 10.63 | 2.98 | 1.61 | 1.49 | 55.75 | 22.63 | 1.63 | 3.55 |

[a]Other compounds present,

[b]wt. % composition at t = 0 h is based on mass of added reagents

TABLE 40

Disproportionation/reverse disproportionation of an n-butane/n-pentane feed at 100° C., 1700 rpm, Hastelloy B autoclave, wt. % of feed and reaction mixture

| time (h) | C3P | iC4 | nC4 | iC5 | nC5 | C6P | C7P | C8P | nC8+ | Other[a] | C4P | C5P | iC4/nC4 | iC5/nC5 |
|---|---|---|---|---|---|---|---|---|---|---|---|---|---|---|
| NA | 0.01 | 0.17 | 99.71 | 0.00 | 0.00 | 0.00 | 0.00 | 0.00 | 0.00 | 0.11 | 99.88 | 0.00 | 0.00 | NA |
| 0.0[b] | 0.0 | 0.29 | 23.49 | 0.92 | 74.96 | 0.17 | 0.06 | 0.00 | 0.04 | 0.07 | 23.78 | 75.88 | 0.01 | 0.01 |
| 1.3 | 1.29 | 29.11 | 19.18 | 19.77 | 7.87 | 13.58 | 4.83 | 2.23 | 1.64 | 0.50 | 48.29 | 27.64 | 1.52 | 2.51 |
| 6.3 | 3.09 | 32.05 | 18.27 | 19.37 | 5.57 | 13.75 | 4.18 | 2.05 | 1.33 | 0.34 | 50.32 | 24.94 | 1.75 | 3.48 |
| 24.3 | 5.34 | 31.64 | 17.77 | 18.60 | 5.34 | 13.86 | 3.90 | 1.92 | 1.31 | 0.32 | 49.41 | 23.94 | 1.78 | 3.48 |

[a]Other compounds present,
[b]wt. % composition for the first GC recorded at ambient temperature

Example 38: Tuning Examples Using Above Data—C/H=0.41

The data shown in Table 41 are from Examples 33, 35 and 36 at the end of the run. As illustrated in these Examples, the feed C/H molar ratio is similar, so the product composition should be similar at the end of the reaction if it is substantially equilibrated even though the starting feed compositions are significantly different.

TABLE 41

Data from Examples 33, 35 and 36 from the end of the run

|  | 1 | 2 | 3 |
|---|---|---|---|
| Feed (wt. %) | | | |
| C3P | 0.0 | 0.0 | 0.0 |
| C4P | 85.9 | 66.4 | 29.8 |
| C5P | 0.0 | 0.0 | 70.2 |
| C6P | 0.0 | 0.0 | 0.0 |
| C7P | 0.0 | 33.6 | 0.0 |
| C8P | 0.0 | 0.0 | 0.0 |
| C9+ | 14.1 (FT Wax) | 0.0 | 0.0 |
| SUM | 100.0 | 100.0 | 100.0 |
| C/H | 0.408[a] | 0.412 | 0.412 |
| Product (wt. %) | | | |
| C3P | 8.1 | 4.9 | 4.0 |
| C4P | 55.7 | 55.8 | 51.5 |
| C5P | 21.7 | 22.6 | 23.8 |
| C6P | 10.2 | 10.6 | 12.5 |
| C7P | 2.2 | 3.0 | 4.0 |
| C8P | 1.2 | 1.6 | 1.8 |
| C9+ | 0.3 | 0.7 | 1.8 |
| SUM | 99.4 | 99.2 | 99.3 |
| % C4P Conversion | 35 | 16 | −72 |
| % C9+ Conversion | >99 | NA | NA |
| % C7P Conversion | NA | 91 | NA |
| % C5P Conversion | NA | NA | 66 |
| Wt. % Selectivity | | | |
| C3P | 18 | 8 | 9 |
| C4P | 0 | 0 | 46 |
| C5P | 49 | 56 | 0 |
| C6P | 23 | 26 | 27 |
| C7P | 5 | 0 | 9 |
| C8P | 3 | 5 | 4 |
| C9+ | 1 | 2 | 4 |
| SUM | 99 | 97 | 99 |

[a]Using the % C and % H values determined from analysis of the FT wax using the ASTM D5291 method

Example 39: Tuning Examples Using Above Data—C/H=0.40

The data shown in Table 42 are from Examples 18, 26 and 27 at the end of the run. As illustrated in these Examples, the feed C/H molar ratio is similar, so the product composition should be similar at the end of the reaction if it is substantially equilibrated even though the starting feed compositions are significantly different.

TABLE 42

Data from Examples 18, 26 and 27 from the end of the run

|  | 1 | 2 | 3 |
|---|---|---|---|
| Feed (wt. %) | | | |
| C3P | 0.0 | 0.0 | 0.0 |
| C4P | 76.5 | 90.1 | 87.6 |
| C5P | 23.5 | 0.0 | 0.0 |
| C6P | 0.0 | 0.0 | 0.0 |
| C7P | 0.0 | 9.9 | 0.0 |
| C8P | 0.0 | 0.0 | 0.0 |
| C9+ | 0.0 | 0.0 | 12.4 (nC9) |
| SUM | 100.0 | 100.0 | 100.0 |
| C/H | 0.404 | 0.403 | 0.406 |
| Product (wt. %) | | | |
| C3P | 1.4 | 5.2 | 3.4 |
| C4P | 74.4 | 77.1 | 76.4 |
| C5P | 17.2 | 13.9 | 14.9 |
| C6P | 5.3 | 2.9 | 4.0 |
| C7P | 0.7 | 0.4 | 0.6 |
| C8P | 0.6 | 0.2 | 0.3 |
| C9+ | 0.2 | 0.1 | 0.2 |
| SUM | 99.8 | 99.8 | 99.8 |
| % C4P Conversion | 3 | 14% | 13% |
| % C5P Conversion | 27 | NA | NA |
| % C7P Conversion | NA | 96 | NA |
| % nC9 Conversion | NA | NA | >99 |
| Wt. % Selectivity | | | |
| C3P | 16 | 23 | 14 |
| C4P | 0 | 0 | 0 |
| C5P | 0 | 62 | 63 |
| C6P | 63 | 13 | 17 |
| C7P | 9 | 0 | 2 |
| C8P | 7 | 1 | 1 |
| C9+ | 3 | 0 | 1 |
| SUM | 98 | 99 | 98 |

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A process of tuning a hydrocarbon product composition comprising:
    selecting a range of paraffins;
    determining a series of equilibrium constants for isomerization and disproportionation reactions of the selected range of paraffins;
    selecting a hydrocarbon product composition with a C/H molar ratio based on the series of equilibrium constants for the selected range of paraffins;
    selecting a hydrocarbon feed with the same C/H molar ratio as the hydrocarbon product composition, the selected hydrocarbon feed comprising at least one $C_n$ alkane, where n=1-200;
    passing the selected hydrocarbon feed into a reaction zone;
    reacting the selected hydrocarbon feed by contacting the selected hydrocarbon feed with a liquid catalyst comprising an ionic liquid and a carbocation promoter in the reaction zone under tuning conditions to form the hydrocarbon product composition, wherein (i) the tuning conditions comprise at least one of a temperature in a range of about 25° C. to about 150° C. and a pressure in a range of about 0 MPa to about 20.7 MPa, (ii) reactions in the reaction zone comprise isomerization and disproportionation, and (iii) the carbocation promoter promotes disproportionation reactions; and
    recovering the hydrocarbon product composition, wherein the number of moles of hydrocarbons in said hydrocarbon product composition is equal to the number of moles of hydrocarbons in said hydrocarbon feed.

2. The process of claim 1 wherein the C/H molar ratio of the selected hydrocarbon feed is in the range of about 0.25 to about 0.50.

3. The process of claim 1 further comprising:
    selecting a range of a desired property for the hydrocarbon product composition, wherein the desired property is at least one of a research octane number, a boiling point, a boiling range, a cloud point, a pour point, a viscosity, a density, and a Reid vapor pressure; and
    wherein selecting the hydrocarbon feed with the same C/H molar ratio as the hydrocarbon product composition further comprises selecting the hydrocarbon feed based on the range of the desired property for the hydrocarbon product composition.

4. The process of claim 1 wherein the ionic liquid comprises an organic cation and an anion and wherein the organic cation is selected from the group consisting of:

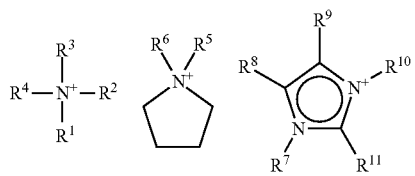

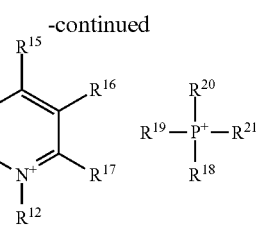

and lactamium based cations, where $R^1$-$R^{21}$ are independently selected from $C_1$-$C_{20}$ hydrocarbons, $C_1$-$C_{20}$ hydrocarbon derivatives, halogens, and H; and wherein the anion is selected from the group consisting of: at least one halide, at least one sulfate, at least one bisulfate, at least one nitrate, at least one sulfonate, at least one fluoroalkanesulfonate, and combinations thereof.

5. The process of claim 1 further comprising separating the ionic liquid from the hydrocarbon product composition and regenerating the separated ionic liquid.

6. A process of tuning a hydrocarbon product composition comprising:
    selecting a range of paraffins;
    determining a series of equilibrium constants for isomerization and disproportionation reactions of the selected range of paraffins;
    selecting a hydrocarbon product composition with a C/H molar ratio based on the series of equilibrium constants for the selected range of paraffins;
    selecting a hydrocarbon feed with the same C/H molar ratio as the hydrocarbon product composition, the selected hydrocarbon feed comprising at least one $C_n$ alkane, where n=1-200;
    passing the selected hydrocarbon feed into a reaction zone; and
    reacting the selected hydrocarbon feed by contacting the selected hydrocarbon feed with a liquid catalyst comprising an ionic liquid and a carbocation promoter in the reaction zone to form the hydrocarbon product composition, wherein (i) the reactions in the reaction zone comprise isomerization and disproportionation and (ii) the carbocation promoter promotes disproportionation reactions.

7. The process of claim 6 wherein the C/H molar ratio of the selected hydrocarbon feed is in the range of about 0.25 to about 0.50.

8. The process of claim 6 further comprising:
    selecting a range of a desired property for the hydrocarbon product composition, wherein the desired property is at least one of a research octane number, a boiling point, a boiling range, a cloud point, a pour point, a viscosity, a density, and a Reid vapor pressure; and
    wherein selecting the hydrocarbon feed with the same C/H molar ratio as the hydrocarbon product composition further comprises selecting the hydrocarbon feed based on the range of the desired property for the hydrocarbon product composition.

9. The process of claim 6 wherein the hydrocarbon product composition comprises at least one $C_z$ alkane where n<z<m, and wherein the selected hydrocarbon feed comprises a first $C_n$ alkane where n=1-4, and a second $C_m$ alkane where m=5-12.

10. The process of claim 6 wherein the hydrocarbon product composition comprises at least one $C_z$ alkane where n<z<m, and wherein the selected hydrocarbon feed comprises a first $C_n$ alkane where n=1-9, and a second $C_m$ alkane where m=6-16.

11. The process of claim 6 wherein the hydrocarbon product composition comprises at least one $C_z$ alkane where n<z<m, and wherein the selected hydrocarbon feed comprises a first $C_n$ alkane where n=1-10, and a second $C_m$ alkane where m=6-25.

12. The process of claim 6 wherein the hydrocarbon product composition comprises at least one $C_z$ alkane where n<z<m, and wherein the selected hydrocarbon feed comprises a first $C_n$ alkane where n=1-28, and a second $C_m$ alkane where m=6-100.

13. The process of claim 6 wherein the ionic liquid comprises an organic cation and an anion and wherein the organic cation is selected from the group consisting of:

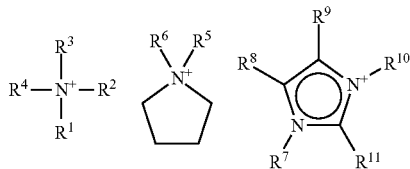

-continued

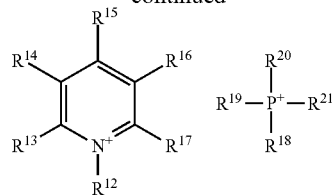

and lactamium based cations, where $R^1$-$R^{21}$ are independently selected from $C_1$-$C_{20}$ hydrocarbons, $C_1$-$C_{20}$ hydrocarbon derivatives, halogens, and H; and wherein the anion is selected from the group consisting of: at least one halide, at least one sulfate, at least one bisulfate, at least one nitrate, at least one sulfonate, at least one fluoroalkanesulfonate, and combinations thereof.

14. The process of claim 6 wherein the carbocation promoter comprises halo-alkanes, mineral acids, or combinations thereof, and wherein a molar ratio of the carbocation promoter to the ionic liquid is in a range of about 0.1:1 to about 3:1.

15. The process of claim 6 further comprising separating the ionic liquid from the hydrocarbon product composition and regenerating the separated ionic liquid.

* * * * *